United States Patent
Gerber et al.

(10) Patent No.: US 9,789,252 B2
(45) Date of Patent: Oct. 17, 2017

(54) THERAPY PROGRAM MODIFICATION BASED ON A THERAPY FIELD MODEL

(75) Inventors: Martin T. Gerber, Maple Grove, MN (US); John C. Rondoni, Plymouth, MN (US)

(73) Assignee: Medtronic, Inc., Minneapolis, MN (US)

(*) Notice: Subject to any disclaimer, the term of this patent is extended or adjusted under 35 U.S.C. 154(b) by 1727 days.

(21) Appl. No.: 12/989,754

(22) PCT Filed: Jan. 22, 2009

(86) PCT No.: PCT/US2009/031650
§ 371 (c)(1),
(2), (4) Date: Oct. 26, 2010

(87) PCT Pub. No.: WO2009/134475
PCT Pub. Date: Nov. 5, 2009

(65) Prior Publication Data
US 2011/0208012 A1    Aug. 25, 2011

Related U.S. Application Data

(60) Provisional application No. 61/048,761, filed on Apr. 29, 2008.

(51) Int. Cl.
*A61B 5/00* (2006.01)
*A61M 5/172* (2006.01)
(Continued)

(52) U.S. Cl.
CPC ....... *A61M 5/1723* (2013.01); *A61N 1/36185* (2013.01); *A61N 1/37235* (2013.01);
(Continued)

(58) Field of Classification Search
USPC ...... 607/1–2, 59, 62, 66, 115; 600/300–301, 600/512
See application file for complete search history.

(56) References Cited

U.S. PATENT DOCUMENTS 5,201,865 A    4/1993  Kuehn
5,895,416 A    4/1999  Barreras, Sr. et al.
(Continued)

FOREIGN PATENT DOCUMENTS

WO    2007097870 A1    8/2007
WO    2008005142 A1    1/2008
WO    2008070140 A2    6/2008

OTHER PUBLICATIONS

Response to Examination Report dated May 6, 2014, from Counterpart European Patent Application No. 09739278.1, filed Nov. 4, 2014, 6 pp.
(Continued)

*Primary Examiner* — Deborah Malamud
(74) *Attorney, Agent, or Firm* — Shumaker & Sieffert, P.A.

(57) ABSTRACT

Techniques for modeling therapy fields for therapy delivered by medical devices are described. Each therapy field model is based on a set of therapy parameters and represents where therapy will propagate from the therapy system delivering therapy according to the set of therapy parameters. Therapy field models may be useful in guiding the modification of therapy parameters. As one example, a processor compares an algorithmic model of a therapy field to a reference therapy field and adjusts at least one therapy parameter based on the comparison. As another example, a processor adjusts at least one therapy parameter to increase an operating efficiency of the therapy system while substantially maintaining the modeled therapy field.

30 Claims, 21 Drawing Sheets

(51) Int. Cl.
  *A61N 1/372* (2006.01)
  *G06F 19/00* (2011.01)
  *A61M 5/142* (2006.01)
  *A61N 1/36* (2006.01)

(52) U.S. Cl.
  CPC ..... *A61N 1/37247* (2013.01); *A61N 1/37264* (2013.01); *G06F 19/325* (2013.01); *G06F 19/3406* (2013.01); *G06F 19/3437* (2013.01); *A61M 5/14276* (2013.01); *A61M 2205/054* (2013.01); *A61M 2210/0693* (2013.01); *A61N 1/36003* (2013.01); *A61N 1/36007* (2013.01); *A61N 1/36071* (2013.01); *A61N 1/36082* (2013.01)

(56) References Cited

U.S. PATENT DOCUMENTS

| | | | |
|---|---|---|---|
| 6,609,032 | B1 | 8/2003 | Woods et al. |
| 7,024,246 | B2 | 4/2006 | Acosta et al. |
| 7,035,690 | B2 | 4/2006 | Goetz |
| 7,346,382 | B2 * | 3/2008 | McIntyre et al. ............. 600/407 |
| 7,395,113 | B2 | 7/2008 | Heruth et al. |
| 7,522,061 | B2 | 4/2009 | Rondoni et al. |
| 7,822,483 | B2 | 10/2010 | Stone et al. |
| 8,380,321 | B2 | 2/2013 | Goetz et al. |
| 8,548,596 | B2 | 10/2013 | Gerber et al. |
| 8,554,331 | B2 | 10/2013 | Gerber et al. |
| 8,792,991 | B2 | 7/2014 | Gerber et al. |
| 8,958,870 | B2 | 2/2015 | Gerber et al. |
| 2005/0033380 | A1 | 2/2005 | Tanner et al. |
| 2005/0070781 | A1 | 3/2005 | Dawant et al. |
| 2005/0209512 | A1 | 9/2005 | Heruth et al. |
| 2006/0017749 | A1* | 1/2006 | McIntyre et al. ............. 345/664 |
| 2006/0271118 | A1 | 11/2006 | Libbus et al. |
| 2007/0100388 | A1 | 5/2007 | Gerber et al. |
| 2007/0142874 | A1 | 6/2007 | John |
| 2007/0176131 | A1 | 8/2007 | Takahashi |
| 2007/0203539 | A1 | 8/2007 | Stone et al. |
| 2007/0203540 | A1 | 8/2007 | Goetz et al. |
| 2007/0203541 | A1 | 8/2007 | Goetz et al. |
| 2007/0203546 | A1 | 8/2007 | Stone et al. |
| 2007/0255176 | A1 | 11/2007 | Rondoni et al. |
| 2008/0022992 | A1 | 1/2008 | Wahl |
| 2011/0040547 | A1 | 2/2011 | Gerber et al. |

OTHER PUBLICATIONS

Examination Report from counterpart European Patent Application No. 09739278.1, dated May 6, 2014, 4 pp.
International Search Report, from International Application No. PCT/US2009/031650, dated Nov. 5, 2009, 3 pp.
International Preliminary Report on Patentability from International Application No. PCT/US2009/031650, dated Nov. 2, 2010, 6 pp.
Summons to attend Oral proceedings pursuant to Rule 115(1) EPC, from counterpart European Patent Application No. 09739278.1, dated Jan. 5, 2015, 5 pp.
Response to communication dated Jan. 5, 2015, from counterpart European Patent Application No. 09739278.1, filed on Aug. 14, 2015, 12 pp.
Intention to Grant from counterpart European Patent Application No. 09739278.1, dated Sep. 22, 2015, 5 pp.
Written Opinion of the International Search Authority, from International Application No. PCT/US2009/031650, dated Oct. 29, 2010, 5 pp.

* cited by examiner

THERAPY PROGRAM MODIFICATION BASED ON A THERAPY FIELD MODEL

This application claims the benefit of and is a U.S. National Stage filing under 35 U.S.C. §371 of PCT Application Serial No. PCT/US09/31650, filed Jan. 22, 2009 and entitled, "THERAPY PROGRAM MODIFICATION BASED ON A THERAPY FIELD MODEL," which in turn claims the benefit of U.S. Provisional Application No. 61/048,761, filed Apr. 29, 2008 and entitled "THERAPY PROGRAM MODIFICATION BASED ON A THERAPY FIELD MODEL." The entire disclosure of PCT Application Serial No. PCT/US09/31650 and U.S. Provisional Application No. 61/048,761 is incorporated by reference herein in its entirety.

TECHNICAL FIELD

The disclosure relates to medical devices, and, more particularly, determination of therapy parameter values for therapy delivered by medical devices.

BACKGROUND

Implantable medical devices, such as electrical stimulators or therapeutic agent delivery devices, may be used in different therapeutic applications, such as deep brain stimulation (DBS), spinal cord stimulation (SCS), pelvic stimulation, gastric stimulation, peripheral nerve stimulation or delivery of pharmaceutical agent, insulin, pain relieving agent or anti-inflammatory agent to a target tissue site within a patient. A medical device may be used to deliver therapy to a patient to treat a variety of symptoms or patient conditions such as chronic pain, tremor, Parkinson's disease, other types of movement disorders, seizure disorders (e.g., epilepsy), urinary or fecal incontinence, sexual dysfunction, obesity, mood disorders, gastroparesis or diabetes. In some cases, the electrical stimulation may be used for muscle stimulation, e.g., functional electrical stimulation (FES) to promote muscle movement or prevent atrophy. In some therapy systems, an implantable electrical stimulator delivers electrical therapy to a target tissue site within a patient with the aid of one or more medical leads that include electrodes. In addition to or instead of electrical stimulation therapy, a medical device may deliver a therapeutic agent to a target tissue site within a patient with the aid of one or more fluid delivery elements, such as a catheter.

During a programming session, which may occur during implant of the medical device, during a trial session, or during a follow-up session after the medical device is implanted in the patient, a clinician may select therapy parameter values for the medical device that provide efficacious therapy to the patient. In the case of electrical stimulation, the therapy parameters may include an electrode combination, and an amplitude, which may be a current or voltage amplitude, a pulse width, and a pulse rate for stimulation signals to be delivered to the patient. In the case of a therapeutic agent delivery device, the therapy parameters may include a dose (e.g., a bolus or a group of boluses) size, a frequency of bolus delivery, a concentration of a therapeutic agent in the bolus, a type of therapeutic agent to be delivered to the patient (if the medical device is configured to deliver more than one type of agent), a lock-out interval, and so forth.

A group of therapy parameter values may be referred to as a therapy program. A medical device may deliver therapy to a patient according to one or more stored therapy programs.

SUMMARY

In general, the disclosure is directed toward modifying one or more therapy parameter values for therapy delivered by a medical device based on an algorithmic model of a therapy field. The algorithmic model of a therapy field may represent where therapy will propagate from the therapy system that delivers therapy according to a particular therapy parameter set (or "therapy program"), which defines a value for at least one therapy parameter.

In one example of modifying one or more therapy parameter values defined by a first therapy program, a therapy field model generated based on the first therapy program may be compared to a reference therapy field with known efficacy for treating a disease or patient condition, or producing a therapeutic outcome. Based on the comparison, one or more therapy parameter values of the first therapy program may be modified to generate a second therapy program that results in a modified therapy field that may more closely match the reference field than the therapy field associated with the first therapy program. An additional comparison may be made between the modified therapy field and the reference field to determine if modification to the therapy parameter values of the second parameter set is desirable.

In some examples, during therapy delivery according to a therapy program, a processor may monitor a physiological parameter of a patient, such as by monitoring a signal received from a sensor that generates a signal that changes as a function of the physiological parameter. The processor may detect the occurrence of one or more patient events based on the signal. The patient event may indicate a change in the therapeutic efficacy of the therapy program, and may be, for example, the occurrence of a particular symptom related to the patient condition or a side effect of the therapy delivery. In response to the detection of a patient event, the processor may analyze the therapy program in view of therapy guidelines that provide information for managing a particular patient condition. In one example, the therapy guidelines may define a reference therapy field, provide a list of functional outcomes for the therapy delivery, and identify target anatomical structures for the therapy delivery. The processor may, for example, compare an algorithmic model of a therapy field generated based on therapy delivery according to the therapy program with the reference therapy field in order to determine whether to modify the therapy program.

In one example, upon detecting the patient event, the processor may select a different set of therapy guidelines and generate another therapy program based on the new set of therapy guidelines in order to generate a different therapy field (e.g., a stimulation field) that may better address the patient condition. As another example, the processor may use the same set of therapy guidelines but increase the strength of the therapy delivery (e.g., increase the stimulation) to increase the size of the therapy field. In either example, the processor may adjust a value of one or more therapy parameters based on the analysis of the therapy parameter set in view of one or more sets of therapy guidelines.

In another example of modifying a therapy program based on an algorithmic model of a therapy field, one or more of the therapy parameter values of the therapy program may be adjusted to increase an operating efficiency of the therapy system while substantially maintaining the therapy field that results from therapy delivery based on the therapy program. Substantially maintaining the therapy field may be desirable if the therapy field is known to provide efficacious therapy for the patient, which may be indicated by therapeutic results with minimal side effects. The operating efficiency of the therapy system may be increased, for example, by decreasing power consumption or operating at efficient amplitudes based on voltage multiplier levels. In some examples, an algorithmic model of the therapy field may be generated based on the adjusted parameter values and compared to the original modeled therapy field. If the difference between one or more field characteristics of the therapy field model generated according to the adjusted parameters and the original therapy field model are below a threshold, a processor of the therapy system may determine that the therapy field is substantially maintained.

In one example, the disclosure describes a method comprising determining a first therapy program that comprises a set of therapy parameter values, generating an algorithmic model of a therapy field based on the first therapy program, wherein the algorithmic model of the therapy field represents where therapy will propagate from a therapy system delivering the therapy according to the first therapy program, determining therapy guidelines based on a patient condition, wherein the therapy guidelines comprise a reference therapy field, comparing the algorithmic model of the first therapy field to the reference therapy field, and adjusting a value of at least one of the therapy parameters of the first therapy program to generate a second therapy program based on the comparison.

In another example, the disclosure describes a system comprising a therapy system that delivers a therapy to a patient according to a first therapy program comprising a set of therapy parameter values and a processor that generates an algorithmic model of a therapy field based on the therapy program, the model representing where the therapy will propagate from the therapy system when the medical device delivers therapy according to the first therapy program, determines therapy guidelines based on a patient condition, wherein the therapy guidelines comprise a reference therapy field, compares the algorithmic model of the therapy field to the reference therapy field, and, based on the comparison, adjusts a value of at least one of the therapy parameters of the first therapy program to generate a second therapy program.

In another example, the disclosure describes a therapy system comprising means for determining a first therapy program that comprises a set of therapy parameter values, means for delivering a therapy to a target therapy site in a patient according to the first therapy program, and means for generating an algorithmic model of a therapy field based on the first therapy program, the model representing where the therapy will propagate from the means for delivering, determining therapy guidelines based on a patient condition, wherein the therapy guidelines comprise a reference therapy field, comparing the algorithmic model of the therapy field to the reference therapy field, and adjusting a value of at least one therapy parameter of the first therapy program to generate a second therapy program based on the comparison.

In another example, the disclosure describes a method comprising delivering therapy to a patient via a therapy system according to a therapy program, generating an algorithmic model of a therapy field based on the therapy program, wherein the algorithmic model of the therapy field represents where therapy will propagate from the therapy system delivering the therapy according to the therapy program, detecting a patient event, upon detecting the patient event, referencing therapy guidelines that comprise a reference therapy field, comparing the algorithmic model of the therapy field to the reference therapy field, and adjusting a value of at least one therapy parameter of the therapy program based on the comparison between the algorithmic model of the therapy field and the reference therapy field.

In another example, the disclosure describes a method comprising determining a first therapy program that comprises a set of therapy parameters values, generating an algorithmic model of a therapy field based on the first therapy program, the algorithmic model representing where therapy will propagate from the therapy system delivering therapy according to the first therapy program, and automatically determining a second therapy program that increases an operating efficiency of the therapy system while substantially maintaining the therapy field.

In another example, the disclosure describes a therapy system comprising a medical device that delivers a therapy to a patient according to a first therapy program that comprises a first set of therapy parameters and a processor that generates an algorithmic model of a therapy field based on the first therapy program, wherein the model represents where the therapy will propagate from the medical device delivering therapy according to the first therapy program, and automatically determines a second therapy program that increases an operating efficiency of the therapy system while substantially maintaining the therapy field.

In yet another example, the disclosure describes a system comprising means for determining a therapy program that comprises a first set of therapy parameters values, means for delivering a therapy to a target therapy site in a patient according to the therapy program, and means for generating an algorithmic model of a therapy field based on the therapy program, wherein the model represents where the therapy will propagate from the means for delivery and automatically determining a second set of therapy parameters that increase an operating efficiency of the therapy system while substantially maintaining the therapy field.

DETAILED DESCRIPTION

In general, the disclosure is directed toward modifying one or more therapy parameter values for therapy delivered by a medical device based on an algorithmic model of a therapy field. An algorithmic model of a therapy field may be generated based on a therapy parameter set that defines a value for at least one therapy parameter, and represents where therapy will propagate from the therapy system delivering therapy according to the therapy parameter set.

Figure 1A:
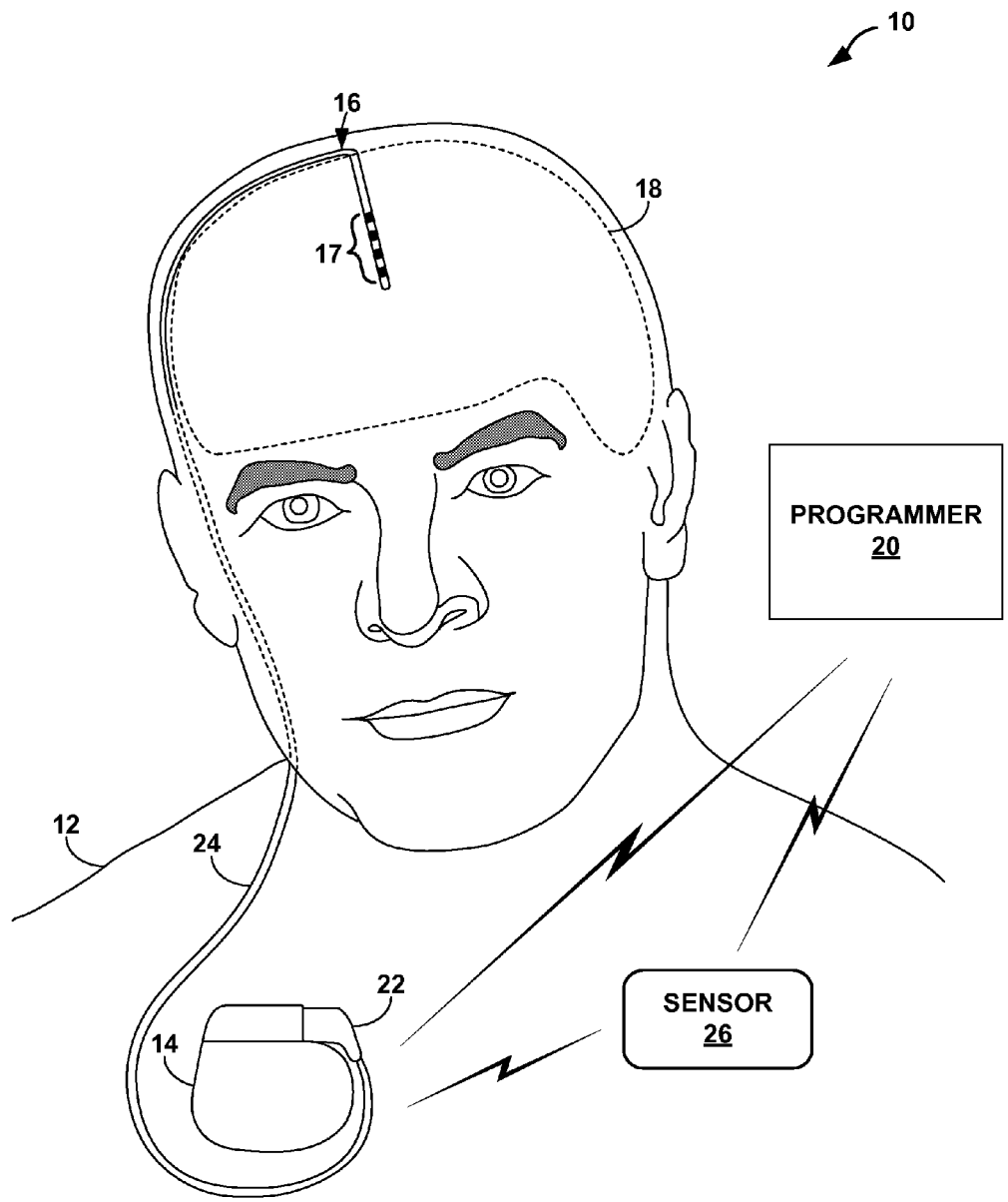
FIGS. 1A and 1B are conceptual diagrams illustrating example therapy systems that provide electrical stimulation therapy to a patient.

FIG. 1A is a conceptual diagram illustrating an example therapy system 10 that provides electrical stimulation therapy to patient 12. Therapy system 10 includes IMD 14 and medical lead 16. In the example shown in FIG. 1A, IMD 14 provides deep brain stimulation (DBS) to brain 18 of patient 12. Lead 16 is implanted within patient 12 such that one or more electrodes 17 carried by lead 16 are located proximate to a target tissue site within brain 18. IMD 14 provides electrical stimulation to regions within brain 18 in order to manage a condition of patient 12, such as to mitigate the severity or duration of the patient condition. In some examples, more than one lead 16 may be implanted within brain 18 of patient 12 to provide stimulation to multiple anatomical regions of brain 18. As shown in FIG. 1A, system 10 may also include a programmer 20, which may be a handheld device, portable computer, or workstation that provides a user interface to a clinician or other user. The clinician may interact with the user interface to program stimulation parameters for IMD 14.

DBS may be used to treat various patient conditions, such as, but not limited to, seizure disorders (e.g., epilepsy), pain, migraine headaches, psychiatric disorders (e.g., obsessive compulsive disorder, mood disorders or anxiety disorders), movement disorders (e.g., essential tremor or Parkinson's disease), Huntington's disease, and other neurodegenerative disorders. The anatomic region within patient 12 that serve as the target tissue site for stimulation delivered by IMD 14 may be selected based on the patient condition. For example, stimulating an anatomical region, such as the Substantia Nigra, in brain 18 may reduce the number and magnitude of tremors experienced by patient 12. Other example target anatomical regions for treatment of movement disorders may include the subthalamic nucleus, globus pallidus interna, ventral intermediate, and zona inserta. Anatomical regions such as these may be targeted by the clinician during implantation of lead 16. In other words, the clinician may attempts to position lead 16 within or proximate to these target regions within brain 18.

While DBS may successfully reduce symptoms of some neurological diseases, the stimulation may cause unwanted side effects as well. Side effects may include incontinence, tingling, loss of balance, paralysis, slurred speech, loss of memory, and many other neurological issues. Side effects may be mild to severe; however, most side effects are reversible when stimulation is stopped. DBS may cause one or more side effects by inadvertently providing electrical stimulation to anatomical regions near the targeted anatomical region. For this reason, the clinician may program the stimulation parameters in order to balance effective therapy and minimal side effects.

DBS lead 16 may include one or more electrodes 17 placed along the longitudinal axis of lead 16. In some examples, electrodes 17 may include at least one ring electrode that resides along the entire circumference of lead 16. Electrical current from the ring electrodes propagates in all directions from the active electrode. The resulting stimulation field reaches anatomical regions of brain 18 within a certain distance in all directions. The stimulation field may reach the target anatomical region, but the stimulation field may also affect non-target anatomical regions and produce unwanted side effects. In other examples, lead 16 may include a complex electrode array geometry that includes segmented or partial ring electrodes in addition to or instead of ring electrodes. The electrodes in a complex electrode array may be located at different axial and angular positions around the circumference of the lead, as well as at different longitudinal positions (i.e., along the longitudinal axis of lead 16). A complex electrode array geometry may be useful for customizing the stimulation field and provide improved therapy while decreasing side effects. For example, with a complex electrode array, electrodes may be selected along the longitudinal axis of lead 16 as well as along the circumference of lead 16. Activating selective electrodes of lead 16 can produce customizable stimulation fields that may be directed to a particular side of lead 16 in order to isolate the stimulation field around the target anatomical region of brain 18. In this manner, specific electrodes of the complex electrode array geometry may be selected to produce a stimulation field at desired portions of the circumference instead of always producing a stimulation field around the entire circumference of the lead, as with some ring electrodes.

Producing irregular stimulation fields with a lead 16 with a complex electrode geometry may allow therapy system 10 to more effectively treat certain anatomical regions of brain 18. In some cases, a therapy system 10 including lead 16 with a complex electrode array may also help reduce or eliminate side effects from more spherical stimulation fields produced by a conventional array of ring electrodes. The center of the stimulation field may be moved away from lead 16 to avoid unwanted stimulation or compensate for inaccurately placed leads.

In the example shown in FIG. 1A, lead 16 is coupled to IMD 14 via connector 22, which defines a plurality of electrical contacts for electrically coupling electrodes 17 to a stimulation generator within IMD 14. Connector 22 may also be referred to as a connector block or header of IMD 14. Lead 16 is indirectly coupled to connector 22 with the aid of lead extension 24. In some examples, lead 16 may be directly coupled to connector 22 without the aid of extension 24.

Programmer 20 is an external computing device that is configured to wirelessly communicate with IMD 14. For example, programmer 20 may be a clinician programmer that the clinician uses to communicate with IMD 14. Alternatively, programmer 20 may be a patient programmer that allows patient 12 to view and modify therapy parameters. The clinician programmer may include more programming features than the patient programmer. In other words, more complex or sensitive tasks may only be allowed by the clinician programmer to prevent patient 12 from making undesired changes to IMD 14.

Programmer 20 may be a hand-held computing device that includes a display viewable by the user and a user input mechanism that can be used to provide input to programmer 20. For example, programmer 20 may include a small display screen (e.g., a liquid crystal display or a light emitting diode display) that presents information to the user. In addition, programmer 20 may include a keypad, buttons, a peripheral pointing device, touch screen or another input mechanism that allows the user to navigate though the user interface of programmer 20 and provide input.

If programmer 20 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 20 may be a touch screen that allows the user to provide input directly to the user interface shown on the display. The user may use a stylus or their finger to provide input to the display.

In other examples, rather than being a handheld computing device or a dedicated computing device, programmer 20 may be a larger workstation or a separate application within another multi-function device. For example, the multi-function device may be a cellular phone or personal digital assistant that can be configured to an application to simulate programmer 20. Alternatively, a notebook computer, tablet computer, or other personal computer may enter an application to become programmer 20 with a wireless adapter connected to the personal computer for communicating with IMD 14.

When programmer 20 is configured for use by the clinician, programmer 20 may be used to transmit initial programming information to IMD 14. This initial information may include system 10 hardware information such as the type of lead 16, the position of lead 16 within patient 12, the therapy parameter values of therapy programs stored within IMD 14 or within programmer 20, and any other information the clinician desires to program into IMD 14.

With the aid of programmer 20 or another computing device, a clinician may select values for therapy parameters for controlling therapy delivery by therapy system 10. The values for the therapy parameters may be organized into a group of parameter values referred to as a "therapy program" or "therapy parameter set." "Therapy program" and "therapy parameter set" are used interchangeably herein. In the case of electrical stimulation, the therapy parameters may include an electrode combination, and an amplitude, which may be a current or voltage amplitude, and, if IMD 14 delivers electrical pulses, a pulse width, and a pulse rate for stimulation signals to be delivered to the patient. Other example therapy parameters include a slew rate, duty cycle, and phase of the electrical stimulation signal. An electrode combination may include a selected subset of one or more electrodes 17 located on one or more implantable lead 16 coupled to IMD 14. The electrode combination may also refer to the polarities of the electrodes in the selected subset. By selecting particular electrode combinations, a clinician may target particular anatomic structures within brain 18 of patient 12. In addition, by selecting values for slow rate, duty cycle, phase amplitude, pulse width, and/or pulse rate, the physician can attempt to generate an efficacious therapy for patient 12 that is delivered via the selected electrode subset. Due to physiological diversity, condition differences, and inaccuracies in lead placement, the parameters may greatly vary between patients.

During a programming session, the clinician may determine one or more therapy programs that may provide effective therapy to patient 12. Patient 12 may provide feedback to the clinician as to the efficacy of the specific program being evaluated. Once the clinician has identified one or more programs that may be beneficial to patient 12, patient 12 may continue the evaluation process and determine which program best alleviates the condition of patient 12 or otherwise provides efficacious therapy to patient 12. Programmer 20 may assist the clinician in the creation/identification of therapy programs by providing a methodical system of identifying potentially beneficial therapy parameters.

In some examples, the clinician may select therapy parameters using the techniques described in commonly-assigned U.S. Pat. No. 7,822,483 issued on Oct. 26, 2010 to Stone et al., entitled, "ELECTRICAL AND ACTIVATION FIELD MODELS FOR CONFIGURING STIMULATION THERAPY" and filed on Oct. 31, 2006, and commonly-assigned U.S. Patent Application Publication No. 2007/0203541 by Goetz et al., entitled, "PROGRAMMING INTERFACE WITH A CROSS-SECTIONAL VIEW OF A STIMULATION LEAD WITH COMPLEX ELECTRODE ARRAY GEOMETRY," and filed on Oct. 31, 2006. U.S. Pat. No. 7,822,483 and U.S. Patent Application Publication No. 2007/0203541 describe programming systems and methods that support the programming of stimulation parameters with a therapy system 10 including a lead 16, which may include a complex electrode array geometry.

In accordance with techniques described in U.S. Pat. No. 7,822,483 to Stone et al., a user interface of programmer 20 may display a representation of the anatomical regions of patient 12, such as anatomical regions of brain 18. The three-dimensional (3D) space of the anatomical regions may be displayed as multiple two-dimensional (2D) views or a 3D visualization environment. Lead 16 may also be represented on the display of the user interface, positioned according to the actual implantation location by the clinician or directly from an image taken of the lead within brain 18. The clinician may interact with the user interface of programmer 20 to manually select and program certain electrodes of lead 16, select an electrode level of the lead and adjust the resulting stimulation field with the anatomical regions as guides, or defining one or more stimulation fields that only affect anatomical regions of interest. Once the clinician has defined the one or more stimulation fields, system 10 automatically generates the stimulation parameter values associated with each of the stimulation fields and transmits the parameter values to IMD 14. The stimulation parameter values may be stored as therapy programs within a memory of IMD 14 and/or a memory within programmer 20.

In accordance with techniques described in U.S. Patent Publication No. 2007/0203541 by Goetz et al., programmer 20 may present a user interface that displays electrodes 17 of lead 16 and enables a user to select individual electrodes to form an electrode combination and specify parameters for stimulation delivered via the selected electrode combination. In accordance with other techniques described in U.S. Patent Publication No. 2007/0203541 by Goetz et al., programmer 20 may present a user interface to a user that enables the user to manipulate a representation of an electrical stimulation field (i.e., one type of therapy field) produced by a selected electrode combination. A processor within programmer 20 may then select the appropriate electrode combination, electrode polarities, amplitudes, pulse widths, and pulse rates of electrical stimulation sufficient to support the field manipulation operations inputted by the user into programmer 20. That is, programmer 20 may automatically generate a therapy program that best fits a stimulation field created by a user via a user interface of programmer 20.

Programmer 20 may also be configured for use by patient 12. When configured as the patient programmer, programmer 20 may have limited functionality in order to prevent patient 12 from altering critical functions or applications that may be harmful to patient 12. In this manner, programmer 20 may only allow patient 12 to adjust certain therapy parameters or set an available range of values for a particular therapy parameter. Programmer 20 may also provide an indication to patient 12 when therapy is being delivered or when IMD 14 or when the power source within programmer 20 or IMD 14 need to be replaced or recharged.

Whether programmer 20 is configured for clinician or patient use, programmer 20 may communicate with IMD 14 or any other computing device via wireless communication. Programmer 20, for example, may communicate via wireless communication with IMD 14 using radio frequency (RF) telemetry techniques known in the art. Programmer 20 may also communicate with another programmer or computing device via a wired or wireless connection using any of a variety of local wireless communication techniques, such as RF communication according to the 802.11 or Bluetooth specification sets, infrared communication according to the IRDA specification set, or other standard or proprietary telemetry protocols. Programmer 20 may also communicate with another programming or computing device via exchange of removable media, such as magnetic or optical disks, or memory cards or sticks. Further, programmer 20 may communicate with IMD 14 and other another programmer via remote telemetry techniques known in the art, communicating via a local area network (LAN), wide area network (WAN), public switched telephone network (PSTN), or cellular telephone network, for example.

In other applications of therapy system 10, the target therapy delivery site within patient 12 may be a location proximate to a spinal cord or sacral nerves (e.g., the S2, S3 or S4 sacral nerves) in patient 12 or any other suitable nerve, organ, muscle or muscle group in patient 12, which may be selected based on, for example, a patient condition. For example, therapy system 10 may be used to deliver an electrical stimulation to tissue proximate to a pudendal nerve, a perineal nerve or other areas of the nervous system, in which cases, lead 16 would be implanted and substantially fixed proximate to the respective nerve. As further examples, an electrical stimulation system may be positioned to deliver a stimulation to help manage peripheral neuropathy or post-operative pain mitigation, ilioinguinal nerve stimulation, intercostal nerve stimulation, gastric stimulation for the treatment of gastric mobility disorders and obesity, muscle stimulation, for mitigation of other peripheral and localized pain (e.g., leg pain or back pain). In addition, although a single lead 16 is shown in FIG. 1A, in some therapy systems, two or more leads may be electrically coupled to IMD 14.

Figure 1B:
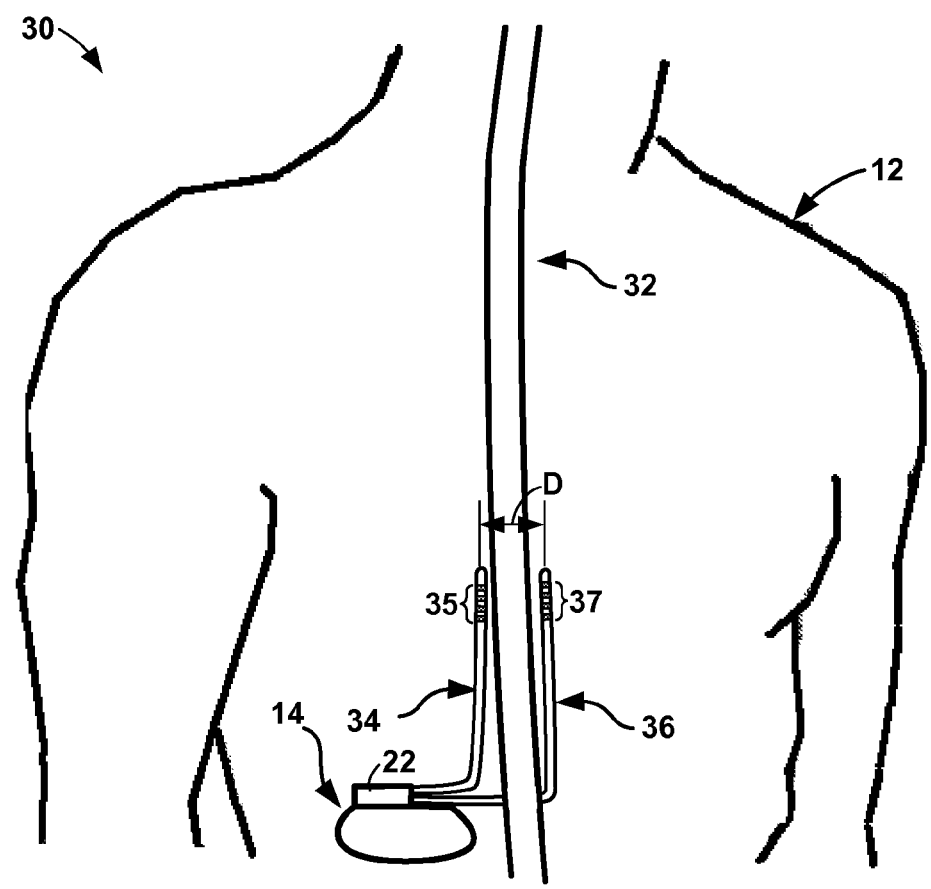

FIG. 1B is a conceptual diagram of another example of therapy system 30 that delivers electrical stimulation to target tissue sites proximate to spine 32 of patient 12. Therapy system 30 includes IMD 14, which is coupled to leads 34, 36 via connector 22. Leads 34, 36 each include an array of electrodes 35, 37, respectively. IMD 14 may deliver stimulation to patient 12 via a combination of electrodes 35, 37. Electrodes 35, 37 may each be any suitable type of electrode, such as a ring electrode, partial ring electrode or segmented electrode.

In some examples, the array of electrodes 35, 37, as well as electrodes 17 of therapy system 10 (FIG. 1A), may also include at least one sense electrode that senses a physiological parameter of patient 12, such as, but not limited to, a heart rate, respiration rate, respiratory volume, core temperature, muscular activity, electromyogram (EMG), an electroencephalogram (EEG), an electrocardiogram (ECG) or galvanic skin response. Therapy systems 10, 30 may also include sensor 26 (shown in FIG. 1A) in addition to or instead of sense electrodes on the leads 16, 34, 36. Sensor 26 may be a sensor configured to detect an activity level, posture, or another physiological parameter of patient 12. For example, sensor 26 may generate a signal that changes as a function of the physiological parameter of patient 12. Sensor 26 may be implanted or external to patient 12, and may be wirelessly coupled to IMD 14 or via a lead, such as leads 16, 34, 36, or another lead. For example, sensor 26 may be implanted within patient 12 at a different site than IMD 14 or sensor 26 may be external to patient 12. In some examples, sensor 26 may be incorporated into a common housing with IMD 14. In addition or instead of being coupled to IMD 14, in some cases, sensor 26 may be wirelessly coupled to programmer 20 or coupled to programmer 20 by a wired connection.

In the example shown in FIG. 1B, leads 34, 36 are positioned to deliver bilateral stimulation to patient 12, i.e., stimulation signals are delivered to target tissue sites on opposite sides of a midline of patient 12. The midline may generally be defined along spinal cord 32. Just as with therapy system 10, a clinician may generate one or more therapy programs for therapy system 30 by selecting values for one or more types of therapy parameters that provide efficacious therapy to patient 12 with the aid of programmer 20 or another computing device. The therapy parameters may include, for example, a combination of the electrodes of leads 34 and/or 36, the voltage or current amplitude, pulse width, and frequency of stimulation.

For therapy system 10 (FIG. 1A), therapy system 30 (FIG. 1B) or any other therapy system that provides therapy to patient 12, an algorithmic model of a therapy field (also referred to as a "therapy field model") may be generated with the aid of modeling software, hardware or firmware executing on a computing device, such as programmer 20 or a separate dedicated or multifunction computing device. The therapy field model may be based on a therapy program defining respective values for one or more therapy parameters and may represent where therapy will propagate from a therapy system (e.g., leads 16, 34 or 36) delivering therapy according to the therapy program. The therapy field model may be useful for guiding the modification of the therapy parameter values of the therapy program. For example, the therapy field model may be compared to a reference therapy field and one or more of the therapy parameter values defined by the therapy program may be modified based on the comparison. Additionally or alternatively, the therapy field model may be used to adjust therapy parameter values to increase an operating efficiency of the therapy system while substantially maintaining at least one field characteristic of the therapy field model.

The therapy field model may be stored within a memory of programmer 20, IMD 14 or another device. While the remainder of the description of FIGS. 2-5 primarily refers to therapy system 30 of FIG. 1B, in other examples, the techniques for generating an algorithmic model of a therapy field may be applied to therapy system 10 of FIG. 1A that provides DBS to patient 12. In addition, while the remainder of the description primarily refers to an algorithmic model of a therapy field that is generated with the aid of modeling software executing on a computing device, in other examples, the algorithmic model of a therapy field may be generated with the aid of hardware or firmware in addition to or instead of software.

In some examples, the modeling software implements an algorithm that models the therapy field based on a therapy program, an anatomy of patient 12, and the hardware characteristics of therapy system 10 or therapy system 30. In the case of therapy system 30 (FIG. 1B), the hardware characteristics may include the type of IMD 14, which may include the energy threshold for the particular type of IMD 14, the type of leads 34, 36, which may include the type of electrodes 35, 37 (e.g., ring electrodes, partial ring electrodes or segmented electrodes), and a baseline impedance presented to IMD 14 at the time of programming, i.e., the impedance of the entire path between IMD 14 and the target tissue site, including the lead conductors, electrodes 35, 37, and patient tissue through which stimulation propagates. In examples in which a therapy system includes two or more leads 34, 36, the hardware characteristics of therapy system 30 may include a baseline distance between the electrodes 35, 37 of the respective leads 34, 36. The baseline spacing between electrodes 35, 37 of leads 34, 36 may be, for example, the spacing between electrodes 35, 37 at the time of implant of leads 34, 36. The algorithm for generating the therapy field model may be stored within a memory of programmer 20, IMD 14 or another device.

In examples in which a clinician generates therapy programs for IMD 14 by selecting a stimulation field and subsequently generating the stimulation parameter values that may achieve the stimulation field, the therapy field may be an algorithmic model of the stimulation field selected by the clinician. For example, the therapy field may be an electrical field model that is generated based upon a patient anatomy data and a therapy program defining stimulation parameter values, where the electrical field model represents the areas of a patient anatomical region that will be covered by an electrical field during therapy delivery. The patient anatomy data may be specific to patient 12 or may represent data for more than one patient, e.g., model or averaged data of the anatomical structure and tissue conductivity of multiple patients. With respect to therapy system 30 of FIG. 1B, the electrical field model represents where electrical stimulation propagates through tissue from electrodes 35, 37 of leads 34, 36. Patient anatomy data may indicate one or more characteristics of patient tissue (e.g., impedance) proximate to implanted leads 34, 36, and may be created from any type of imaging modality, such as, but not limited to, computed tomography (CT), magnetic resonance imaging (MRI), x-ray, fluoroscopy, and the like.

In other examples, the therapy field may be an activation field model that may be based on a neuron model that indicates one or more characteristics of patient neural tissue proximate to electrodes 35, 37 of implanted leads 34, 36, respectively. The activation field may indicate the neurons that will be activated by the electrical field in the anatomical region. The clinician may program the therapy parameter values for one or more therapy programs for guiding the therapy delivery by IMD 14 by selecting a desired therapy field and generating therapy parameter values that may achieve the desired therapy field, taking into consideration the patient's anatomy and the hardware characteristics of therapy system 30. As previously indicated, the hardware characteristics may include the type of IMD 14, the type of leads 34, 36, the type of electrodes 35, 37, and the spacing between the leads 34, 36 and/or electrodes 35, 37 within patient 12.

In other examples, an algorithmic model of the therapy field may be generated after selecting a therapy program. For example, the clinician may select therapy parameter values that provide efficacious therapy to patient 12 and generate the therapy field resulting from the therapy parameter values with the aid of modeling software executing on a computing device, such as programmer 20 or a separate workstation or computing device. Again, the resulting therapy field may be based on an algorithmic model that takes into consideration the therapy parameter values of the therapy program, the patient's anatomy, and the hardware characteristics of therapy system 30.

Figure 2:
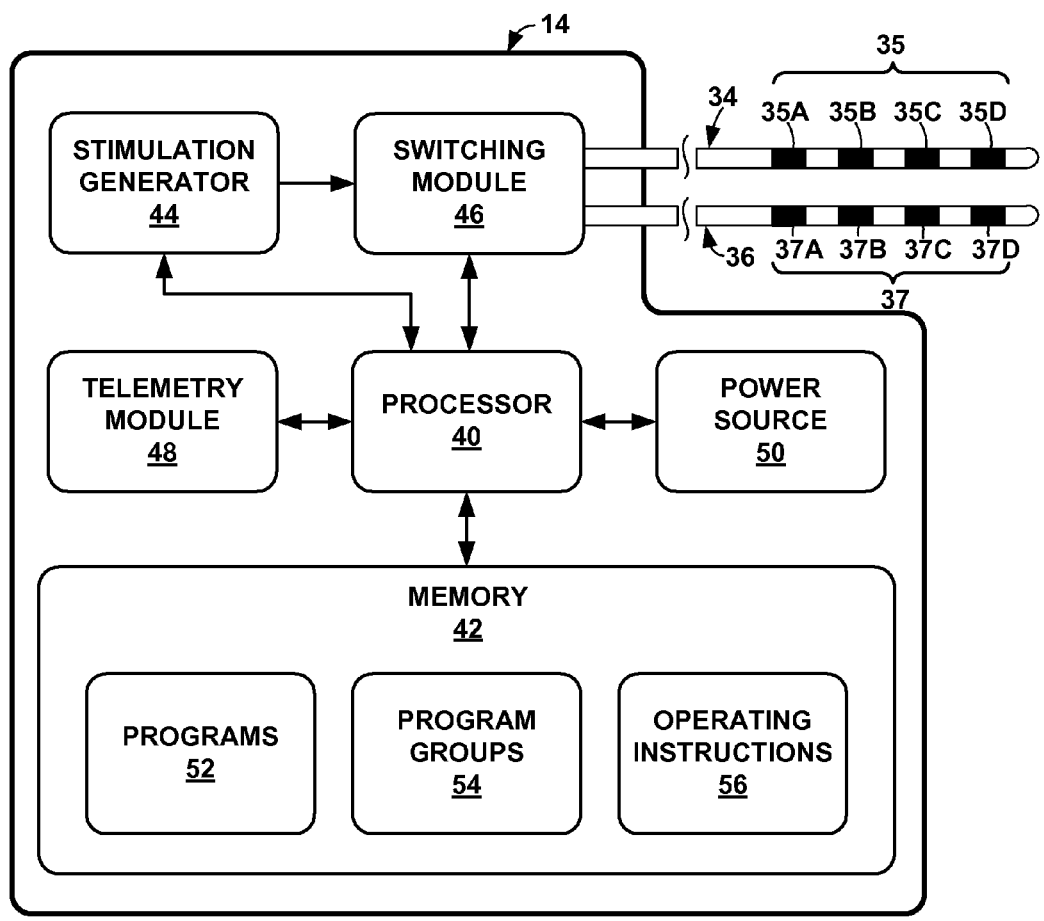
FIG. 2 is a functional block diagram of an example implantable medical device that generates electrical stimulation signals.

FIG. 2 is a functional block diagram of an example IMD 14. IMD 14 includes a processor 40, memory 42, stimulation generator 44, switching module 46, telemetry module 48, and power source 50. As shown in FIG. 2, stimulation generator 44 is coupled to leads 34, 36. Alternatively, stimulation generator 44 may be coupled to a single lead (e.g., as shown in FIG. 1A) or more than three leads directly or indirectly (e.g., via a lead extension, such as a bifurcating lead extension that may electrically and mechanically couple to two leads) as needed to provide stimulation therapy to patient 12.

In the example illustrated in FIG. 2, lead 34 includes electrodes 35A-35D (collectively referred to as "electrodes 35") and lead 36 includes electrodes 37A-37D (collectively referred to as "electrodes 37"). Electrodes 35, 37 may be ring electrodes. In other examples, electrodes 35, 37 may be arranged in a complex electrode array that includes multiple non-contiguous electrodes at different angular positions about the outer circumference of the respective lead 34, 36, as well as different levels of electrodes spaced along a longitudinal axis of the respective lead 34, 36. The configuration, type, and number of electrodes 35, 37 illustrated in FIG. 2 are merely exemplary. In other examples, IMD 14 may be coupled to any suitable number of leads with any suitable number and configuration of electrodes.

Memory 42 includes computer-readable instructions that, when executed by processor 40, cause IMD 14 to perform various functions. Memory 42 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 42 may include programs 52, program groups 54, and operating instructions 56 in separate memories within memory 42 or separate areas within memory 42. Each program 52 defines a particular program of therapy in terms of respective values for electrical stimulation parameters, such as electrode combination, electrode polarity, current or voltage amplitude, pulse width and pulse rate. A program group 54 defines a group of programs that may be delivered together on an overlapping or non-overlapping basis. Operating instructions 56 guide general operation of IMD 14 under control of processor 40, and may include instructions for measuring the impedance of electrodes 35, 37 and/or determining the distance between electrodes 35, 37.

Stimulation generator 44 produces stimulation signals, which may be pulses as primarily described herein, or continuous time signals, such as sine waves, for delivery to patient 12 via selected combinations of electrodes 35, 37. Processor 40 controls stimulation generator 44 according to programs 52 and program groups 54 stored by memory 42 to apply particular stimulation parameter values specified by one or more of programs, such as amplitude, pulse width, and pulse rate. Processor 40 may include any one or more microprocessors, controllers, digital signal processors (DSPs), application specific integrated circuits (ASICs), field-programmable gate arrays (FPGAs), or equivalent discrete or integrated digital or analog logic circuitry, and the functions attributed to processor 40 herein may be embodied as software, firmware, hardware or any combination thereof.

Processor 40 also controls switching module 46 to apply the stimulation signals generated by stimulation generator 44 to selected combinations of electrodes 35, 37. In particular, switching module 46 couples stimulation signals to selected conductors within leads 34, 36 which, in turn, deliver the stimulation signals across selected electrodes 35, 37. Switching module 46 may be a switch array, switch matrix, multiplexer, or any other type of switching device suitable to selectively couple stimulation energy to selected electrodes. Hence, stimulation generator 44 is coupled to electrodes 35, 37 via switching module 46 and conductors within leads 34, 36. In some examples, IMD 14 does not include switching module 46.

Stimulation generator 44 may be a single or multi-channel stimulation generator. In particular, stimulation generator 44 may be capable of delivering, a single stimulation pulse, multiple stimulation pulses, or a continuous signal at a given time via a single electrode combination or multiple stimulation pulses at a given time via multiple electrode combinations. In some examples, however, stimulation generator 44 and switching module 46 may be configured to deliver multiple channels on a time-interleaved basis. In this case, switching module 46 serves to time division multiplex the output of stimulation generator 44 across different electrode combinations at different times to deliver multiple programs or channels of stimulation energy to patient 12.

Telemetry module 48 supports wireless communication between IMD 14 and an external programmer 20 or another computing device under the control of processor 40. Processor 40 of IMD 14 may receive, as updates to programs, values for various stimulation parameters such as amplitude and electrode combination, from programmer 20 via telemetry interface 48. The updates to the therapy programs may be stored within programs 52 portion of memory 42.

The various components of IMD 14 are coupled to power supply 50, which may include a rechargeable or non-rechargeable battery. A non-rechargeable battery may be selected to last for several years, while a rechargeable battery may be inductively charged from an external device, e.g., on a daily or weekly basis. In other examples, power supply 50 may be powered by proximal inductive interaction with an external power supply carried by patient 12.

Figure 3:
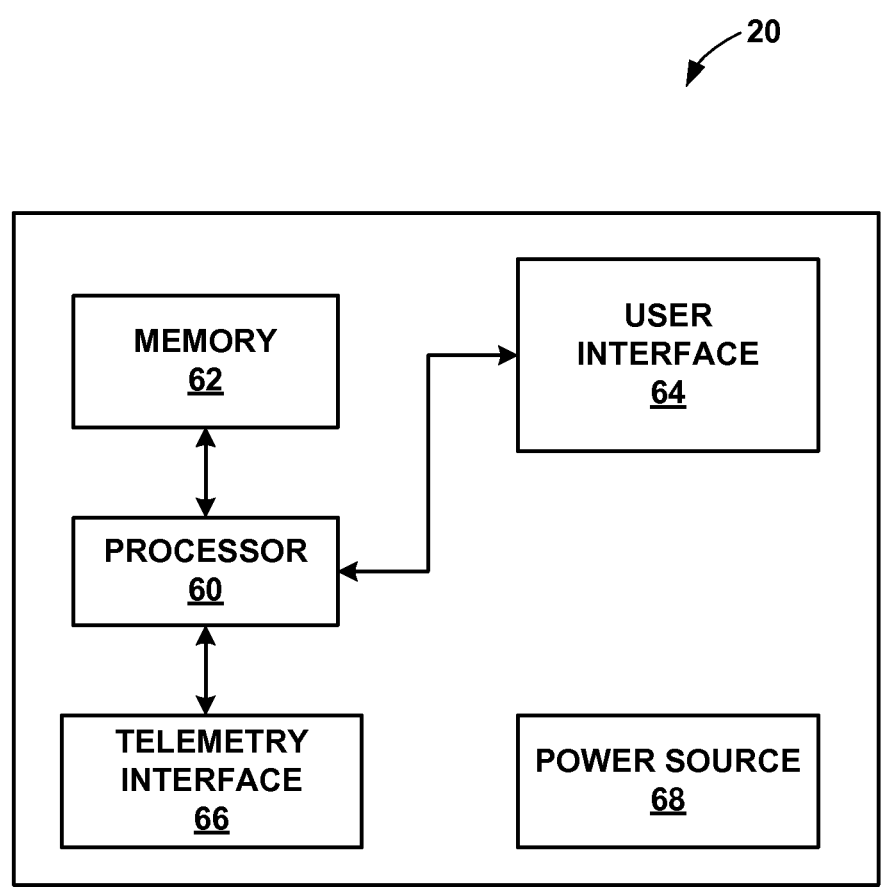
FIG. 3 is a functional block diagram of an example medical device programmer.

FIG. 3 is a functional block diagram of an example of programmer 20. As shown in FIG. 3, external programmer 20 includes processor 60, memory 62, user interface 64, telemetry module 66, and power source 68. A clinician or another user may interact with programmer 20 to generate and/or select therapy programs for delivery in IMD 14. For example, in some examples, programmer 20 may allow a clinician to define stimulation fields and generate appropriate stimulation parameter values. Programmer 20 may be used to present anatomical regions to the user via user interface 64, select therapy programs, generate new therapy programs by manipulating stimulation fields, and transmit the new therapy programs to IMD 14, as described in U.S. Pat. No. 7,822,483 issued on Oct. 26, 2010 to Stone et al. and entitled, "ELECTRICAL AND ACTIVATION FIELD MODELS FOR CONFIGURING STIMULATION THERAPY." Processor 60 may store stimulation parameter values as one or more therapy programs in memory 62. Processor 60 may send programs to IMD 14 via telemetry module 66 to control stimulation automatically and/or as directed by the user.

As previously described, programmer 20 may be a handheld computing device, a workstation or another dedicated or multifunction computing device. For example, programmer 20 may be a general purpose computing device (e.g., a personal computer, personal digital assistant (PDA), cell phone, and so forth) or may be a computing device dedicated to programming IMD 14. Programmer 20 may be one of a clinician programmer or a patient programmer in some examples, i.e., the programmer may be configured for use depending on the intended user. A clinician programmer may include more functionality than the patient programmer. For example, a clinician programmer may include a more featured user interface that allows a clinician to download usage and status information from IMD 14, and allows the clinician to control aspects of IMD 14 not accessible by a patient programmer example of programmer 20.

A user, either a clinician or patient 12, may interact with processor 60 through user interface 64. User interface 64 may include a display, such as a liquid crystal display (LCD), light-emitting diode (LED) display, or other screen, to present information related to stimulation therapy, and buttons or a pad to provide input to programmer 20. In examples where user interface 64 requires a 3D environment, the user interface may support 3D environments such as a holographic display, a stereoscopic display, an autostereoscopic display, a head-mounted 3D display, or any other display that is capable of presenting a 3D image to the user. Buttons of user interface 64 may include an on/off switch, plus and minus buttons to zoom in or out or navigate through options, a select button to pick or store an input, and pointing device, e.g. a mouse, trackball, or stylus. Other input devices may be a wheel to scroll through options or a touch pad to move a pointing device on the display. In some examples, the display may be a touch screen that enables the user to select options directly from the display screen.

Processor 60 processes instructions from memory 62 and may store user input received through user interface 64 into the memory when appropriate for the current therapy. In addition, processor 60 provides and supports any of the functionality described herein with respect to each example of user interface 64. Processor 60 may comprise any one or more of a microprocessor, DSP, ASIC, FPGA, or other digital logic circuitry, and the functions attributed to processor 60 herein may be embodied as software, firmware, hardware or any combination thereof.

Memory 62 may include any one or more of a RAM, ROM, EEPROM, flash memory, or the like. Memory 62 may include instructions for operating user interface 64, telemetry module 66, and managing power source 68.

Memory 62 may store program instructions that, when executed by processor 60, cause the processor and programmer 20 to provide the functionality ascribed to them herein. Memory 62 also includes instructions for generating therapy programs, such as instructions for determining stimulation parameters for achieving a user-selected stimulation fields or instructions for determining a resulting stimulation field from user-selected stimulation parameters. Memory 62 may also include a removable memory portion that may be used to provide memory updates or increases in memory capacities. A removable memory may also allow patient data to be easily transferred to another computing device, or to be removed before programmer 20 is used to program therapy for another patient.

Programmer 20 may communicate wirelessly with IMD 14 or another device, such as using RF communication or proximal inductive interaction. This wireless communication is possible through the use of telemetry module 66, which may be coupled to an internal antenna or an external antenna. An external antenna that is coupled to programmer 24 may correspond to the programming head that may be placed over the patient's skin near the implanted IMD 14.

Telemetry module 66 may also be configured to communicate with another computing device via wireless communication techniques, or direct communication through a wired connection. Accordingly, telemetry module 66 may include circuitry known in the art for such communication. Examples of local wireless communication techniques that may be employed to facilitate communication between programmer 20 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 20 without needing to establish a secure wireless connection.

Power source 68 delivers operating power to the components of programmer 20. Power source 68 may include a battery and a power generation circuit to produce the operating power. In some examples, the battery may be rechargeable to allow extended operation. Recharging may be accomplished through proximal inductive interaction, or electrical contact with circuitry of a base or recharging station. In other examples, primary batteries (e.g., nickel cadmium or lithium ion batteries) may be used. In addition, programmer 20 may be directly coupled to an alternating current source, such would be the case with some computing devices, such as personal computers. Power source 68 may include circuitry to monitor power remaining within a battery. In this manner, user interface 64 may provide a current battery level indicator or low battery level indicator when the battery needs to be replaced or recharged. In some cases, power source 68 may be capable of estimating the remaining time of operation using the current battery.

FIGS. 4A-4C and 5 are flowcharts illustrating example techniques for modifying values for one or more types of therapy parameters of a therapy program based on an algorithmic model of a therapy field. While the therapy parameter modification techniques shown in FIGS. 4A-4C and 5 are described as being performed by programmer 20, in other examples, processor 40 (FIG. 2) of IMD 14 or a processor of another computing device, such as a clinician workstation, or any combination of devices may execute the techniques for modifying therapy parameters shown in FIGS. 4A-4C and 5.

Figure 4A:
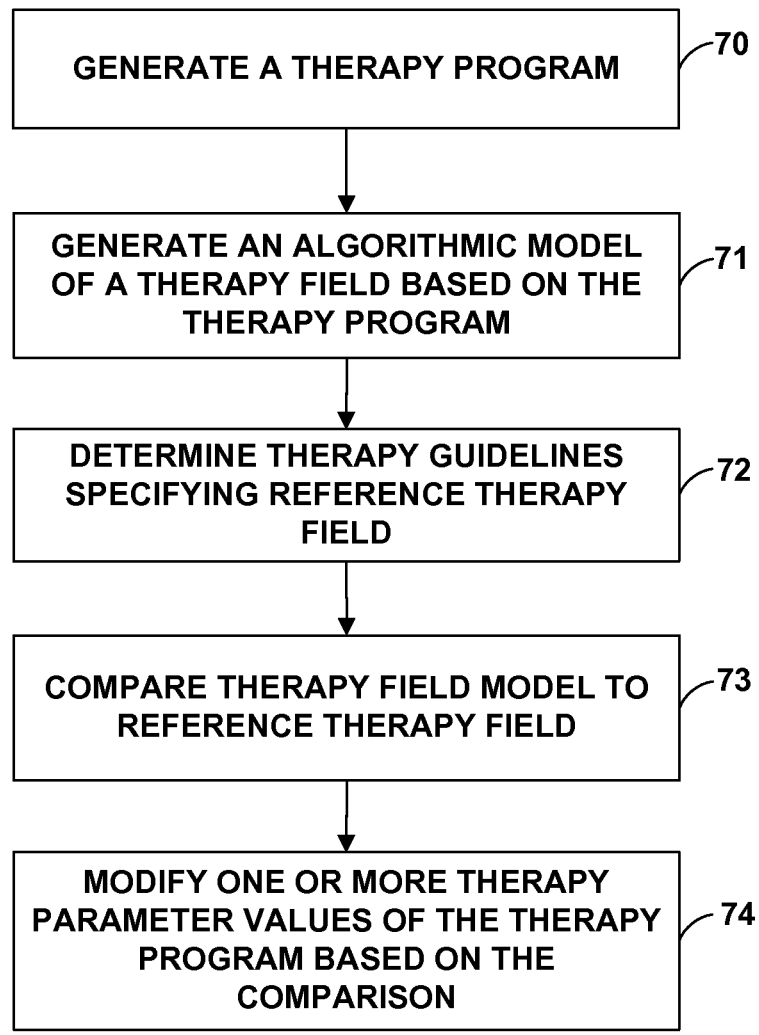
FIGS. 4A-4C are flow diagrams illustrating example techniques for modifying therapy parameters based on an algorithmic model of a therapy field.

As illustrated in FIG. 4A, programmer 20 generates a therapy program to control therapy delivery to patient 12 by IMD 14 (70). In some examples, programmer 20 may facilitate evaluation of one or more therapy parameter values in order to generate the therapy program. For example, memory 62 of programmer 20 may store an evaluation sequence that guides the user in the selection of electrode combinations and stimulation parameter values, or automatically selects electrode combinations and stimulation parameter values for evaluation of efficacy. For example, the evaluation sequence may specify a predetermined progression of electrode combinations to be selected for evaluation, or provide rules for dynamic selection of electrode combinations during the course of evaluation.

Memory 62 also may record efficacy information associated with one or more of the tested programs. Specifically, upon selection of an electrode combination and stimulation parameters as a program, programmer 20 may direct IMD 14 to apply the program. Upon application of the program, the patient may provide feedback concerning efficacy. The user, which may be a clinician or the patient 12, then records the efficacy information in memory 62 of programmer 20. In this manner, different programs may be rated in terms of efficacy so that the user ultimately may select an effective electrode combination and stimulation parameters.

After determining a therapy program for patient 12 (70), processor 60 may generate an algorithmic model of a therapy field for the selected therapy program, e.g., a therapy program that, based on the rating information, provides efficacious therapy to patient 12 (71). The algorithmic model of the therapy field represents where therapy will propagate from therapy system 30 when IMD 14 is delivering therapy to patient 12 according to the selected therapy program. Electrical stimulation delivered by IMD 14 generates a therapy field within patient 12. For example, the therapy field may be an electrical field that indicates areas of the patient's tissue that are covered by an electrical field emanating from electrodes 35, 37 of leads 34, 36 during therapy delivery. As another example, the therapy field may indicate an activation field that indicates the neurons that are activated by the electrical field. Accordingly, in some examples, the therapy field model may represent the electrical field or the activation field resulting from therapy delivery by therapy system 30 according to the selected therapy program.

The therapy field model may vary depending upon the therapy parameter values of the selected therapy program and the patient anatomy proximate to the target tissue site for the electrical stimulation. For example, depending on the target tissue site for stimulation, an electrical field resulting from stimulation therapy delivered according to a particular therapy program may have a different stimulation area, a different centroid of stimulation, or different activated neurons. As one example, the type of neurons activated may depend upon the patient anatomy proximate to the target tissue site for the stimulation, and the stimulation parameter values may be configured to target neurons less than a maximum diameter. The algorithm implemented by processor 60 to generate the therapy field model, therefore, considers the therapy parameter values of the selected therapy program, the anatomy of patient 12 proximate to the target stimulation site, and the hardware characteristics of therapy system 30. In general, the electrical field model or the activation field model may estimate the anatomical structures that will be affected by a therapy program.

Processor 60 determines therapy guidelines based on the patient condition (72). In one example, the therapy guidelines comprise a reference therapy field that is specific to a patient condition. The reference therapy field may be a therapy field that is believed to provide efficacious therapy to manage the patient's condition, and may be, but need not be, specific to the particular patient 12. In other examples, the reference therapy field may merely be a starting point for generating a therapy program for patient 12.

The therapy guidelines may provide guidelines for generating an efficacious therapy program for a particular patient within a patient class characterized by a common patient condition. For example, the reference therapy field may define one or more field characteristics that the clinician may use as reference points for achieving a particular functional outcome for the therapy delivery to patient 12. The field characteristics of a therapy field may include, but are not limited to, centroids of stimulation, the total volume of the electrical field or activation field (or the total area with respect to a cross-section of the therapy field), the regions of the patient anatomy recruited or otherwise covered by the therapy field, a charge density or an amplitude of the voltage or current at a certain point within the stimulation therapy field, e.g., whether the voltage or current amplitude at a certain point within the stimulation therapy field exceeds the activation energy of the neurons. Functional outcomes may include, for example, mitigation of one or more symptoms associated with the patient's condition. In the case of a seizure disorder, the functional outcomes may include the minimization of the frequency, severity, and/or duration of seizures. In the case of movement disorders, the functional outcomes may include an improvement in the patient's gait and mobility.

In addition to including one or more reference therapy fields, the therapy guidelines may identify anatomical structures or target tissue sites within brain 18 (FIG. 1A) that may be activated by an electrical field in order to effectively manage the patient's condition. For example, the therapy guidelines may identify the Substantia Nigra in brain 18 as a useful target tissue site for electrical stimulation therapy in order to reduce the number and magnitude of tremors experienced by patient 12. As another example, the therapy guidelines may identify the anterior thalamus, ventrolateral thalamus, globus pallidus, substantia nigra pars reticulata, subthalamic nucleus, neostriatum, cingulated gyms or the cingulate gyms as target tissue sites within brain 18 for managing a seizure disorder of patient 12.

In other examples, the therapy guidelines may provide information that guides the programming of IMD 14 for other therapeutic applications. For example, with respect to therapy system 10 that provides spinal cord stimulation (SCS) to patient 12, the therapy guidelines may identify a particular target tissue site proximate to a particular vertebra of spinal cord 32 (FIG. 1B) for managing pain in a particular area, such as a particular class of back pain. As another example, if IMD 14 is used to provide electrical stimulation therapy for managing urinary or fecal incontinence of patient 12, the therapy guidelines may identify the relevant nerve (e.g., a sacral nerve or pudendal nerve or nerve branch) or muscle for stimulating.

The therapy guidelines may be determined based on the results of clinical studies, computer modeling or both. The therapy guidelines may be stored within memory 62 of programmer 20, memory 42 of IMD 14, or a memory of another computing device. In some examples, a clinician or other user may upload the therapy guidelines into programmer 20 from a separate computing device via telemetry interface 66. For example, a clinician may access a database of therapy guidelines with a computer workstation, and, based on the symptoms of patient 12, select the appropriate therapy guidelines from the database and upload the selected therapy guidelines to programmer 20.

Processor 60 may compare the therapy field model to the reference therapy field (73). In one example, processor 60 compares at least one field characteristic of the modeled therapy field to a respective characteristic of the reference therapy field. The one or more compared field characteristics may be selected based on the characteristics of the therapy field that may affect the efficacy of therapy. In addition, the field characteristics may be weighted based on their impact on the efficacy of therapy, and the comparison between the algorithmic models of the original therapy field and the adjusted therapy field may be made on the weighted field characteristics.

In the case of DBS delivered by therapy system 10 (FIG. 1A), the regions of the patient anatomy recruited or otherwise covered by the therapy field may affect the efficacy of therapy more than the total volume of the electrical field or activation field. Thus, processor 60 may compare the regions of patient anatomy recruited or otherwise covered by the therapy field model that was generated based on the therapy program with the regions of patient anatomy recruited or otherwise covered by the reference therapy field in order to determine whether to modify the therapy program. However, in some cases, processor 60 may compare both the regions of patient anatomy recruited by the modeled therapy field as well as the total volumes of the electrical field or activation field with the respective characteristics of the reference therapy field.

In the case of SCS delivered by therapy system 30 (FIG. 1B), the centroid of stimulation may affect the efficacy of therapy more than the total volume of the electrical field or activation field. Thus, processor 60 may compare the centroid of stimulation of the therapy field model based on the therapy program with the centroid of stimulation of the reference therapy field in order to determine whether to modify the therapy program. Again, processor 60 may compare more than one field characteristics of the current therapy field with the reference therapy field.

In some examples, processor 60 computes one or more metrics that indicate the similarity between the therapy field model that was generated based on the therapy program and the reference field defined by the therapy guidelines. As one example, processor 60 may determine the ratio of the volume of the reference therapy field to the volume of the therapy field model. Other metrics may include the percentage of overlap between the reference field and the therapy field model, or the total volume of the therapy field model that does or does not overlap the reference field.

In some examples, processor 60 presents the therapy field model generated based on the therapy program and the reference therapy field of the therapy guidelines on the display of user interface 64 of programmer 20. For example, as will be described in further detail below, the modeled and reference therapy fields may be overlaid on a representation of the target anatomical region of patient 12 for the therapy delivery. A user may visually or otherwise compare the displayed fields and provide feedback to processor 60 via user interface 64.

Based on the comparison between the therapy field model and the reference field, processor 60 may adjust one or more therapy parameter values, e.g., respective values for the pulse width, frequency or amplitude defined by the therapy program (74). For example, if the volume of the therapy field model is substantially larger than the volume of the reference therapy field, the clinician or another user of programmer 20 may adjust one or more therapy parameter values to generate a smaller therapy field. Processor 60 may suggest a parameter adjustment to a user via user interface 64 or automatically adjust one or more therapy parameters based on the calculated metrics. Memory 62 of programmer 20 may include, for example, a set of therapy parameter value modification rules that enables processor 60 determine how the therapy field may be modified (e.g., decreased in volume). In some examples, processor 60 compares a metric indicative of the ratio between the volume of the therapy field model generated based on the therapy program and the volume of the reference field to a threshold value and adjusts the therapy program based on the comparison. Memory 62 may store the metric values determined by processor 60 based on the comparison between the therapy field model and the reference field, as well as any relevant threshold values and rules for therapy program modification.

In some examples, after processor 60 modifies the therapy program, processor 60 may generate an algorithmic model of the modified therapy field ("modified therapy field model") resulting from therapy delivery by therapy system 10 according to the modified therapy program defining the adjusted set of therapy parameter values. The algorithmic model of the modified therapy field may be generated using the same or a different algorithm that is used to generate the algorithmic model of the therapy field resulting from therapy delivery according to the therapy program. In some examples, the modified therapy field model produced by the adjusted set of therapy parameter values may more closely resemble the reference field. If the first therapy field model based on the first therapy program has a volume substantially larger than the reference therapy field, the modified therapy field that is based on the modified therapy program may be have a smaller volume than the first therapy field model, which may be closer to the volume to the reference field than the first therapy field model. An algorithmic model of a therapy field with a volume substantially larger than the reference field may indicate that the stimulation energy used to provide stimulation therapy to patient 12 is higher than necessary to manage the patient condition, which may result in wasted energy and potentially cause long term nerve damage. Decreasing the volume of the therapy field model may help minimize the stimulation energy that is required to provide the stimulation therapy to patient 12. In this way, the modification to the therapy program may promote long-term therapeutic outcomes and patient comfort by increasing the useful life of IMD 14 and its power source 50 (FIG. 2).

After processor 60 modifies the therapy program and generates an algorithmic model of the modified therapy field based on the modified therapy program, processor 60 may perform an additional comparison between the modified therapy field and the reference field to determine if further modification to the modified therapy program is desirable. For example, processor 60 may compare the algorithmic model of the modified therapy field to the reference therapy field (73) and adjust therapy parameter values based on the comparison (74).

In some examples, rather than generating a therapy program (70), processor 60 of programmer 20 may merely select a therapy program from memory 62 of programmer 20 or memory 42 (FIG. 2) of IMD 14. The therapy program may be, for example, identified as being a potentially efficacious therapy program for patient 12 during a prior programming session. As another example, processor 60 may select a therapy program that has been identified as being a potentially efficacious therapy program for a class of patients having the same patient condition as patient 12.

Figure 4B:
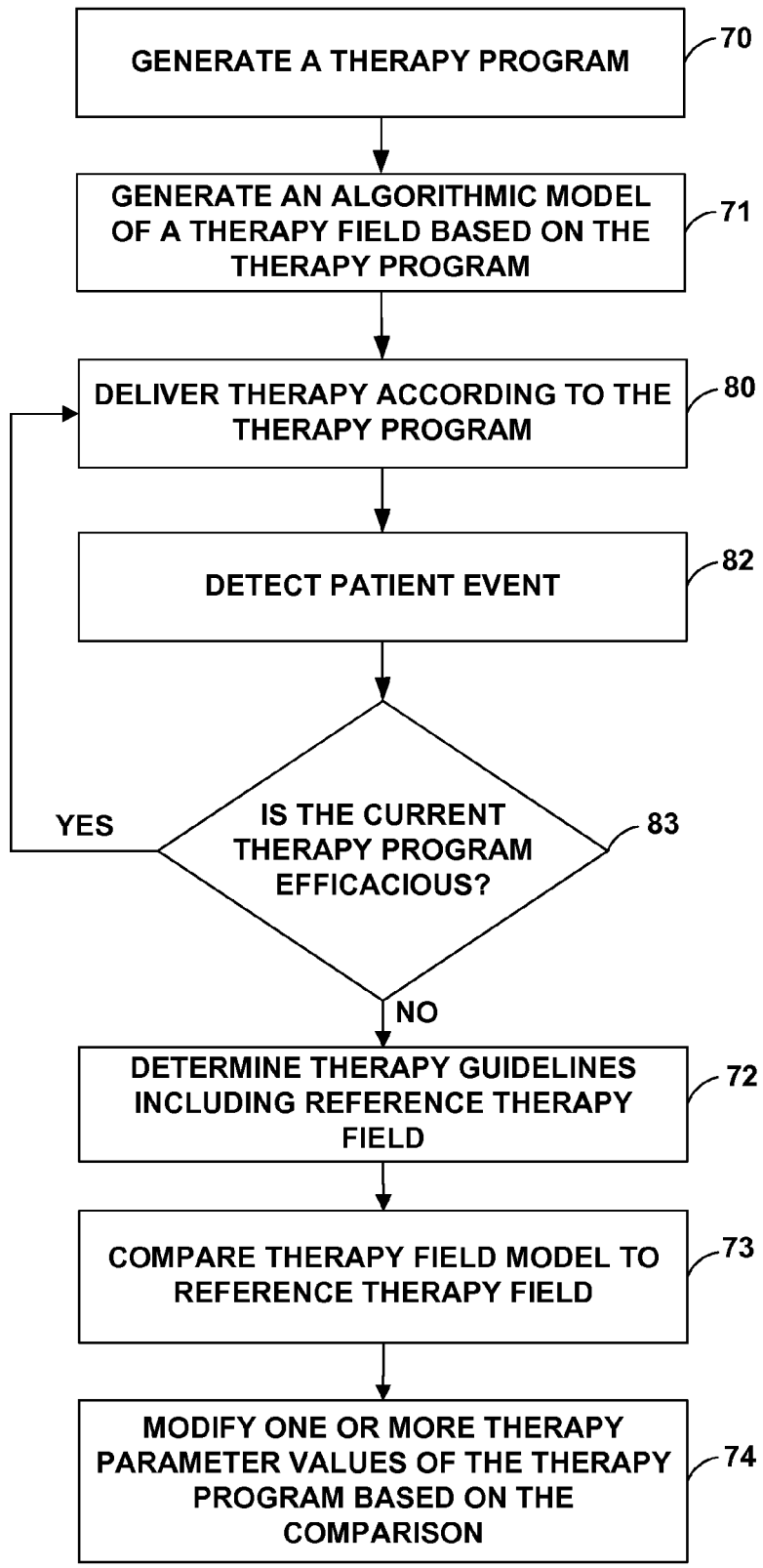

FIG. 4B illustrates another example of a technique for modifying a therapy program based on an algorithmic model of a therapy field and therapy guidelines. The technique outlined in FIG. 4B is similar to the method outlined in FIG. 4A. However, in the example technique illustrated in FIG. 4B, the determination of the therapy guidelines is based on one or more patient events that are detected when therapy is delivered to patient 12 using the therapy program.

As described with respect to FIG. 4A, processor 60 of programmer 20 may generate or select a therapy program (70) and generate an algorithmic model of a therapy field based on the therapy program (71). Additionally, processor 60 may control IMD 14 to deliver therapy to patient 12 according to the therapy program (80). During therapy delivery, processor 60 may monitor one or more physiological parameters of patient 12 based on signals from one or more sensors 26 (FIG. 1A) in order to detect one or more patient events based on the signals (82). Patient events may, for example, reflect the occurrence of patient symptoms associated with the patient condition for which therapy systems 10, 30 are implemented to manage or side effects from the therapy delivery.

If the stimulation intensity is too low, the patient may experience symptoms associated with the patient condition for which therapy systems 10, 30 are implemented to manage. If the stimulation intensity is too high, the patient may experience side effects, such as pain. The detection of patient events may indicate that therapy delivery according to the current therapy program is not providing efficacious treatment of the patient condition, e.g., because the events may indicate undesirable the patient symptoms or side effects. Processor 60 may determine whether the current therapy program is providing efficacious therapy to patient 12 based on the detected patient events (83).

In some examples, patient 12 may provide feedback, e.g., via programmer 20, relating to the occurrence of a patient event. Feedback from patient 12 may be useful if sensor 26 does not detect the patient event and/or the feedback is a subjective assessment provided by patient 12. For example, in one example, programmer 20 includes a dedicated button or another user input mechanism that patient 12 may press or otherwise interact with each time a particular patient event occurs, such as a seizure, a pain level above a particular threshold (which may be subjectively assessed by patient 12), an incontinence event, an uncomfortable response to stimulation, or a stimulation signal that covers a non-target region. The patient event may be selected to be a symptom of the patient condition for which the therapy system is used to treat or a side effect of the electrical stimulation therapy. Processor 60 may store an indication, such as a flag, value or signal, upon activation of the event button (or other input mechanism). Upon reaching a threshold number within a particular time frame (e.g., an hour, days, weeks or months), processor 60 may evaluate the therapy program due to the detected patient events.

Instead of or in addition to patient input to provide information relating to the occurrence of patient events during therapy delivery according to the current therapy program, information from sensors may provide information regarding the occurrence of patient events. As discussed above, therapy systems 10, 30 may include one or more sensors, such as sensor 26 or a sensor on IMD 14 housing or coupled to leads 16, 34, 36, which may monitor a patient parameter that changes in response to the efficacy of therapy, such as in response to an increase in patient symptoms or an increase in patient side effects. For example, if therapy system 10 delivers therapy to manage a seizure disorder of patient 12, sensor 26 may include an accelerometer (e.g., one or more one, two or three axis accelerometers), a bonded piezoelectric crystal, a mercury switch, or a gyro to monitor patient activity level to detect the occurrence of a seizure, e.g., by detecting the abnormal body movements. In yet another example, sensor 26 may monitor a heart rate of patient 12, and a change in heart rate may indicate an onset of a seizure.

Sensing electrodes on leads 16, 34, 36 may also be used to detect the occurrence of a seizure, e.g., based on EEG or ECoG signals or other brain signals. Processor 60 of programmer 20 may receive the signals from the sensing electrodes or sensor 26 and determine whether the signals indicate the occurrence of a seizure. For example, processor 60 may compare the EEG or ECoG waveform to a threshold amplitude value that indicates a seizure occurred, or processor 60 may perform a temporal correlation or frequency correlation with a template signal, or combinations thereof in order to determine whether a seizure has occurred. Alternatively, processor 40 of IMD 14 may determine whether a seizure occurred and transmit an indication, such as a flag, value or other marker, to programmer 20. In general, for each example described herein, processor 40 of IMD 14 may detect a patient event and transmit an indication to programmer 20.

Processor 60 may record each seizure occurrence, and upon reaching a threshold number of seizures within a particular time frame (e.g., an hour, days, weeks or months) or a particular pattern of seizures, processor 60 may determine that the therapy is not substantially effective due to the increase in the number of seizures experienced by patient 12. Thus, a certain number of seizure events may prompt processor 60 to evaluate the current therapy field.

In examples in which therapy system 10 (FIG. 1A) provides DBS to manage a movement or mood disorder (e.g., a psychiatric disorder) of patient 12, the activity level of patient 12 may be monitored to detect patient events. For example, a decreased activity level may indicate that patient 12 is experiencing increased tremors or is in a depressive mood state, and, therefore, the current therapy program may not be providing efficacious therapy to patient 12. Accordingly, in some examples, sensor 26 may monitor various patient parameters that indicate a patient activity level, such as heart rate, respiration rate, respiratory volume, core temperature, blood pressure, blood oxygen saturation, partial pressure of oxygen within blood, partial pressure of oxygen within cerebrospinal fluid, muscular activity, arterial blood flow, EMG, EEG, ECoG, and ECG. As another example, patient 12 may provide feedback, e.g., via programmer 20, relating to the occurrence of side effects, such as cognitive and/or psychiatric (e.g., changes in mood state) side effects.

Processor 40 of IMD 14 or processor 60 of programmer 20 may determine activity counts for patient 12 while therapy is delivered to patient 12 according to the current therapy program, and associate the activity counts with the current therapy program. Examples of determining activity counts and associating activity counts with therapy programs are described in U.S. Pat. No. 7,395,113 issued on Jul. 1, 2008 to Heruth et al., which is entitled, "COLLECTING ACTIVITY INFORMATION TO EVALUATE THERAPY," and was filed on Apr. 15, 2004. As described in U.S. Pat. No. 7,395,113 to Heruth et al., processor 40 of IMD 14 or processor 60 of programmer 20 may determine a number of activity counts based on signals generated by sensor 26, and the number of activity counts may be stored as an activity level associated with the current therapy program. For example, the number of activity counts may be a number of threshold crossings by a signal generated by sensor 26, such as an accelerometer or piezoelectric crystal, during a sample period, or a number of switch contacts indicated by the signal generated by sensor 26, such as mercury switch during a sample period. Upon determining that the activity level (or the number of activity counts) falls below a particular threshold level for a certain time range, such as one or more hours, days or weeks, processor 40 or 60 may determine that the current therapy program is not providing efficacious therapy to patient 12.

In examples in which therapy system 10 provides DBS to manage a mood disorder, such as bipolar disorder or major depressive disorder, of patient 12, or therapy system 30 provides SCS to manage the patient's pain, the sleep quality of patient 12 may indicate the efficacy of therapy. For example, if patient 12 is afflicted with bipolar disorder or major depressive disorder, poor sleep quality may indicate insomnia or a manic mood state. The insomnia or manic mood state may be a symptom of the patient's condition or side effect of the therapy delivery according to the current therapy program.

The quality of the patient's sleep may be determined using any suitable technique. In one example, processor 40 of IMD 14 determines values of one or more sleep metrics that indicate a probability of a patient being asleep based on the current value of one or more physiological parameters of the patient, as described in U.S. Patent Application Publication No. 2005/0209512 by Heruth et al., which is entitled, "DETECTING SLEEP" and was filed on Apr. 15, 2004. Processor 40 may then determine the number of disruptions in the patient's sleep, e.g., based on the number of times processor 40 determines patient 12 is not asleep during a particular time frame (e.g., 10 p.m. to about 8 a.m.).

As described in U.S. Patent Application Publication No. 2005/0209512 by Heruth et al., sensor 26 may generate a signal as a function of at least one physiological parameter of a patient that may discernibly change when the patient is asleep. Examples of suitable physiological parameters include activity level, posture, heart rate, respiration rate, respiratory volume, blood pressure, blood oxygen saturation, partial pressure of oxygen within blood, partial pressure of oxygen within cerebrospinal fluid, muscular activity, core temperature, arterial blood flow, and galvanic skin response. In some examples, the processor determines a value of a sleep metric that indicates a probability of the patient being asleep based on a physiological parameter. In particular, the processor may apply a function or look-up table to the current value and/or variability of the physiological parameter to determine the sleep metric value. The processor may compare the sleep metric value to a threshold value to determine whether the patient is asleep.

In some examples, a therapy system may be configured to deliver electrical stimulation therapy to patient 12 in order to manage urinary or fecal incontinence. In such cases, sensor 26 may be positioned to detect the occurrence of an involuntary urinary or fecal voiding event or urinary or fecal retention. In the case of fecal incontinence, sensor 26 may additionally or alternatively detect the occurrence of a loose bowel movement. Sensor 26 may provide the signals to programmer 20, and processor 60 may evaluate the efficacy of the current therapy program based on the number of involuntary voiding events associated with the current therapy program. Sensor 26 may, for example, detect a voiding event by detecting nerve impulses of a sacral or pudendal nerve, as described in U.S. Patent Application Publication No. 2007/0255176 by Rondoni et al., which was filed on Apr. 28, 2006 and is entitled, "VOIDING DETECTION WITH LEARNING MODE." As other non-limiting examples, sensor 26 may be disposed adjacent to patient 12 via an undergarment worn by patient 12, and may be configured to detect the presence of fluid, which may indicate that an involuntary voiding event has occurred. For example, as described in U.S. Pat. No. 7,855,653 issued on Dec. 21, 2010 to Rondoni et al., which was filed on Apr. 28, 2006 and is entitled, "EXTERNAL VOIDING SENSOR SYSTEM," sensor 26 may determine wetness by detecting a decrease in resistance between two electrodes of the sensor, or by detecting fluid pH, impedance, electrolyte concentration, or other characteristics of the fluid to identify that the fluid is urine.

Processor 60 may compare the total number of involuntary voiding events that occurred during therapy delivery via the current therapy program with a threshold value, which may be stored in memory 62. In other examples, processor 60 may compare the average number of voiding events for a sample period of time (e.g., average number of voiding events per day or week) with a threshold value. Upon crossing the threshold, processor 60 may determine that the current therapy program is not providing efficacious therapy to patient 12.

As other examples, in order to indicate the efficacy of the current therapy program in managing urinary incontinence, sensor 26 may be configured to provide information relating to the function of the bladder of patient 12, or any other segment of the patient's urinary tract, in storing, releasing, and passing urine. For example, as described in U.S. Patent Application Publication No. 2007/0100388 by Gerber, which was filed on Oct. 31, 2005 and is entitled, "IMPLANTABLE MEDICAL DEVICE PROVIDING ADAPTIVE NEUROSTIMULATION THERAPY FOR INCONTINENCE," sensor 26 may monitor patient parameters such as bladder pressure, bladder contractile force, urinary sphincter pressure, urine flow rate, urine flow pressure, voiding amount, and the like. These urodynamic parameters of patient 12 may indicate the efficacy of the current therapy program. The urodynamic parameters may, but do not necessarily indicate the occurrence of an involuntary voiding event.

In other examples, sensor 26 or other sensing devices may provide any suitable information to detect patient events that indicate therapy efficacy. The patient parameters that sensor 26 monitors may differ depending upon the patient condition for which the therapy program is implemented to manage.

If processor 60 determines that the current therapy program is providing efficacious to patient 12 based on the detected patient events (83), e.g., if no patient events detected or if the less than a threshold number of events are detected, processor 60 may continue monitoring signals from sensor 26 or IMD 14 to determine whether patient events have occurred (82). In addition, IMD 14 may continue delivering therapy according to the therapy program (80).

On the other hand, if processor 60 determines the current therapy program is not efficacious (83), processor 60 may reference therapy guidelines for the patient condition, where the therapy guidelines define a reference therapy field (72). As in the technique shown in FIG. 4A, processor 60 may determine therapy guidelines based on the detected patient event and the patient condition. For example, processor 60 may select therapy guidelines with functional outcomes directed toward decreasing the type of patient events detected. As previously described, the therapy guidelines include one or more reference therapy fields with known efficacy for treating a patient condition (e.g., a particular disease state), or producing a particular therapeutic outcome. Processor 60 may compare the algorithmic model of the therapy field based on the current therapy program to the reference field of the therapy guidelines (73) to determine what, if any, modifications should be made to the current therapy program. Processor 60 may then modify values of one or more therapy parameters of the therapy program based on the comparison between the algorithmic model of the therapy field and the reference therapy field (74). In this way, the therapy guidelines provide information that help a user modify a therapy program.

Figure 4C:
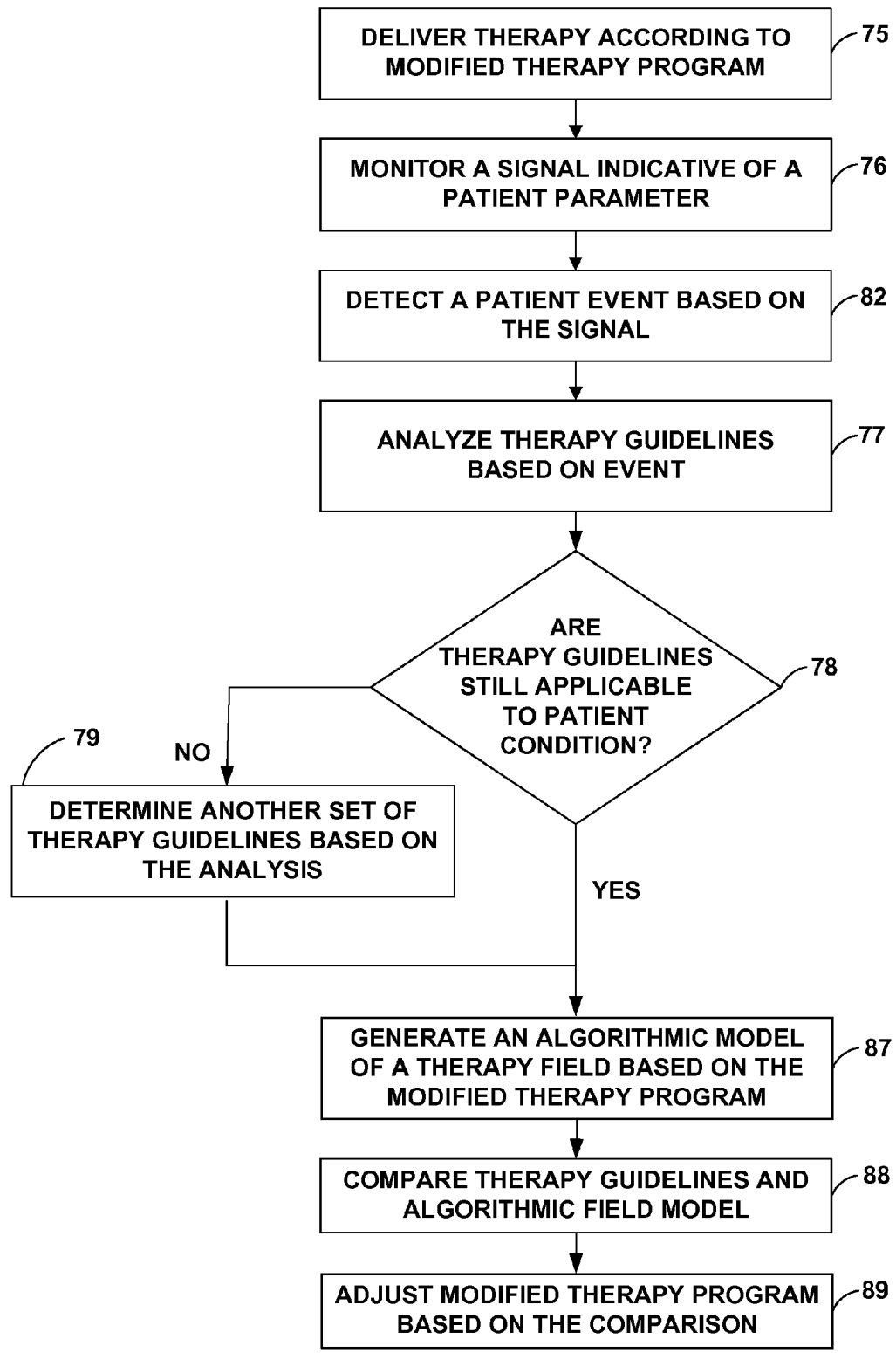

In some examples, processor 60 of programmer 20 may monitor therapeutic efficacy when therapy is delivered to patient 12 according to the modified therapy program including the adjusted therapy parameter values, as illustrated in FIG. 4C. The technique shown in FIG. 4C may be performed after the therapy program is modified based on the comparison between the algorithmic model of the therapy field and the reference therapy field (74), as described with reference to FIGS. 4A and 4B. Processor 60 may deliver therapy to patient 12 according to the modified therapy program (75) and monitor a signal indicative of a patient parameter (76), which may be a signal generated by sensor 26 or IMD 14. Processor 60 may detect a patient event based on the signal (82), as described above with respect to FIG. 4B. The patient event may reflect the occurrence of patient symptoms associated with the patient condition for which the therapy system is implemented or side effects from the therapy delivery, as examples. The detection of patient events may indicate that the therapy is not providing efficacious treatment of the patient condition.

Upon detection of a patient event, processor 60 may analyze the previously determined (e.g., previously selected or generated) therapy guidelines (77). Processor 60 may, for example, determine whether the previously-determined therapy guidelines are still applicable to the patient condition (78). The detected patient events may indicate that the patient's condition has changed, e.g., has worsened, and that a different set of therapy guidelines may provide more useful information for defining an efficacious therapy program for patient 12. In some cases, different degrees of progression or severity of a patient condition may be associated with different therapy guidelines. Accordingly, in one example, upon detection of a patient event (82) and a determination that the therapy guidelines are no longer applicable to the patient condition (78), processor 60 determines (e.g., selects) a different set of therapy guidelines (79). Processor 60 may determine that the previously-determined therapy guidelines are no longer best applicable to the patient condition relative to other therapy guidelines that may be selected. Thus, in other examples, processor 60 may analyze determined therapy guidelines (78) and verify that the selected therapy guidelines are bested suited for the patient condition compared to other available therapy guidelines.

After selecting another set of therapy guidelines (79) or determining that the previously-determined therapy guidelines are applicable to the patient condition (78), processor 60 generates an algorithmic model of a therapy field based on the modified therapy program (87). Processor 60 may also compare the therapy guidelines and the algorithmic field model (88) and modify the modified therapy program based on the comparison. In this manner, processor 60 may further modify the modified therapy program to generate a different stimulation field based on the therapy guidelines determined to be applicable to the patient condition. For example, if different therapy guidelines were determined to be applicable to the patient condition based on the detected patient event (78, 79), processor 60 may modify the modified therapy program to generate a different stimulation field based on the new set of therapy guidelines. As another example, if the originally-determined therapy guidelines were determined to be still applicable to the patient condition based on the detected patient event (78), processor 60 may increase the strength of the stimulation (e.g., by increasing a voltage or current amplitude and/or duration of the stimulation) to increase the size of the stimulation field.

Figure 5:
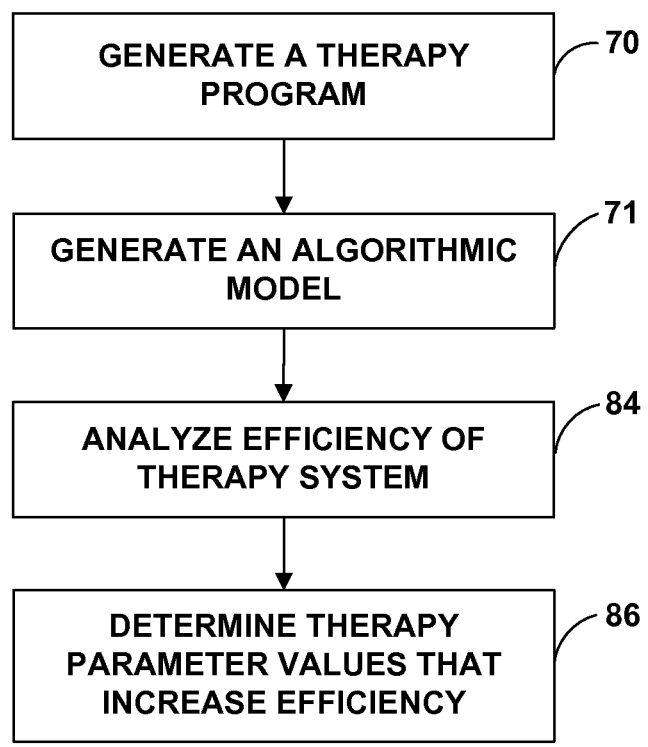
FIG. 5 is a flow diagram illustrating another example technique for modifying therapy parameters based on an algorithmic model of a therapy field.

FIG. 5 is a flow diagram illustrating another example technique for modifying one or more therapy parameter values based on an algorithmic model of a therapy field. As described with respect to technique shown in FIG. 4A, processor 60 of programmer 20 may generate (or select) a therapy program comprising a set of therapy parameter values for controlling therapy delivery by IMD 14 (70). Processor 60 may generate an algorithmic model of a therapy field based on the therapy program (71). In some examples, programmer 20 facilitates evaluation of multiple therapy programs, and processor 60 generates an algorithmic model for each of the therapy programs. The plurality of therapy program may be, for example, therapy programs that, as indicated by rating information received during a trialing session, provide efficacious therapy to patient 12.

Once an algorithmic model of the therapy field corresponding to the therapy program is generated, processor 60 may analyze the efficiency of therapy system 10 when therapy is delivered according to the therapy program (84). For example, processor 60 may access operating efficiency data, e.g., stored within memory 62 of programmer 20 and/or stored in another computing device or IMD 14 and accessed via telemetry interface 66. The operating efficiency data may relate to operating ranges of therapy system 10, and may be specific to, for example, a condition of patient 12, a desired therapeutic outcome, the target tissue site for therapy delivery, the anatomy of patient 12, and/or tissue-specific properties. In one example, the operating efficiency data defines guidelines that enable processor 60 or a user to modify one or more therapy parameter values of a therapy program to improve the energy efficiency of IMD 14 while substantially maintaining at least one field characteristic of a therapy field model generated based on the therapy program.

As one example, processor 60 may access a strength duration curve associated with a condition of patient 12. A strength-duration curve may describe the relationship between a strength of stimulation and duration, e.g., for a particular neurological response. The strength of stimulation may be a function of, for example, any one or more of the voltage or current amplitude value of the stimulation signal, frequency of stimulation signals, signal duration (e.g., pulse width in the case of stimulation pulses), signal burst pattern, and the like. An example of a strength duration curve is an amplitude-duration curve associated with a condition of patient 12. The amplitude-duration curve may reflect different combinations of amplitude and duration (e.g., pulse width in a case of stimulation pulses) values that contribute to the therapy field in a substantially similar manner. In this way, the amplitude-duration curve may describe different combinations of amplitudes and durations that elicit substantially similar to the same neurological responses. For example, the strength-duration curve may indicate that a lower amplitude stimulation pulse with a longer duration may elicit substantially the same neurological response as a higher amplitude pulse with a narrower pulse width.

Each position on the amplitude-duration curve, or each position within a particular range of positions along the amplitude-duration curve, may result in a substantially similar therapy field when the other therapy parameters remain substantially constant (e.g., the other therapy parameter values may remain within a particular range of therapy parameter values, such as within a 10% window or less from the values defined by the therapy program). As described in further detail below, different combinations of therapy parameter values that produce substantially similar therapy fields may require different levels of power consumption by IMD 14.

Processor 60 may also analyze the efficiency of therapy system 10 when therapy is delivered according to the therapy program by evaluating the amplitude of the stimulation signal based on the multiplier levels allowed by IMD 14. The multiplier levels may be used in conjunction with a strength-duration curve to analyze the efficiency of therapy system 10. IMD 14 may include a capacitor module that is configurable to store various voltages, i.e., various multiples of the voltage of power source 50 (FIG. 2). In one example, based on the selected configuration of the capacitor module, the capacitor module may output a voltage less than, equal to, or greater than the voltage supplied by power source 50. Processor 40 of IMD 14 may configure the capacitor module to store a voltage appropriate for the voltage or current amplitude specified by the therapy program. The capacitor module may include a plurality of capacitors and switches that processor 40 configures to store the appropriate voltage. Because the voltages that the capacitor module is capable of storing are limited by the possible configurations of the capacitors and switches, the capacitor module is capable of storing a finite number of discrete voltages.

Processor 40 of IMD 16 may configure the capacitor module to store a voltage that is sufficient to produce the amplitude specified by the therapy program. The stored voltage may be greater than the voltage necessary to produce the specified amplitude due to the limitations on the voltage values that the capacitor module can store. If the voltage stored by the capacitor module is greater than the voltage necessary to produce the amplitude specified by the therapy program, excess energy that is not used to produce the stimulation output is pulled from power source 50. Energy efficiency of IMD 14 may be increased the closer the voltage stored by the capacitor module is to the voltage necessary to produce the amplitude specified by the therapy program. Thus, to achieve maximum energy efficiency, the voltage stored by the capacitor module should typically equal the voltage necessary to produce the amplitude specified by the therapy program. Processor 60 of programmer 20 may compare the voltage necessary to produce the current or voltage amplitude specified by the therapy program to the multiplier levels allowed by the capacitor module of IMD 14 to evaluate energy efficiency. When the voltage required to produce the stimulation amplitude is between multiplier levels allowed by the capacitor module of IMD 14, IMD 14 does not operate at maximum efficiency.

Processor 60 may select an amplitude of a stimulation signal to increase the operating efficiency of IMD 14 based on the multiplier levels IMD 14 is configured to operate with, and select a duration, e.g., pulse width, appropriate for the desired stimulation intensity based an amplitude-duration curve or other operating efficiency data. For example, processor 60 may decrease an amplitude of a stimulation signal such that the voltage stored by the capacitor module is substantially equal to the voltage necessary to produce the amplitude and increase a duration of the stimulation signal in an amount determined from the amplitude-duration curve. As another example, processor 60 may increase an amplitude of a stimulation signal such that the voltage stored by the capacitor module is substantially equal to the voltage necessary to produce the amplitude and decrease a duration of the stimulation signal in an amount determined from the amplitude-duration curve. In other words, processor 60 may decrease a stimulation amplitude to allow use of a lower multiplier level with an increased duration or increase a stimulation amplitude to allow more efficient use of a higher multiplier level with a decreased duration. In this manner, processor 60 may adjust values of stimulation parameters to allow IMD 14 to generate the stimulation output more efficiency while providing substantially the same amount of stimulation energy to the patient and eliciting substantially the same patient response.

The amount of excess energy pulled from power source 50 of IMD 14 that is not used to produce a current or voltage stimulation amplitude is dependent upon the relationship between the voltage required to produce the stimulation amplitude and the multiplier level used to produce the amplitude. Using a higher multiplier level requires more energy from power source 50 than using a lower multiplier level. If the voltage required to produce a desired amplitude is larger than the voltage produced at a first, lower multiplier level, a second, higher multiplier level must be used. However, if the voltage required to produce the desired amplitude is only slightly larger than the voltage produced a the first, lower multiplier level, only a small portion of the energy that is pulled from power source 50 to go from the first, lower multiplier level to the second, higher multiplier level is used to produce the desired amplitude. The rest of the energy pulled from power source 50 to move to the next, higher multiplier level may, therefore, be excess energy that is not used to produce the stimulation amplitude. Therefore, decreasing an amplitude of a therapy program to operate at a lower multiplier level may significantly impact operating efficiency of the therapy system. The concept of decreasing an amplitude of a therapy program to operate at a lower multiplier level may also be referred to as avoiding operating above a voltage multiplier level.

Other types of operating efficiency data may include, for example, dose-response curves or three-dimensional (3D) depolarization field models. A dose response curve may provide information regarding general therapy outcomes, such as information regarding the amount of stimulation required to provide a particular therapeutic outcome. In some examples, a dose of stimulation is characterized by the intensity of stimulation, which may be affected by variables such as the voltage or current amplitude, signal duration (e.g., pulse width) or frequency of signal delivery defined by a therapy program, or a signal burst pattern of stimulation delivery. As one example, the dose response curve may specify that therapy should be delivered for about ten minutes per hour to provide efficacious therapy.

A dose response curve may also indicate a range of therapy parameter values that typically provide efficacious therapy. For example, a dose response curve may be used to predict whether changing a value of a particular therapy parameter in a particular direction (e.g., up or down, thereby increasing or decreasing, respectively, the dose of the therapy delivery) impacts therapy efficacy, and, in some cases, the extent to which therapy efficacy is impacted by the change to the therapy parameter value. If the dose response curve predicts that the therapy efficacy would remain unchanged within a particular range of therapy parameter values, the therapy parameter values of a therapy program for patient 12 may be changed to be within that range to improve efficiency of the therapy system without impacting therapy efficacy. As one example, a dose response curve may indicate that decreasing a stimulation frequency from a value greater than approximately 100 Hz to a value that is approximately 100 Hz will not impact the efficacy of DBS therapy.

A depolarization curve may describe the relationship between stimulation parameter values and the volume of tissue that is affected, e.g., depolarized. For example, 3D depolarization field models may indicate which anatomical structures are likely being activated and the extent of the activation. Processor 60 may select therapy parameter values that increase an operating efficiency of IMD 16 and maintain a specific volume of tissue that is affected.

The amplitude-duration curve, as well as other types of operating efficiency data, may be configured based on a condition (e.g., a particular disease state) of patient 12, a desired therapeutic outcome, tissue conductivity of the target delivery site, and/or other tissue properties of the target delivery site.

Based on the analysis of the data relating to the efficiency of therapy system 10 and the therapy program, processor 60 may automatically determine a second set of therapy parameters (i.e., a second therapy program) that increase an operating efficiency of therapy system 10 while substantially maintaining one or more characteristics of the therapy field (86). In some cases, processor 60 may reconfigure the active electrodes of leads 34, 36 and/or change other therapy parameter values to generate a therapy program that increases the operating efficiency of therapy system 10, but substantially maintains the therapeutic effects of the previously-selected therapy program. In some examples, processor 60 may adjust the therapy parameters to decrease the power consumption of IMD 14 and/or avoid operating between voltage multiplier levels of IMD 14. As one example, processor 60 may identify the position on the amplitude-duration curve that is most efficient for IMD 14. Different combinations of therapy parameters that produce substantially similar therapy fields may require different levels of power consumption by IMD 14. A small change in therapy parameter values may result in significant changes in battery recharge frequency and/or longevity. In some cases, it may be desirable to minimize power consumption by IMD 14 in order to increase the longevity of power supply 50 (FIG. 2).

In some examples, processor 60 generates an algorithmic model of the therapy field according to the second therapy program for comparison to the algorithmic model of the therapy field according to the original therapy program. As described in further detail below with reference to FIG. 7, processor 60 may display both of the modeled therapy fields to a user via user interface 64, compare respective field characteristics of the modeled therapy fields, and/or compute a metric indicative of how closely the therapy field model based on the second therapy program compares to the therapy field model based on the original therapy program. In some examples, processor 60 determines that the therapy field model based on the original therapy program is substantially maintained, if a difference, e.g., based on one or more field characteristics and/or metrics, between the therapy field model generated according to the second therapy program and the original therapy field model is below a threshold. The threshold may, for example, be selected by a clinician.

For example, processor 60 may compare the centroid of the original therapy field model with the centroid of the therapy field model based on the second therapy program. If a distance between the two centroids is less than a threshold value, processor 60 may determine that the therapy field is substantially maintained, which suggests that the second therapy program may provide substantially similar efficacy as the original therapy program. The threshold value may be stored within memory 62 and may be specific to a target stimulation site, a patient condition, and/or patient 12. In some examples, processor 60 may compare multiple field characteristics to respective threshold values to determine whether the therapy field is substantially maintained. As another example, processor 60 compares a metric value indicative of how closely the therapy field model based on the second therapy program resembles the original therapy field model to a threshold value to determine whether the therapy field is substantially maintained. Example metrics include the percentage of overlap (e.g., volumetric overlap or overlap in one or more cross-sections of the therapy field) between the original therapy field model and the therapy field model based on the second therapy program, or the volume of the therapy field model based on the second therapy program that does not overlap with the original therapy field model.

Substantially maintaining the one or more field characteristics of the original therapy field model based on the original therapy program may be desirable if the original therapy field model provides efficacious therapy for managing a particular patient condition or produces a particular therapeutic outcome. The process described with respect to FIG. 5 may allow the operating efficacy of therapy system 10, 30 to be increased without substantially impacting therapeutic efficacy. In some examples, processor 60 may first adjust the therapy parameter values of the original therapy program based on a reference therapy field defined by therapy guidelines, as described with respect to FIGS. 4A-4C, and subsequently adjust the therapy parameter values to increase an operating efficiency of therapy system 10, 30 while substantially maintaining the original therapy field, as described with respect to FIG. 5. By knowing the desired therapeutic outcome and the configuration of therapy system 10, a therapy program that helps to maximize the performance of therapy system 10 and generate a therapy field that is beneficial for the particular target tissue site, e.g., eliminate or minimize noxiousness and/or accommodation, may be determined.

FIGS. 6-16 illustrate various user interfaces and methods for generating algorithmic models of therapy fields and modifying therapy parameter values of a therapy program based on the therapy field models. While the remainder of the description of FIGS. 6-16 primarily refers to therapy system 10 of FIG. 1A including a single lead 16, in other examples, the techniques for using therapy field models to guide modification of therapy parameters may be applied to a therapy system including more than one lead, as well as a therapy system implanted proximate to other target tissue sites, such as therapy system 30 of FIG. 1B that provides SCS to patient 12.

Figure 6A:
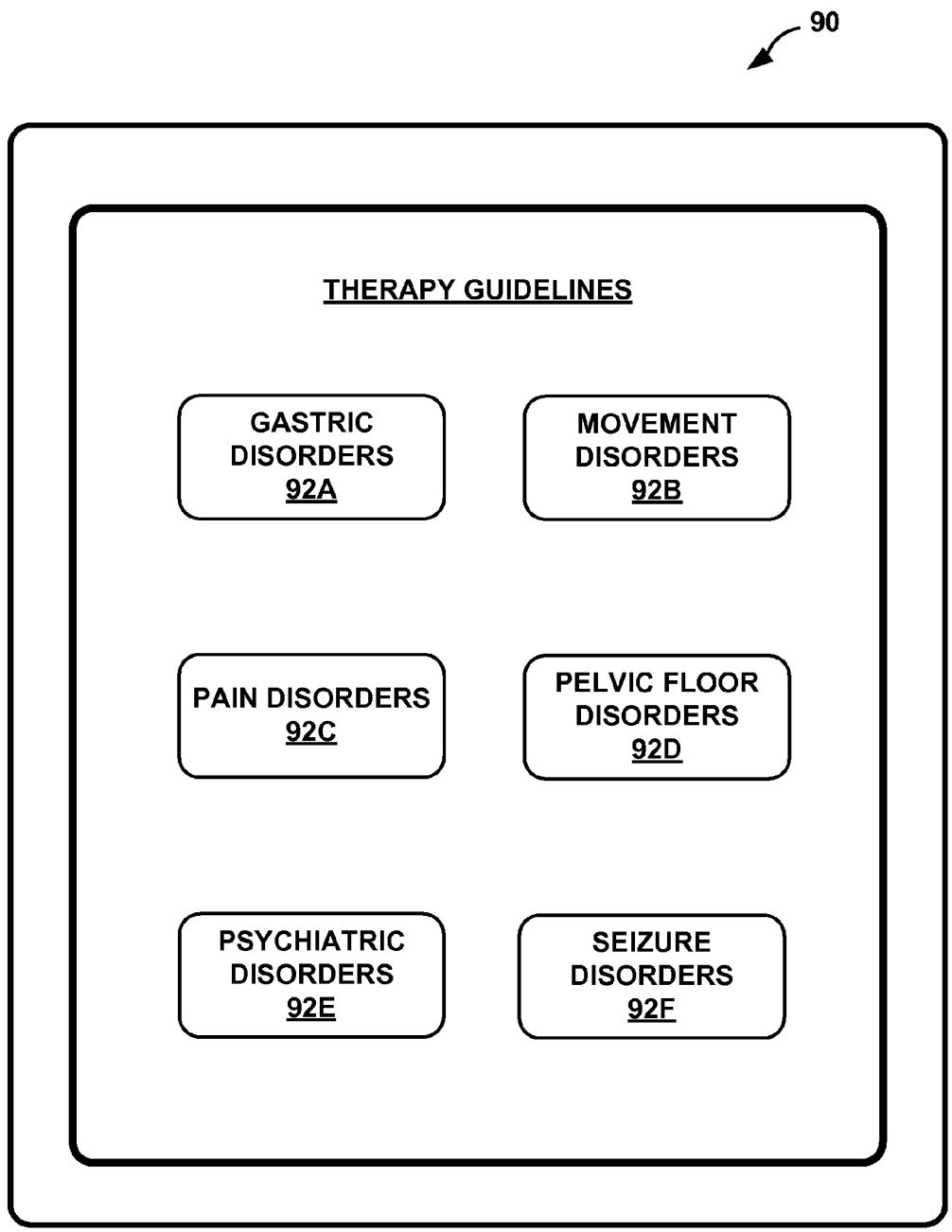
FIG. 6A illustrates a schematic representation of an example graphical user interface (GUI) that displays therapy categories via the display of the programmer of FIG. 3.

FIG. 6A illustrates an example graphical user interface (GUI) 90 that may be presented on the display of user interface 64 of programmer 20 (FIG. 3) or another computing device to allow a user to select a set of therapy guidelines based on a patient condition. GUI 90 presents the user with a list of different types of patient conditions. In the example illustrated in FIG. 6A, GUI 90 displays gastric disorders 92A, movement disorders 92B, pain disorders 92C, pelvic floor disorders 92D, psychiatric disorders 92E, and seizure disorders 92F (collectively "therapy categories 92") for selection. In other examples, GUI 90 may present any number or type of therapy categories for selection.

In the example shown in FIG. 6A, GUI 90 includes selectable text boxes that specify the different therapy categories 92. A user may determine (e.g., select) a therapy guideline by selecting the text box with a stylet, a mouse or another peripheral pointing device, or by selecting a button on programmer 20. In other examples, the list of therapy categories 92 may be presented in any suitable form. For example, therapy categories 92 may be presented by a drop down list or may be associated with alphanumeric identifiers (e.g., categories "A" and "B"), and the user may input the alphanumeric identifier to select a therapy category.

Figure 6B:
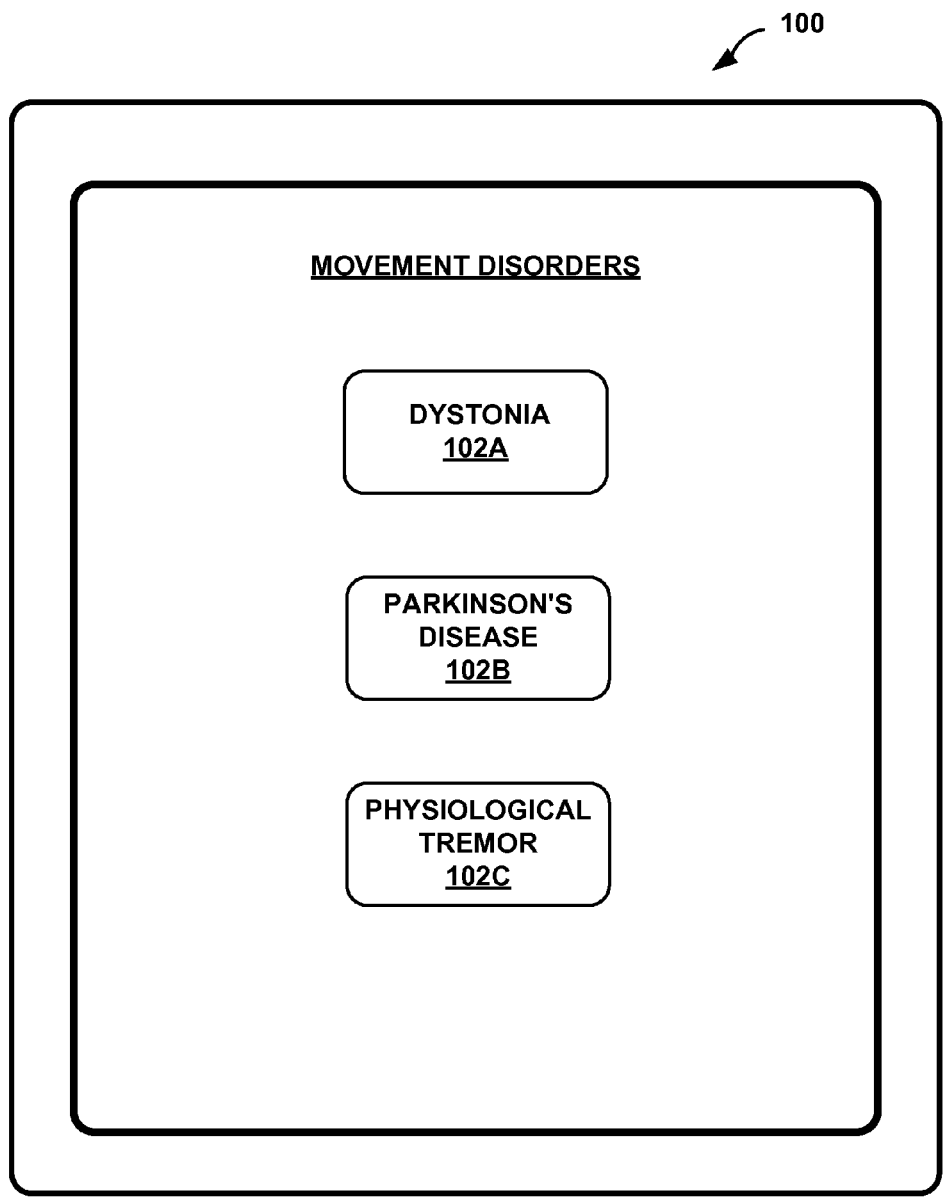
FIG. 6B illustrates a schematic representation of an example GUI that displays a listing of patient conditions within a therapy category via the display of the programmer of FIG. 3.

Upon selection of a therapy category 92 from GUI 90, programmer 20 may present GUI 100 relating to the selected therapy category. As illustrated in FIG. 6B, GUI 100 may present the user with a listing of different disorders within the selected therapy category 92. In the example illustrated in FIG. 6B, GUI 100 displays dystonia 102A, Parkinson's Disease 102B, and physiological tremor 102C within the movement disorder therapy category 92B. Again, although the disorders are presented as selectable text boxes, in other examples, the patient disorders may be presented in any suitable form.

Figure 6C:
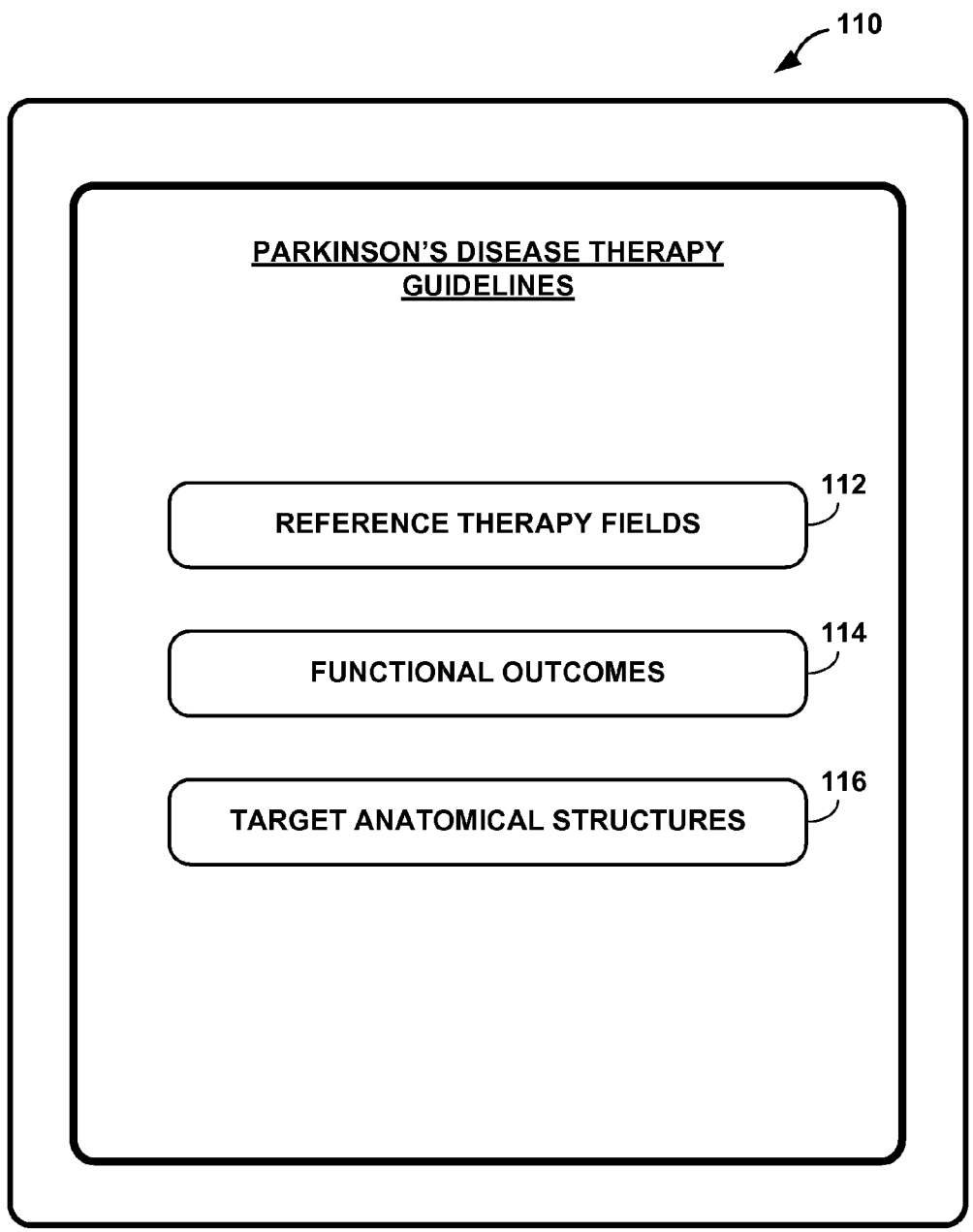
FIG. 6C illustrates a schematic representation of an example GUI that displays therapy guidelines for a selected patient condition via the display of the programmer of FIG. 3.

FIG. 6C illustrates an example GUI 110 that allows a user to view therapy guidelines for a particular patient condition. In the example illustrated in FIG. 6C, GUI 110 displays guidelines for Parkinson's disease 102B (FIG. 6B). In the example shown in FIG. 6C, the therapy guidelines include reference therapy fields 112, functional outcomes 114, and target anatomical structures 116. The user may select any of the different types of information that make up the therapy guidelines in order to view more information about the therapy guidelines. The types of guideline information may be presented as selectable text boxes or via any suitable form.

The user may select reference therapy fields 112 in order to view more information about the reference therapy fields that may have known efficacy for treating a patient condition or producing a therapeutic outcome for Parkinson's Disease. For example, as described with respect to FIG. 7, programmer 20 may present a visual representation of the reference therapy field relative to schematic illustrations of leads and/or patient anatomy. The patient anatomy displayed with the reference therapy fields may be specific to patient 12 or may be more general.

The user may select functional outcomes 114 to view a list of functional outcomes that may be achieved by using the selected therapy guidelines for Parkinson's disease, such as by generating a stimulation field that is similar to the reference therapy fields or generating a stimulation field that activates specific target anatomical structures 116 within brain 18. Accordingly, the functional outcomes 114 may be specific to the selected therapy guidelines and may include, for example, mitigation of one or more symptoms associated with the patient's condition. For example, functional outcomes 114 of Parkinson's disease may include a decrease in resting tremors (e.g., in the frequency range of approximately 4 Hertz (Hz) to approximately 7 Hz) and an improvement in gait and mobility.

The user may select target anatomical structures 116 to view a list of anatomical structures that may be stimulated in order to manage Parkinson's Disease, or to view a diagram illustrating the target anatomical structures. Thus, the therapy guidelines may indicate the particular anatomical structures 116 that should be activated by an electrical field in order to effectively manage the patient's condition.

Figure 14:
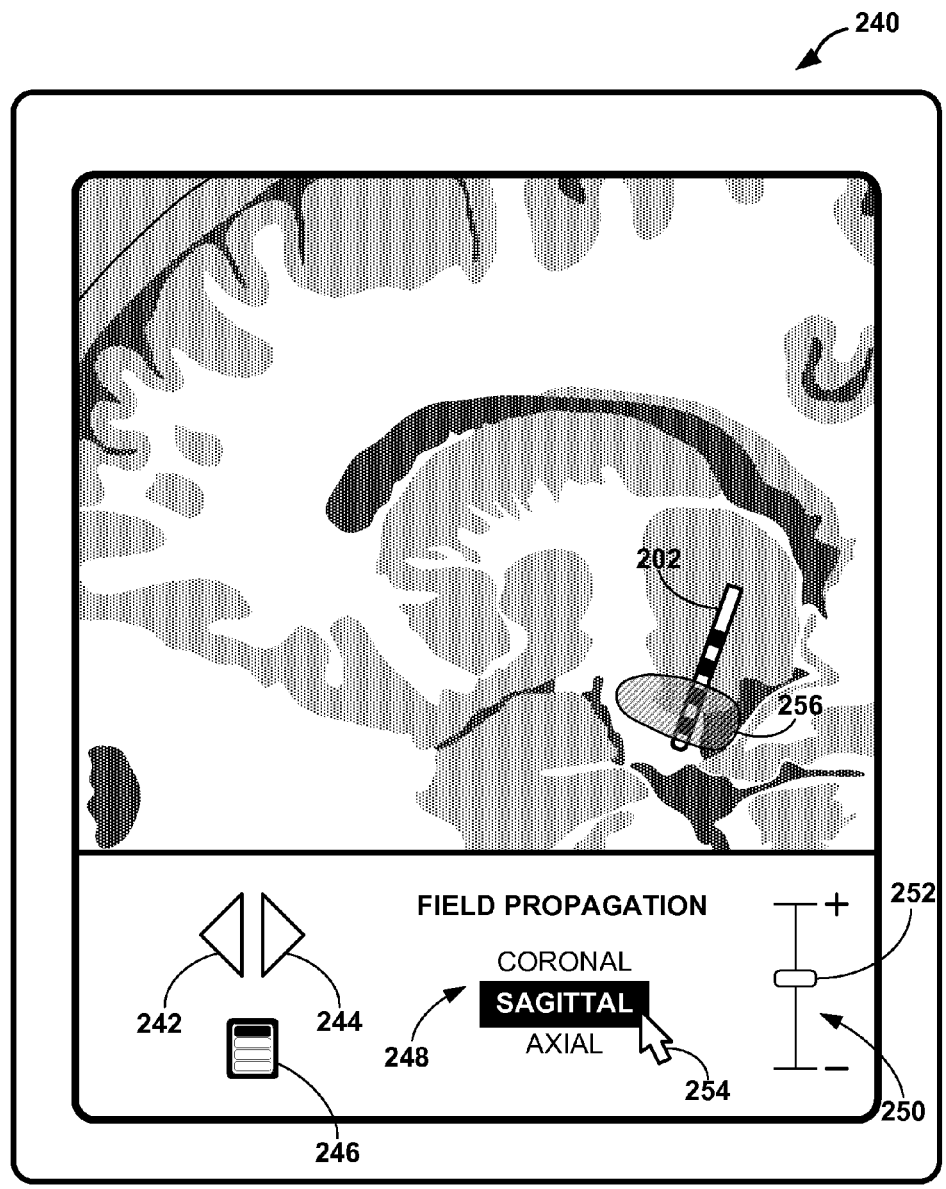
FIG. 14 is an example screen shot of a GUI that presents a sagittal view of a patient anatomy with an algorithmic model of an electrical field.
Figure 15:
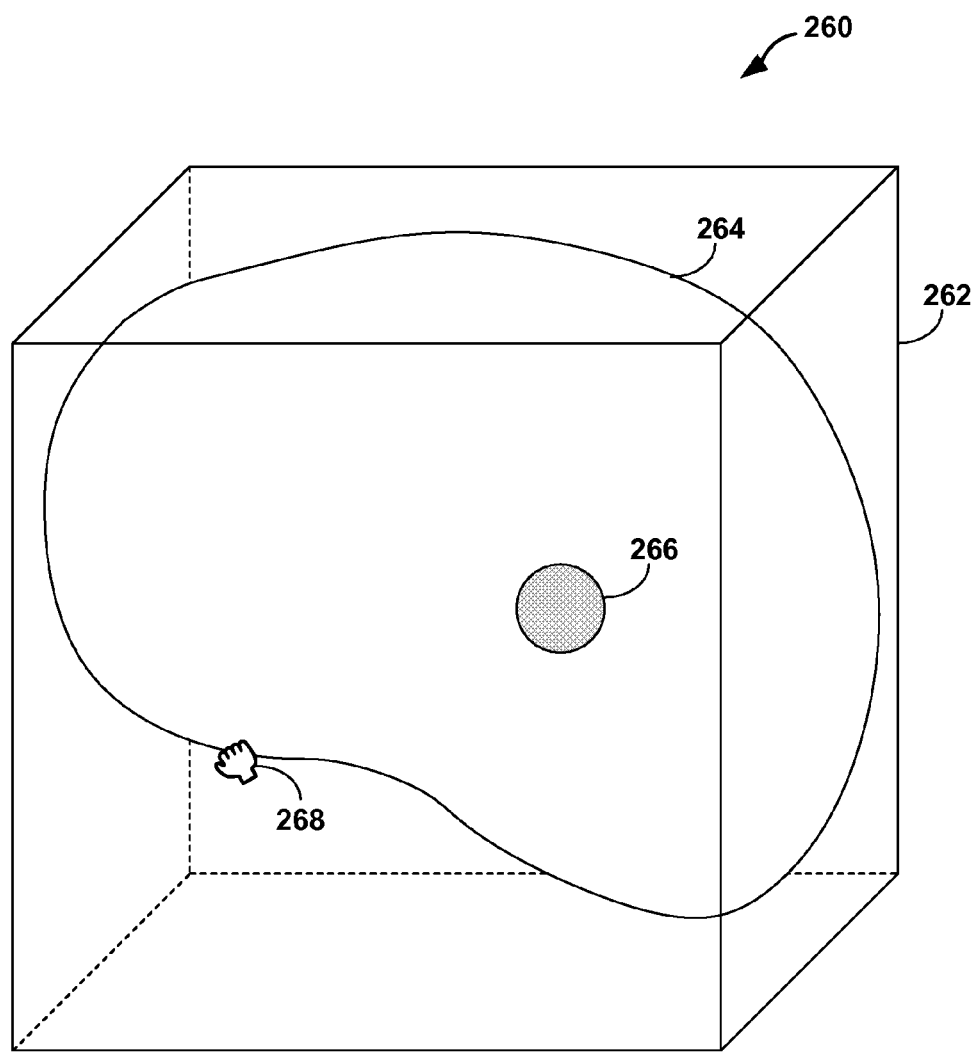
FIG. 15 is a conceptual diagram illustrating a three-dimensional (3D) visualization environment including a 3D brain model for defining a 3D stimulation field.

For example, stimulating the Substantia Nigra in brain 18 may reduce the number and magnitude of tremors experienced by patient 12. In some examples, the location of target anatomical structures 116 and reference therapy fields 112 may be viewed on an anatomical reference. For example, upon selection of reference therapy fields 112 and/or anatomical structures 116 on GUI 110, processor 60 may display the selected reference therapy fields 112 and/or anatomical structures 116 on GUI 200 (FIG. 12), 240 (FIG. 14) or 260 (FIG. 15).

Figure 7:
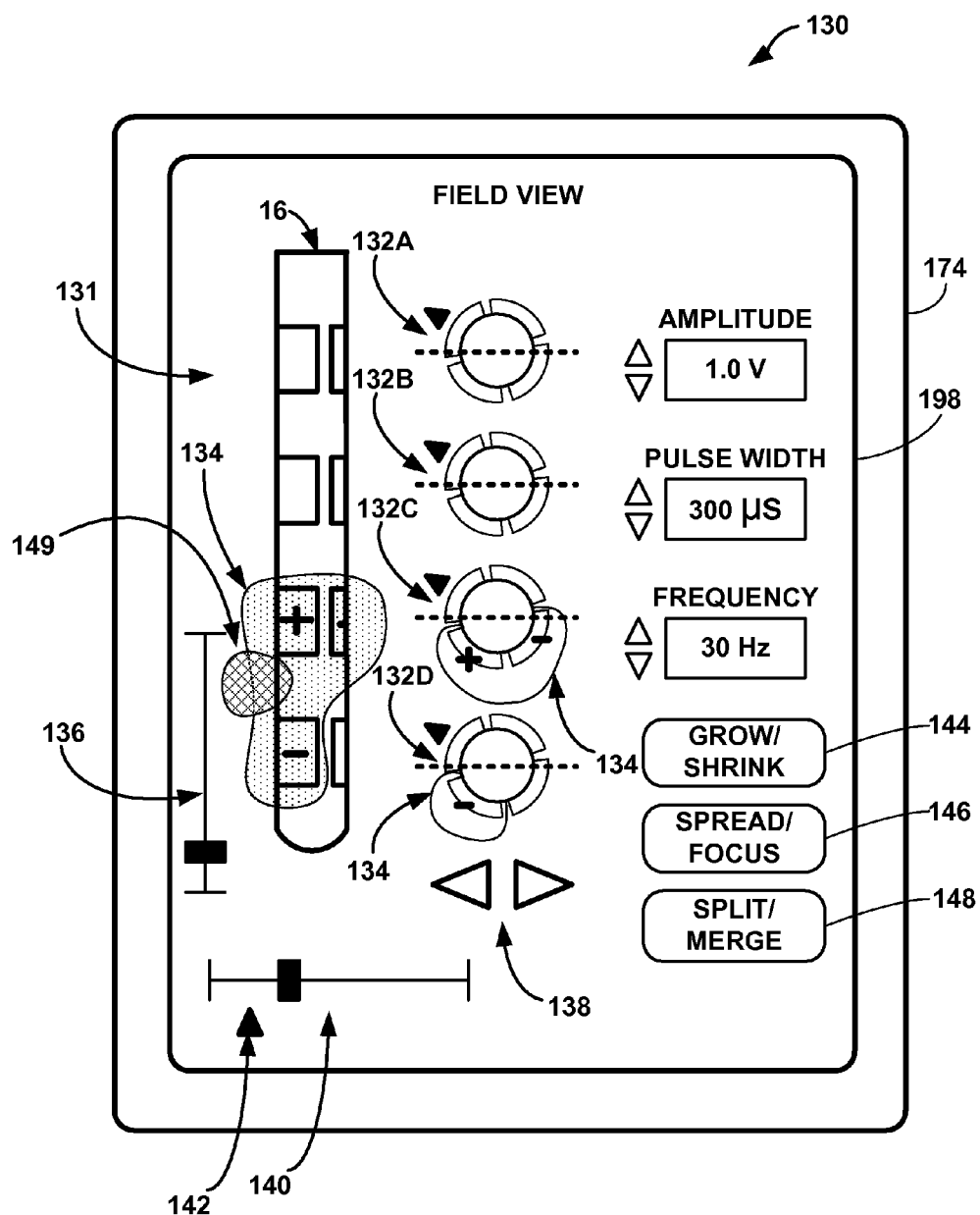
FIG. 7 illustrates a schematic representation of an example GUI that may be presented on the display of the user interface of the programmer of FIG. 3.

FIG. 7 illustrates a schematic representation of an example GUI 130 that may be presented on the display of user interface 64 of programmer 20 of FIG. 3. By interacting with GUI 130, a user may generate an algorithmic model of an electrical stimulation field produced by a selected therapy program. In some examples, the user may be able to create a stimulation field in the field view and direct processor 60 of programmer 20 to generate a set of therapy parameter values (e.g., a therapy program) that would best match the stimulation field. In some examples, the user may change the size, shape or position of the stimulation field within GUI 130 using graphical input media such as cursor or stylus control. The generated electrical stimulation field may be utilized as an algorithmic model of a therapy field associated with the generated parameters. More particularly, as described below, a comparison of the stimulation field model generated with the aid of GUI 120 to a reference therapy field defined by therapy guidelines and/or analysis of the efficiency of therapy system 10 may be used to modify the therapy parameter values.

GUI 130 illustrates lead 16, which includes a complex electrode array geometry. A complex electrode array geometry generally refers to an arrangement of stimulation electrodes at multiple non-planar or non-coaxial positions, in contrast to simple electrode array geometries in which the electrodes share a common plane or a common axis. An example of a simple electrode array geometry is an array of ring electrodes distributed at different axial positions along the length of a lead comprising a circular cross-section. This type of electrode array geometry is shown in FIG. 2. Another example of a simple electrode array geometry is a planar array of electrodes on a paddle lead.

In the example of FIG. 7, rather than including four electrodes 17 as shown in FIG. 1A, lead 16 includes four electrode "levels" at different axial positions along the length of the lead. Each level includes four electrodes generally arranged in a ring. However, the electrodes are non-contiguous with one another. The electrodes may be referred to as segmented electrodes or electrode segments. Each electrode is coupled to a respective electrical conductor within lead 16. Hence, lead 16 includes multiple electrical conductors, e.g., wires, cables or the like, that extend from the proximal end of the lead to respective electrodes to electrically couple the electrodes to electrical terminals associated with IMD 14.

Each electrode is positioned at a different angular position around the circumference of implantable lead 16, which has a generally circular cross-section in the example of FIG. 7. Each electrode is independently selectable so that stimulation energy can be delivered from the lead at different axial and angular positions. In some examples, lead 16 may include combinations of complex electrode array geometries and simple electrode array geometries. For example, ring electrodes that extend about the entire circumference of the lead may be used in combination with electrodes disposed at different axial and angular positions. Selective activation of the electrodes carried by lead 16 can produce customizable stimulation fields that may be directed to a particular side of lead 16 in order to isolate the stimulation field around a target anatomical region of brain 18.

GUI 130 illustrates a side view 131 and multiple cross-sectional views 132A-132D of lead 16 in alignment with corresponding electrode levels. In the example shown in FIG. 7, the user has selected an initial electrode combination, either manually or by selection from a set of electrode combinations provided by programmer 20, and the selected electrode combination is illustrated in GUI 130. GUI 130 presents a representation of a stimulation field 134 defined by the user and produced by the selected electrode combination, given stimulation parameter values selected by the user and general tissue characteristics stored within programmer 20. The general tissue characteristics may include, for example, impedance of tissue proximate to the electrodes of lead 16. Stimulation field 134 may represent an algorithmic model of a therapy field.

The size and shape of stimulation field 134 may be established based on generic physical characteristics of human tissue and known physical characteristics of the electrodes of lead 16. In other words, stimulation field 134 displayed in GUI 130 may only be an approximation of what the stimulation field would be in brain 18 of a specific patient 12. However, in some examples, physical characteristics of the actual anatomical structure of patient 12 being treated may be used to generate stimulation field 134. This anatomical structure information may be presented to programmer 20 in the form of patient anatomical data generated by an imaging modality, such as CT, MRI, or any other volumetric imaging system and stored within memory 62 (FIG. 3). In the example that uses the patient anatomical data, stimulation field 134 may be similar to an electrical field model, which is discussed in detail with reference to FIGS. 8 and 10. For example, stimulation field 134 may rely on tissue impedance models, field propagation models, and the like. In some examples, stimulation field 134 may be a representation of an electrical field, current density, voltage gradient, or neuron activation, applied to a generic human tissue or the anatomy of patient 12. In addition, the user may be able to switch between any of these representations when desired.

The user may move stimulation field 134 up or down relative to a longitudinal axis of lead 16 using vertical scroll bar 136 or some similar control interface. As stimulation field 134 moves up or down in response to the user input, programmer 20 automatically selects appropriate electrode combinations to support the vertical movement of stimulation field 134 within GUI 130. For example, processor 60 may phase electrodes in and out as stimulation field 134 travels upward or downward, reducing the stimulation energy delivered from some electrodes as the stimulation field moves away from them, and increasing the stimulation energy delivered by other electrodes as the field moves toward them. Also, GUI 130 includes arrows 138 or similar input media that permit the user to transition between different electrode levels of the lead in cross-sectional views 132A-132D.

In addition, the user may rotate stimulation field 134 using horizontal scroll bar 140 or some similar control device. An arrow 142 may be provided next to horizontal scroll bar 140 to indicate the orientation of lead 16 relative to an anatomical structure. In addition, arrows may be provided in respective cross-section views 132A-132D to maintain orientation. As the user rotates stimulation field 134, processor 60 of programmer 20 may automatically select appropriate electrode combinations to support the rotational movement of the stimulation field 134. As in the case of vertical movement, rotational movement of stimulation field 134 may be accomplished by gradually reducing the stimulation energy delivered to some electrodes as the stimulation field rotates away from them, and gradually increasing the stimulation energy delivered to other electrodes as the stimulation field rotates toward them. Side view 131 and cross-sectional views 132A-132D permit the user to observe movement of stimulation field 134 from both an axial perspective and a rotational perspective.

Movement of stimulation field 134 within GUI 130 using scroll bars 136, 140 or similar input media permits the user to evaluate different stimulation field positions without the need to manually select electrodes and manually enter parameter values. Instead, processor 60 of programmer 20 automatically selects electrodes and parameter values in response to movement of stimulation field 134 by the user. Although scroll bars 136, 140 are illustrated as examples of input media for movement of stimulation field 134, other types of input media may be used. Examples include up/down arrows or side-to-side arrows, which may be presented on a touch screen or formed by buttons or keys on programmer 20.

As a further alternative to manipulating the stimulation field 134, the user may select stimulation field 134 with a stylus, mouse, or other pointing device and drag the field upward, downward, or rotationally. In some examples, a mouse or other pointing device may support left or right click functionality to perform different operations relative to stimulation field 134. With a stylus, a first click on stimulation field 134 may initiate movement, dragging with the stylus directs movement relative to the schematic illustration of lead 16 in GUI 130, and a second click may terminate movement. In each case, processor 60 of programmer 20 responds to the specified movement by automatically adjusting the electrode combination and the stimulation parameters to approximate the characteristics of stimulation field 134 presented by GUI 130. As the stimulation parameter values change, the size and shape of stimulation field 134 presented on the display change. Similarly, as the electrode combination changes in terms of polarity or electrode selection, the size, shape or direction of stimulation field 134 presented on the display changes.

In some examples, processor 60 of programmer 20 may utilize stimulation templates and select the best fitting stimulation template set to a newly modified stimulation field 134 in order to generate therapy parameter values for achieving stimulation field 134. A stimulation template is a predetermined volumetric stimulation field that processor 60 of programmer 20 may substantially match to a desired stimulation field 134 from the user. An algorithm for generating stimulation parameter values that fit the user defined stimulation field may be less computationally intensive for processor 60 compared to an algorithm that references multiple equations or lookup tables to generate the stimulation parameters. The stimulation template may be a representation of an electrical field or other electrical stimulation related characteristic, e.g., current density, voltage gradient, or neuron activation, applied to a generic human tissue. For stored stimulation templates, processor 60 may adjust the current amplitude or voltage amplitude to alter the size of the stimulation template to cover the desired stimulation field 134 from the user. Examples of stimulation templates are described in U.S. Patent Application Publication No. 2007/0203541 by Goetz et al.

Processor 60 of programmer 20 may limit the rate of movement of stimulation field 134 within GUI 130. In other words, stimulation field 134 may only be moved a certain number of steps per second within GUI 130, or any other user interface that allows the user to drag the stimulation field. This rate movement limit may prevent unnecessary calculations or ensure patient comfort in real-time programming examples.

In addition to moving stimulation field 134, GUI 130 may permit the user to perform one or more operations that result in reconfiguration of stimulation field 134. For example, the user may click on a border, i.e., an outer perimeter, of stimulation field 134, and drag it inward or outward to resize the stimulation field. Resizing by enlarging or shrinking stimulation field 134 in GUI 130 may result in an increase or decrease in amplitude, pulse width or pulse rate values of the therapy program used to generate stimulation field 134. In some examples, enlarging or shrinking stimulation field 134 also may result in selection or de-selection of electrodes included in the existing electrode combination. In either case, processor 60 of programmer 20 adjusts the electrode combination and/or parameter values in response to the enlargement or shrinkage of stimulation field 134 by the user.

When a user clicks on stimulation field 134 border and drags it, the entire stimulation field may be expanded in two dimensions in equal proportions. Alternatively, stimulation field 134 may expand only in the direction in which the user drags the stimulation field. For example, horizontal dragging of the field perimeter to enlarge stimulation field 134 may result in overall enlargement of the cross-sectional seize of stimulation field 134, keeping the vertical to horizontal aspect ratio constant. Alternatively, horizontal dragging may result only in horizontal expansion, leaving the vertical dimension constant. The application of a constant or varying aspect ratio may be specified by a user as a user preference. Alternatively, programmer 20 may provide different aspect ratio modes on a selective basis for expansion and shrinkage of stimulation field 134.

To enlarge or shrink stimulation field 134, the user may simply click on the stimulation field border within GUI 130. Alternatively, the user may click on a grow/shrink button 144 as shown in FIG. 7, and then click on the border of stimulation field 134 to drag it inward or outward and thereby adjust the size of the stimulation field. In response, processor 60 of programmer 20 may automatically reconfigure the electrode combination and/or stimulation parameter values to approximate the resized stimulation field. In this way, a user may generate an algorithmic model of a therapy field by directly manipulating the stimulation field 134. Other field adjustment functions such as spread/focus button 146 and split/merge button 148 may be provided by GUI 130. In each case, the user changes stimulation field 134 by simply changing the representation of the stimulation field 134 presented on GUI 130, thereby avoiding the need to manually select electrodes and parameter values. The operation of the buttons 144, 146, and 148 is described in further detail in U.S. Patent Application Publication No. 2007/0203541 by Goetz et al.

After selecting a desirable stimulation field 134, processor 60 of programmer 20 may generate an algorithmic model of an electrical field and/or an algorithmic model of an activation field that corresponds to stimulation field 134. Techniques for generating algorithmic models of electrical fields and activation fields are described with reference to FIGS. 8-11. The model of the electrical field and/or the model of the activation field may be utilized as the algorithmic model of a therapy field associated with the set of therapy parameter values that generate stimulation field 134. As previously discussed, the algorithmic model of the therapy field may be useful for guiding the modification of therapy parameter values. In accordance with example techniques described above with respect to FIGS. 4A-4C, for example, the therapy parameter values are based on a comparison of the therapy field model to a reference therapy field defined by therapy guidelines and/or analysis of the efficiency of therapy system 10.

In FIG. 7, processor 60 of programmer 20 may display reference field 149 in addition to the electrical field model and/or activation field model on GUI 130. For example, reference field 149 may be displayed concurrently with the stimulation field 134 or a user may be permitted to toggle between views of stimulation field 134 and reference field 149. In some examples, a user may select which type of therapy field models (e.g., stimulation field, activation field or electrical field) and/or reference fields GUI 130 displays. Reference field 149 may be provided as part of therapy guidelines (FIGS. 6A-6C), and may include an electrical field or an activation field that is known or believed, by the clinician, to manage the patient's condition (e.g., based on one or more other patients and their respective responses to therapy delivery via a therapy field that resembles the reference field), and may be stored within memory 62 of programmer 20. The user may select therapy guidelines with the aid of programmer 20, as previously described with reference to FIGS. 6A-6C.

As described previously, processor 60 may facilitate comparison of the electrical field model or activation field model to reference field 149. Processor 60 may also adjust the stimulation parameter values of a therapy program based on the comparison. In the example shown in FIG. 7, stimulation field 134 has a greater volume than reference field 149. Processor 60 may calculate the ratio of the volume of reference therapy field 149 to the volume of stimulation field 134. Additionally or alternatively, processor 60 may analyze the percentage of overlap between reference field 149 and stimulation field 134 and/or the volume of stimulation field 134 that falls outside of reference field 149. Based on its comparison, processor 60 may adjust one or more stimulation parameter values of the therapy program on which stimulation field 134 is based, e.g., to decrease the size and/or position of stimulation field 134. GUI 130 may display one or more therapy field models and/or stimulation fields associated with the adjusted set of stimulation parameters.

Processor 60 of programmer 20 may also analyze the power efficiency of therapy system 10 when IMD 14 delivers stimulation according to the therapy program selected by processor 60. For example, processor 60 may adjust the stimulation parameter values of the therapy program based on operating efficiency data in order to increase the operation efficiency of therapy system, 10 while substantially maintaining at least one characteristic of stimulation field 134, such as volume or centroid of stimulation. In some examples, processor 60 may generate an algorithmic model of therapy field based on the adjusted set of stimulation parameter values, and GUI 130 may display the therapy field model in addition to or instead of stimulation field 134 and/or reference field 149, to verify that the at least one characteristic of the therapy field is substantially maintained.

Figure 8:
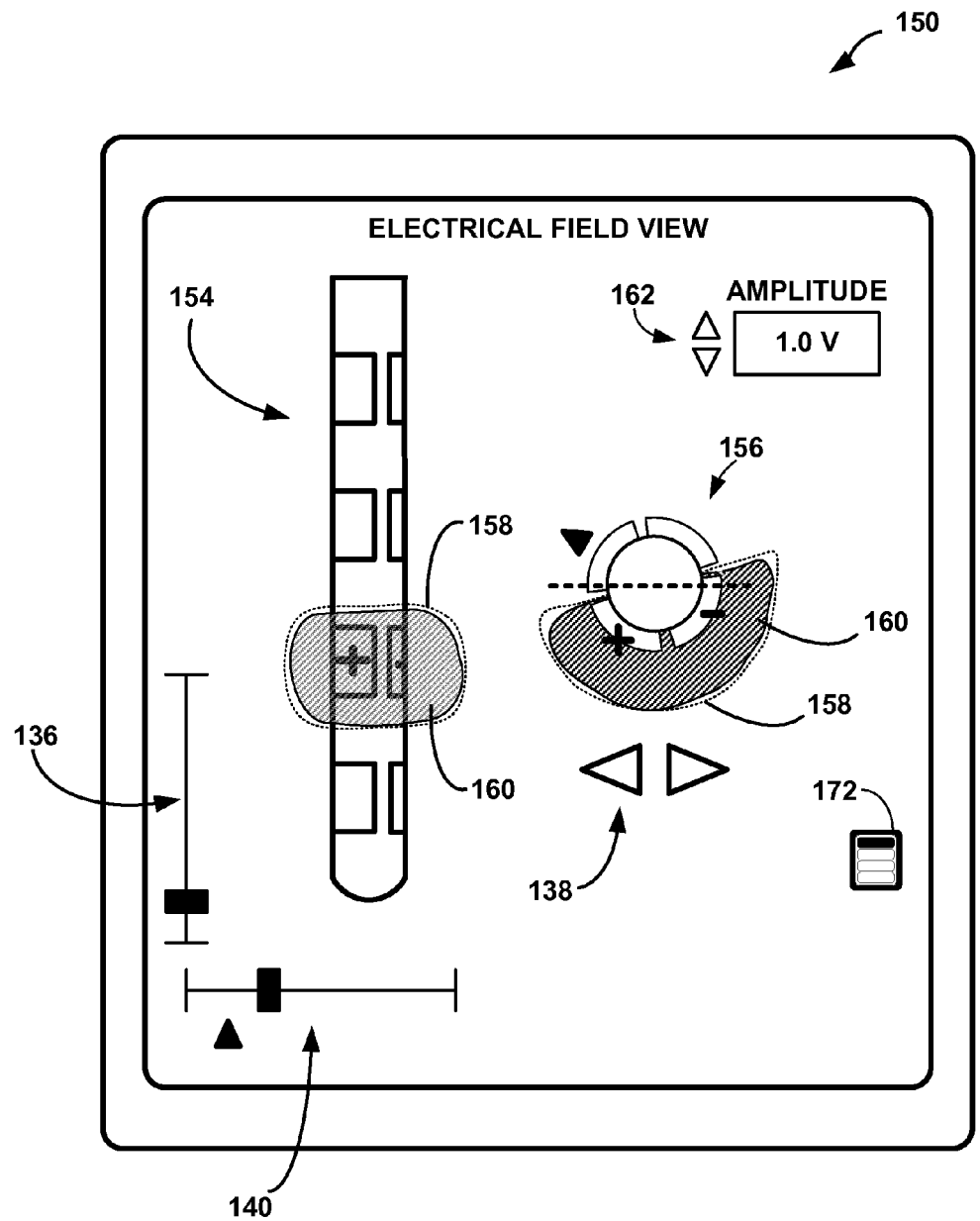
FIG. 8 illustrates an example GUI that displays a stimulation field view to the user via the display of the programmer of FIG. 3.
Figure 9:
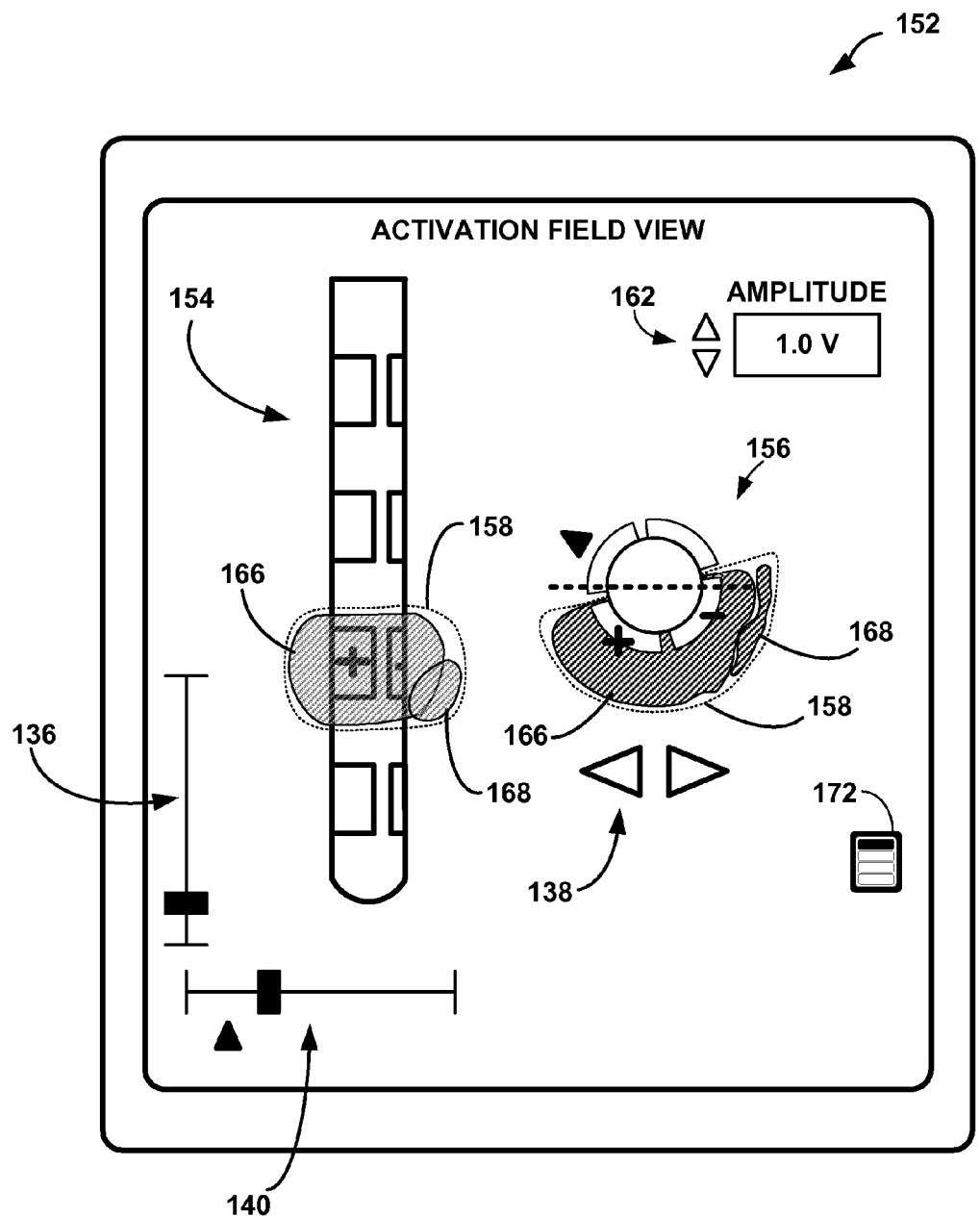
FIG. 9 illustrates an example GUI that displays an activation field view to the user via the display of the programmer of FIG. 3.

FIGS. 8 and 9 are schematic diagrams illustrating example GUIs 150, 152 that present electrical field models and activation field models, respectively, to a user. FIG. 8 illustrates an example GUI 150 that displays a stimulation field view to the user via the display of programmer 20. GUI 150 displays side view 154 and cross-sectional view 156 of implanted lead 16, and the user defines stimulation field 158 on the side and cross-sectional views, e.g., using the techniques described above with respect to FIG. 7. Processor 60 of programmer 20 may generate a therapy program for therapy based on the selected stimulation field 158 and generate an electrical field model 160, which estimates an electrical field that results from therapy delivery according to the stimulation parameters associated with the selected stimulation field 158. In GUI 150, electrical field model 160 is displayed as an electrical field within the outer boundaries of stimulation field 158. In other examples electrical field model 160 may be a representation of another electrical stimulation related characteristic, e.g., current density, or voltage gradient. In addition, the user may be able to switch between any of these representations when desired.

Electrical field model 160 represents where the electrical current will propagate from the implanted lead 16 within tissue of patient 12, as tissue variation within patient 12 at the target tissue site may change the electrical current propagation from the lead in some directions. The variations in electrical field propagation may affect the ability of the therapy to actually treat a desired structure of brain 18 in examples in which IMD 14 delivers stimulation to brain 18 (FIG. 1A) or cause a side-effect. The horizontal and axial views of electrical field model 160 illustrated in FIG. 8 are 2D slices of a volumetric electrical field model generated by processor 60 of programmer 20. Processor 60 utilizes an algorithm to generate electrical field model 160. In one example, the algorithm considers the patient anatomy data and electrical field model equations that define electrical current propagation. Accordingly, if the algorithmic model of the therapy field includes electrical field 160, processor 60 may implement an algorithm that applies electrical field model equations that define how the electrical field propagates away from an origin location. The electrical field model equations may be specific to patient 12. The electrical field equations require the physical tissue characteristics of the tissue adjacent lead 16, which is included in the patient anatomy data set. From this information, processor 60 is able to generate the estimated electrical field 160 that will be produced in therapy.

Electrical field 160 may differ from the selected stimulation field 158 because processor 60 generates stimulation field 158 using an algorithm that only considers general tissue characteristics, which are not specific to patient 12. In other examples, the electrical field equations may utilize matrices or other mathematical model of the electrical field. In this manner, electrical field 160 can be estimated and modeled for the user. Accordingly, the user may be able to increase or decrease the amplitude of the stimulation parameters with an amplitude interface 162 in order to change the size and possibly shape of electrical field 160 or directly manipulate electrical field 160.

Once the user is satisfied with electrical field 160, processor 60 may compare electrical field model 160 to a reference field (e.g., reference field 149 in FIG. 7) defined by therapy guidelines as described with respect to FIGS. 4A-4C, and/or analyze the efficiency of therapy system 10 based on the stimulation parameter values used to generate electrical field model 160, as describe with respect to FIG. 5. In some examples, GUI 150 may display the reference therapy field specified by the therapy guidelines selected by the user, and/or an electrical field model associated with the modified therapy program that resulted from the comparison to the reference field. In examples in which processor 60 adjusts the stimulation parameter values to increase the operation efficiency of therapy system 10 while substantially maintaining the electrical field, GUI 150 may display a model of the electrical field associated with the adjusted parameters to allow the user to verify that the therapy field is substantially maintained.

FIG. 9 is similar to FIG. 8 and illustrates an example GUI 152 that displays an activation field view to the user via the display of programmer 20. From the defined stimulation field 158 on the side view 154 and cross-sectional view 156, processor 60 of programmer 20 may generate stimulation parameter values for therapy and generate an activation field model based upon the electrical field model 160 of FIG. 8 and a neuron model that estimates which neurons within the electrical field model will be activated by the voltage of the electrical field during therapy. The neuron model may be a set of equations, a lookup table, or another type of model that defines threshold action potentials of particular neurons that make up the anatomical structure, as defined by the patient anatomy data, affected by the electrical field 160. If the voltage or current amplitude of the electrical field 160 is above the threshold of any neuron within the electrical field, that neuron will be activated, e.g., cause a nerve impulse. The activation field model is displayed as activation fields 166 and 168 within stimulation field 158.

Activation fields 166 and 168 of the activation field model indicate to the user where neurons around the lead will be activated from the stimulation therapy. Due to changes in electrical current propagation and voltage thresholds to activate a neuron, the activation of neurons may vary with the location of tissue around the lead. Some neurons may activate further from the lead with smaller voltages while other neurons may only be activated close to the lead because of a high voltage threshold. These differences in neurons may account for separate activation fields 166 and 168 within a contiguous stimulation field 158. The user may manipulate activation fields 166, 168 in order to modify the therapy program that resulted in stimulation field 158. For example, the user may increase or decrease the size and/or shape of activation fields 166 and 168 by changing the amplitude with amplitude adjustment interface 162 or directly manipulate the activation fields (e.g., by modifying the borders of the displayed activation fields 166, 168) to automatically modify the stimulation parameters. In both GUI 150 (FIG. 8) and GUI 152 (FIG. 9), the user may view cross-sections at other electrode levels with arrows 138.

Once the user is satisfied with activation fields 166, 168, processor 60 may compare activation fields 166, 168 to a reference field (e.g., a reference activation field) defined by a set of therapy guidelines, as described with respect to FIGS. 4A-4C, and/or analyze the efficiency of therapy system 10 based on the stimulation parameters used to generate activation fields 166, 168, as described with respect to FIG. 5. For example, processor 60 may access a set of therapy guidelines and select a reference therapy field, e.g., via memory 62 or a separate computing device, and compare the reference therapy field to activation fields 166, 166. Additionally or alternatively, processor 60 may analyze the efficiency of therapy system 10 when the selected the stimulation parameters are used to generate activation fields 166 and 168. In some examples, GUI 152 may display the reference field defined by the therapy guidelines, an activation field model associated with the adjusted stimulation parameters that resulted from the comparison to the reference field, and/or a model of the electrical field associated with the adjusted stimulation parameters that resulted from the analysis of the efficiency of therapy system 10.

GUIs 150, 152 also include scroll bars 136, 140, which are described with respect to FIG. 7. In the example shown in FIGS. 8 and 9, GUIs 150, 152 also present field menu button 172 to the user, which may present further options to a user. For example, upon activation of menu button 172, the GUIs 150, 152 may display a menu that enables a user to select a modify stimulation field button to redefine the stimulation field 158, select polarity button to alter the polarity of any of the electrodes, a change field view button to switch between electrical or activation field views 150, 152, and a manual mode button which allows the user to manually select the stimulation parameters in an electrode view that displays the electrodes of the lead.

Although FIGS. 8 and 9 illustrate 2D views of lead 16, in other examples, a user interface may present a 3D view of lead 16 and the associated electrical field and activation fields may be displayed relative to the 3D views of lead 16.

Figure 10:
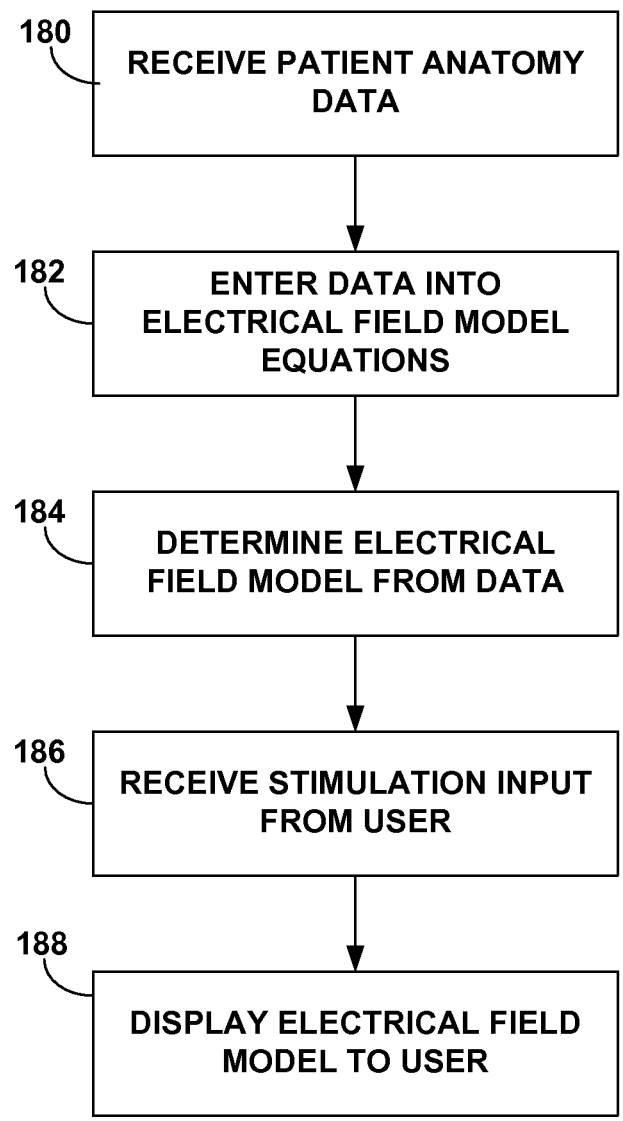
FIG. 10 is a flow diagram illustrating an example technique for calculating and displaying an electrical field model, which is based on a stimulation field.

FIG. 10 is a flow diagram illustrating an example technique for calculating and displaying electrical field model 160 (FIG. 8), which is based on a stimulation field 158. Stimulation field 158 may be determined based on input by a user and/or automatically generated by processor 60 of programmer 20 in response to a therapy program selected by the user. As shown in FIG. 10, processor 60 receives patient anatomy data necessary for creating an electrical field (180), which may include an anatomical image of the target tissue site of patient 12, a reference anatomical image, which may not be specific to patient 12, an anatomical atlas indicating specific structures of the patient's anatomy or a map of the tissue characteristics (e.g., conductivity or density) adjacent to lead 16. As previously described, the patient anatomy data may be created based on a medical imaging technique, such as, but not limited to, CT and MRI data. Processor 60 may store the patient anatomy data within memory 62 (FIG. 3).

Processor 60 may enter the patient anatomy data into stored electrical field model equations or equation sets to satisfy anatomical variable (182). Processor 60 may then determine the electrical field model from the data and equations (184). Once processor 60 receives stimulation input from a user defining the stimulation field, e.g., via user interface 64 (186), the modeled electrical field (algorithmic model) may be displayed to the user via the display of user interface 64 (188). Processor 60 may also compare the algorithmic model of the electrical field to a reference electrical field defined by a set of therapy guidelines, as described with respect to FIGS. 4A-4C, and/or analyze the efficiency of therapy system 10 using the stimulation parameters on which the modeled electrical field is based, as described with respect to FIG. 5.

Figure 11:
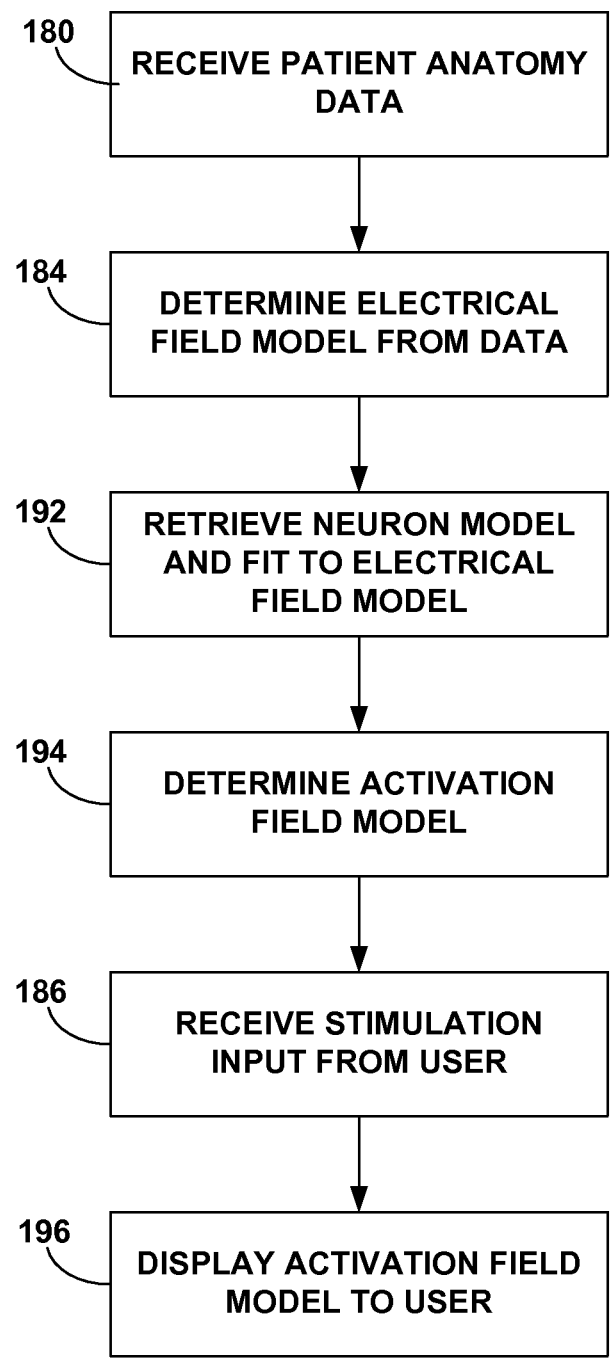
FIG. 11 is a flow diagram illustrating an example technique for calculating and displaying the activation field model of defined stimulation.

FIG. 11 is a flow diagram illustrating an example technique for determining and displaying the activation field model of defined stimulation. As shown in FIG. 11, processor 60 receives patient anatomy data indicative of the anatomy of patient 12 (180) and processor 60 determines the electrical field model from the patient anatomy data (184). Processor 60 retrieves a neuron model from memory 62 (FIG. 3) and fits the neuron model to the electrical field model (192). The neuron model may be stored within of memory 62 (FIG. 3). Processor 60 may determine the activation field model based upon the electrical field model and neuron model (194).

Processor 60 may receive input from a user defining stimulation field 158, e.g., via user interface 64 (186). Processor 60 may present the resulting activation field model to the user via the display of user interface 64 (196). Processor 60 may also compare the algorithmic model of the activation field to a reference activation field defined by a set of therapy guidelines, as described with respect to FIGS. 4A-4C, and/or evaluate the efficiency of therapy system 10 based on the set of stimulation parameters used to generate the stimulation field, as described with respect to FIG. 5.

The techniques shown in FIGS. 10 and 11 may also be used to generate an algorithmic model of a modified therapy field based on the modified therapy program, e.g., a therapy program that was modified based on comparison to a reference therapy field defined by therapy guidelines and/or modified to increase an operating efficiency of therapy system 10. If the algorithmic model of the modified therapy field is an electrical field model, processor 60 may receive patient anatomy data (180), enter the patient anatomy data and the modified therapy program data into electrical field model equations (182), and determine an algorithmic model of an electrical field that is based on the modified therapy program (184) (FIG. 10). If the algorithmic model of the modified therapy field is an activation field model, processor 60 may receive patient anatomy data (180), enter the patient anatomy data and the modified therapy program data into electrical field model equations (182), determine the electrical field model based on the equations (184), and retrieve a neuron model and fit it to the electrical field model (192) in order to determine an activation field model based on the modified therapy program (194) (FIG. 11).

Figure 12:
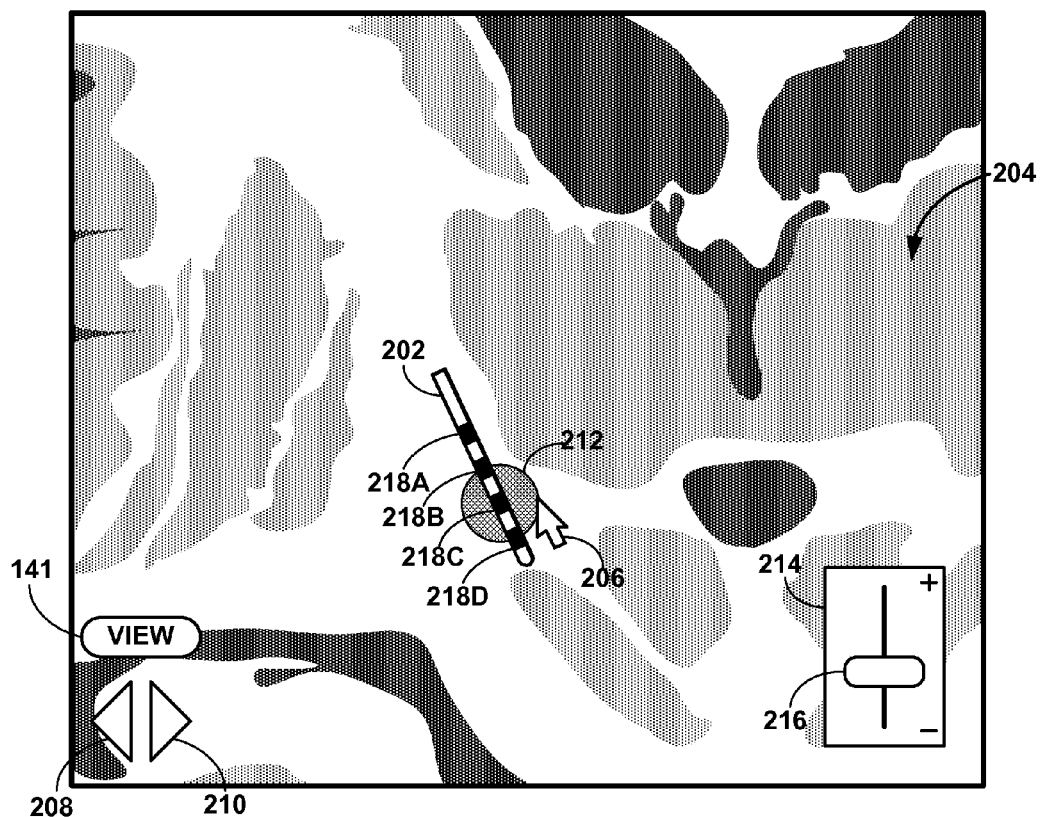
FIG. 12 is a schematic illustration of another example of a GUI that may be presented on the display of the programmer of FIG. 3 in order to help a user generate an algorithmic model of a therapy field.

An algorithmic model of an original therapy field (e.g., a therapy field prior to modification of the therapy parameter values based on a reference therapy field and/or operating efficiency data of the therapy system), a modified therapy field or another algorithmic model of a therapy field may also be generated using other techniques. FIG. 12 is a schematic illustration of another example of GUI 200 that may be presented on the display of programmer 20 in order to help a user generate an algorithmic model of a therapy field, compare the algorithmic model to a reference therapy field, and/or modify a therapy program to increase the operating efficiency of therapy system 10.

A user may interact with GUI 200 via user interface 64 of programmer 20 in order to generate an electrical field model and/or an activation field model. GUI 200 presents a representation of anatomical regions of brain 18. In GUI 200, a lead icon 202 representing lead 16 is displayed to illustrate where lead 16 is actually implanted relative to one or more anatomical regions of brain 18 of patient 12. In particular, GUI 200 displays coronal view 204 of brain 18, which is a front-back vertical section of brain 18. Coronal view 204 may be an actual image of brain 18 produced with MRI, CT, or another imaging modality. These images are used to produce the anatomical regions needed to help the user program the stimulation parameters.

Coronal view 204 is a 2D coronal slice of brain 18. Differently shaded portions of coronal view 204 indicate varying densities of tissue within brain 18. Darker portions indicate less dense tissue. For example, the darkest portion of coronal view 204 is indicative of spaces within brain 18 that contain cerebral spinal fluid (CSF). White portions of brain 18 indicate dense tissue and more neurons. The clinician may be able to recognize target anatomical regions by viewing coronal view 204. It should be noted that coronal view 204 shown in FIG. 12 is merely an example image, and actual images may include a wider range of shades and higher image resolution. Coronal view 204 provides a first perspective of the lead and the anatomical region in which the lead is implanted.

Coronal view 204 further includes pointer 206, previous arrow 208, next arrow 210, stimulation field 212, fine control input mechanism 214, and control slide 216. Pointer 206 may be controlled with a mouse and buttons, a trackball, touch-pad, touch screen or other movement input device, which may be a part of user interface 64 of programmer 20. A user may use pointer 206 to drag lead icon 202 into position or rotate lead icon 202 within coronal view 204 to correctly orient the lead icon according to the actual position of lead 16 within brain 18. The actual position of lead 16 may be determined with the aid of medical imaging techniques, such as MRI or CT. In other examples, the user may first select the type of lead 16 implanted within patient 12 and select the correctly scaled size of lead icon 202 to correspond with the anatomical regions of coronal view 204.

Programmer 20 may initially orient the user to the middle depth of the coronal view 204 or another depth that the programmer automatically selects based upon the type of therapy, implant location, or some other simple indication of location. However, the user may use arrows 208 and 210 to move to another coronal depth where lead 16 is implanted in brain 18. The clinician may zoom in to or out of coronal view 204 for a larger view of anatomical regions of the coronal view. In addition, the clinician may move coronal view 204 up, down, left, or right to view a larger or smaller portion of brain 18. While the clinician may manually position lead icon 202 within coronal view 204, processor 60 may automatically position lead icon 202 within GUI 200 based upon stereotactic data that is generated before lead 16 is implanted within patient 12. A stereotactic frame may be placed on a cranium of patient 12 to specifically locate areas of brain 18. In addition, this stereotactic information may be used to provide coordinates of the exact location of the implanted lead 16. In other examples, brain 18 may be imaged after implantation of lead 16 such that the lead is identifiable on coronal view 204. The user may point to and identify electrodes of lead 16 in the image to allow programmer 20 to reconstruct the correct position of the lead 16. In some cases, programmer 20 may automatically identify lead 16 and place lead icon 202 correctly within the anatomical region without any input from the user.

GUI 200 allows the user to select and adjust stimulation field 212, which is a cross-sectional view of volumetric stimulation field, which may be further defined in other orthogonal views. In order to define stimulation field 212 within coronal view 204, the user may user pointer 206 to select one of electrode levels 218A, 218B, 218C or 218D for delivering the stimulation that results in stimulation field 212. As with the lead shown in FIGS. 8 and 9, an electrode level may have one or more electrodes around the circumference of lead icon 202, e.g., a complex electrode array geometry. All circumferential electrodes of the selected electrode level are initially activated for programming. In some cases, the user may attempt to place stimulation field 212 over the anatomical regions targeted for stimulation therapy while avoiding anatomical regions that may initiate unwanted side effects. In some examples, stimulation field 212 may be a representation of an electrical field, current density, voltage gradient, or neuron activation, applied to a generic human tissue or the anatomy of patient 12. In addition, the clinician may be able to switch between any of these representations when desired.

In the example shown in FIG. 12, the user-selected electrode level 218C and stimulation field 212 shows the anatomical region that would be stimulated with therapy delivery via the selected electrode level 218C. The user may use pointer 206 to drag stimulation field 212 to define a smaller or larger size, which corresponds to a lower or higher voltage or current amplitude. For example, the user may click on a border, or perimeter of stimulation field 212, and then drag the border to expand or contract the field 212. This adjustment is the coarse control of the size of stimulation field 212. The clinician may use pointer 206 to move control slide 216 up to slightly increase the size of stimulation field 212 or down to slightly decrease the size of stimulation field 212. In some examples, the actual voltage or current amplitude associated with stimulation field 212 is displayed on coronal view 204 as stimulation field 212 changes characteristics.

Processor 60 of programmer 20 may limit the rate of movement of stimulation field 212. In other words, stimulation field 212 may only be moved a certain number of steps per second within GUI 200, or any other user interface that allows the clinician to drag the stimulation field. This rate movement limit may prevent unnecessary calculations or ensure patient comfort in real-time changing of stimulation parameters with modifications of stimulation field 212.

The initial size of stimulation field 212 may be determined by a minimal threshold voltage previously determined to provide some efficacious results to patient 12. In other examples, the initial stimulation field size may be small to allow the clinician to safely increase the size of stimulation field 212. The size of stimulation field 212 may be limited by a volume parameter or a maximum voltage limit previously defined by the user or processor 60. The limit may be associated with capabilities of IMD 14 or safe voltage or current levels for patient 12. Once the size of stimulation field 212 is met, the clinician may no longer be able to drag the size of the stimulation field away from lead icon 202.

Stimulation field 212 may grow in size or split if the clinician selects more than one electrode level 218A-218D. For example, the clinician may select electrode levels 218A and 218B to generate stimulation fields associated with each electrode level. The clinician may also move stimulation field 212 along the length of lead icon 202 and processor 60 may automatically select which electrode levels to activate to produce the stimulation field 212. The clinician may also move to other depths or slices of coronal view 204 with arrows 208 and 210. View button 141 may permit a user to switch to another view of brain 18. The other views may include, for example, a sagittal view of brain tissue, which may be taken from a perspective substantially perpendicular to the coronal view 204 or an axial view.

As described in further detail in U.S. patent application Ser. No. 11/591,299 to Stone et al., a programmer 20 may present a GUI including other views of brain 18 in addition to or instead of coronal view 240 in order to help select stimulation parameters for IMD 14. For example, programmer 20 may present a sagittal view of brain tissue or an axial view of brain tissue.

Figure 13:
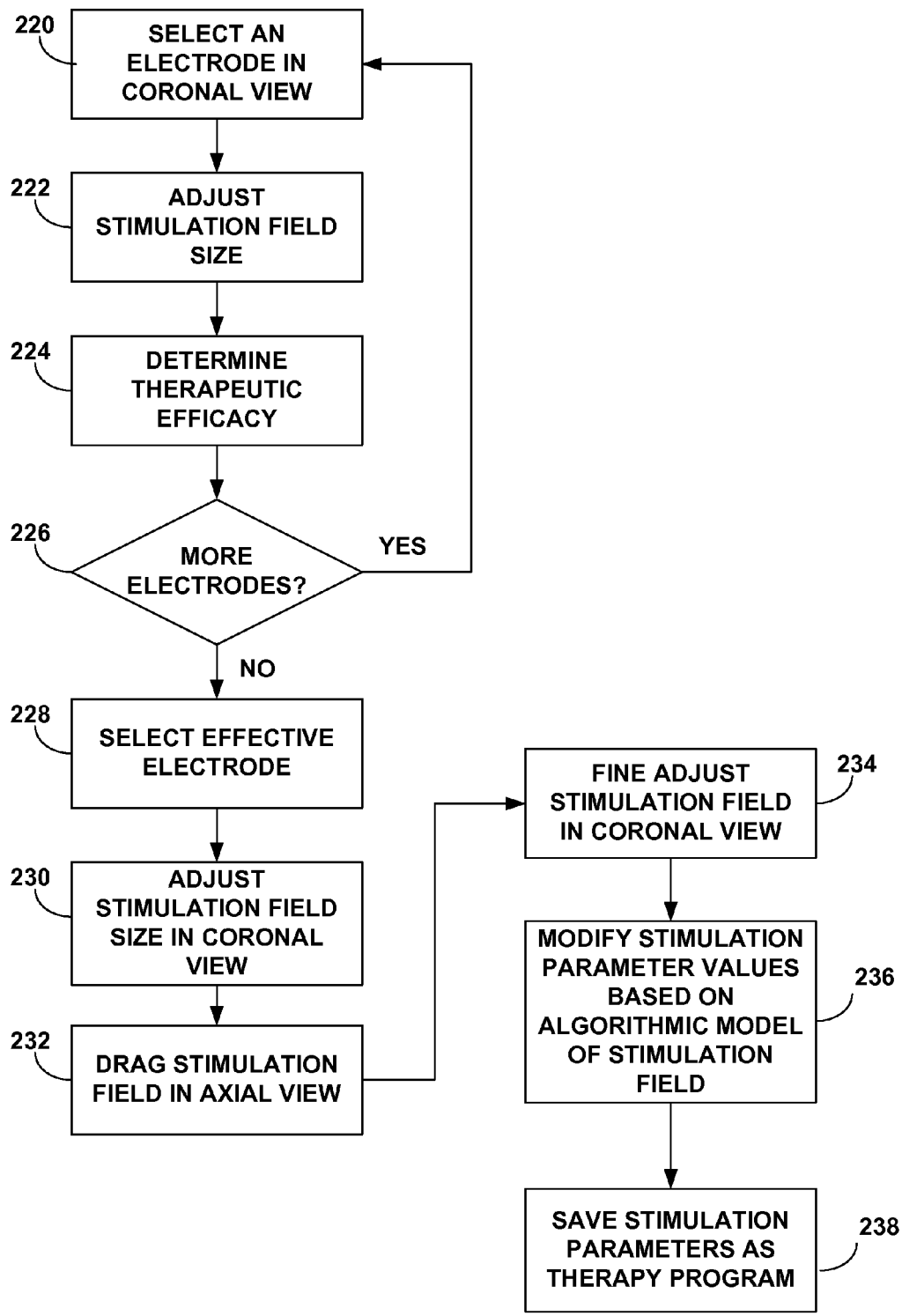
FIG. 13 is a flow diagram illustrating an example technique for adjusting stimulation parameters.

FIG. 13 is a flow diagram illustrating an example technique for adjusting stimulation field 212 for stimulation therapy in order to define stimulation parameter values and generate a therapy program for therapy delivery by IMD 14 and to generate an algorithmic model of a therapy field. As shown in FIG. 13, the clinician begins by selecting an electrode level 218A-218D in coronal view 204 of GUI 200, although other views, such as a sagittal view or axial view of brain 18 may also be used to select an electrode level 218A-218D (220). Processor 60 activates all the electrodes, i.e., electrodes at different angular positions around the lead circumference, in the selected electrode level. The user may interact with GUI 200 in order to adjust a size of stimulation field 212 (222) and test the stimulation field 212 on patient 12 to determine the therapeutic efficacy, if any (224). If the user wants to test stimulation delivered by more electrode levels (226), the user may repeat this process by selecting another electrode level and testing it on patient 12.

If there are no more electrode levels to test, the user may select the most effective electrode level from the tested electrodes (228) and adjust the size of stimulation field 212 by interacting with GUI 200 (230). The user may drag stimulation field 212 within GUI 200 in order to define a field 212 that minimizes side effects and maximizes therapeutic benefits to patient 12 (232). In addition, the user may use fine adjustment buttons 214 and 216 to further adjust stimulation field 212 (234). Additionally, the clinician may use a wand tool to select a range of pixel shades to quickly select anatomical regions that will be included in stimulation field 212.

In some examples, the user may adjust the stimulation field in any of sagittal, coronal, or axial field views as desired by the clinician. In other examples, GUI 200 may require that the clinician enters each of the sagittal, coronal, and axial field views at least once before adjustment of the stimulation can be completed. Processor 60 of programmer 20 may use information received via user interface 64 to automatically generate stimulation parameter values based on the stimulation field 212 defined by the user. Processor 60 may determine the dimensions of the stimulation field 212 to create a 3D vector field identifying the distances from lead 16 that stimulation may reach. Processor 60 may utilize the 3D vector field with an equation approximating electrical current propagation within brain tissue. The resulting data determines respective values for the electrode combination, voltage and current amplitudes, pulse rates, pulse widths, and, in some cases, other stimulation parameter values (e.g., slew rate or duty cycle) needed for reproducing the stimulation field within patient 12. In other examples, processor 60 of programmer 20 interprets density of tissue in the imaging data to more precisely approximate the stimulation parameters.

In some examples, processor 60 may utilize one or more stimulation templates stored within memory 62 in order to determine the stimulation parameter value for achieving the stimulation field 212 defined by the user. As previously described, a stimulation template may be a predetermined volumetric stimulation field that processor 60 may match to a desired stimulation field 212. Each stimulation template may be based upon any one or combination of modeled data, experimental data, or analytical calculations prior to being stored in programmer 60. Stimulation templates are described in further detail in U.S. Pat. No. 7,822,483 to Stone et al.

Once the user has indicated that stimulation field 212 is finalized, and produces effective therapy for patient 12, processor 60 may utilize stimulation field 212 as an algorithmic model of a therapy field and modify at least one of the stimulation parameter values based on a comparison of stimulation field 212 with a reference therapy field (FIGS. 4A-4C) (236). The stimulation parameter values that are modified may be the stimulation parameter values that were determined by processor 60 to result in stimulation field 212 when IMD 14 delivers therapy according to the stimulation parameter values. In another example, processor 60 may utilize stimulation field 212 as an algorithmic model of a therapy field and modify the therapy program based on an analysis of the efficiency of therapy system 10 when therapy is delivered according to the therapy program (FIG. 5) (236).

The user may save the adjusted stimulation parameters that achieve the adjusted stimulation field as a therapy program within memory 62 (FIG. 3) (238). Processor 60 may control the transmission of the therapy program to IMD 14 via telemetry device 66 (FIG. 3). In some examples, the user may repeat the programming procedure with GUI 200 to generate multiple therapy programs and respective algorithmic models of therapy fields. The clinician may also reprogram the therapy at any time with the aid of GUI 200 and generate an algorithmic model of a stimulation field based on the reprogrammed therapy program.

In other examples, a user may generate an algorithmic model of a stimulation field 212 without the aid of a lead icon 202. For example, when presented with the coronal view of the brain, as shown in FIG. 12, the user may create an outline defining the outer edges of stimulation field 212. By defining an algorithmic model of stimulation field 212 by outlining the desired field within GUI 200, the user outlining desired areas includes allowing the user to focus on the anatomy and physiology of patient 12 instead of manipulating an implanted device. Consequently, automatically generating stimulation parameters according to a user-selected stimulation area may increase therapy efficacy and decrease programming time. The user may determine the anatomy with which to focus on with the stimulation field 212 with the aid of therapy guidelines. For example, as shown in FIG. 6C, therapy guidelines may include a listing of target anatomical structures. The target anatomical structures specified by the therapy guidelines may be highlighted, outlined or otherwise differentiated within GUI 200, such that the target anatomical structures associated with the patient condition by the therapy guidelines are easily discernible by the user.

In addition, in other examples, a user may select stimulation parameters and generate an algorithmic model of a therapy field that indicates the field that provides efficacious therapy to patient 12 with the aid of an atlas of an anatomical region of patient 12. The atlas may be represented in the form of a drawing or actual image from an imaging modality such as MRI, CT, or other similar imaging technique. The reference anatomy may be an anatomy different from patient 12 anatomy. Specific structures of the reference anatomy may be identified and their locations within the reference anatomy determined to create an atlas. The atlas may be stored in memory 62 of programmer 20. While an atlas may differ from the actual patient anatomy, the structure locations may be close enough to provide guidance to a user to generate stimulation parameters based upon the atlas. Again, the atlas may highlight, outline or otherwise differentiate particular anatomical structures that are defined by therapy guidelines as being relevant to treating the patient's condition.

In addition, in some examples, the user may generate an algorithmic model of a therapy field with the aid of a user interface that presents, at the same time, an atlas and the actual anatomy of patient 12, e.g., generated by a suitable medical imaging technique. The atlas of the reference anatomy and the patient-specific anatomy may be combined to create a morphed atlas for programming the stimulation therapy. One example of how programmer 20 may create a morphed atlas is described in U.S. Patent Application No. 2005/0070781 by Dawant et al., entitled, "ELECTROPHYSIOLOGICAL ATLAS AND APPLICATIONS OF SAME" and filed Jul. 1, 2004.

Examples of systems and techniques for selecting therapy parameters and generating a resulting stimulation field with the aid of an atlas is described in further detail in U.S. Pat. No. 7,822,483 to Stone et al. In one technique described by U.S. Pat. No. 7,822,483 to Stone et al., a user may use a pointer to select a specific structure of the atlas presented on a user interface of a programmer, and the name of the structure may be is displayed. The programmer may generate stimulation parameters based upon the location of the one or more selected structures to the location of the implanted lead. In some examples described by U.S. Pat. No. 7,822,483 to Stone et al., generating stimulation parameters may include selection of stimulation templates and creation of a stimulation template set based on the selected structures. An atlas may allow a clinician to quickly select the most appropriate structure that needs to be stimulated to treat the condition of patient.

Just as with GUIs 150, 152, an electrical field model or an activation field model may be generated based on a selected stimulation field 212. The electrical field model may approximate actual stimulation effects from therapy. FIG. 14 is an example screen shot of a GUI 240 that presents a sagittal view of a patient anatomy with an algorithmic model of an electrical field 256 of the defined stimulation therapy. Processor 60 may control the display of GUI 240 on the display of programmer 20. The sagittal view of the patient anatomy may be a 2D view of any one of an atlas, a morphed atlas, or a patient anatomical region. GUI 240 also includes previous arrow 242, next arrow 244, menu 246, view indicator 248, and amplitude adjuster 250 with slider 252. The clinician interacts with GUI using pointer 254, which may be similar to pointer 206 (FIG. 12).

Processor 60 of programmer 20 controls GUI 240 to display lead icon 202 and electrical field 256 to present an illustration to the clinician of what the electrical field of the stimulation therapy would look like according to the stimulation parameters defined by the clinician using any of the programming techniques described herein. Electrical field 256 is an algorithmic model that represents where the electrical current will propagate from lead 16 within brain 18, as tissue variation within brain 18 may change the electrical current propagation from the lead. The variations in electrical field propagation may affect the ability of the therapy to actually treat a desired structure or cause a side-effect.

Electrical field 256 is a 2D slice of the volumetric electrical field model created by programmer 20. Processor 60 utilizes the patient anatomical region data with electrical field model equations that define current propagation. Accordingly, electrical field 256 is an algorithmic model of an electrical field that indicates where stimulation will propagate from an implanted lead (represented within GUI 240 by lead icon 202). The clinician may interact with GUI 240 to increase or decrease the amplitude of the stimulation parameters with amplitude adjuster 250 and view how the amplitude change would affect the size and shape of electrical field 256. Amplitude adjuster 250 is an analog adjustment mechanism and may also be in the form of an adjustment knob instead of the slider. The user may move to different depths of the sagittal view with previous arrow 242 or next arrow 244 while adjusting the amplitude of electrical field 256 with slider 252. In some examples, GUI 240 may allow the user to redefine the stimulation field and generate new stimulation parameters if it is believed that electrical field 256 is unacceptable for therapy. Algorithmic model of electrical field 256 may be generated using a technique similar to that shown in FIG. 10.

An algorithmic model of a therapy field, such as an original therapy field based on an original therapy program or a modified therapy field based on a modified therapy program, may also be generated within a 3D environment. FIG. 15 is a conceptual diagram illustrating a 3D visualization environment including a 3D brain model for defining a 3D stimulation field. As shown in FIG. 15, GUI 260 presents a 3D environment 262 that illustrates brain model 264, stimulation field 266, and virtual hand 268. Stimulation field 266 may be stored as an algorithmic model of a therapy field, where stimulation field 266 is generated based on patient anatomy, hardware characteristics of therapy system 10, and the stimulation parameter values of a selected therapy program. However, in some cases, the stimulation parameter values may be selected to achieve stimulation field 266. Thus, in such cases, stimulation field 266 may be generated based on patient anatomy and hardware characteristics of therapy system 10. GUI 260 may be presented by processor 60 on the display of programmer 20. Brain model 264 is a 3D anatomical region and stimulation field 266 is a 3D stimulation field displayed relative to brain model 264. A user may interact with GUI 200 to move hand 268 in order to control the view and aspects of 3D environment 262. In the example shown in FIG. 15, brain model 264 is positioned to illustrate a sagittal view.

3D environment 262 may be displayed on a 2D display by using partially transparent surfaces and grey or color shades. A fully interactive 3D environment 262 may allow a clinician to view within brain model 264 and identify anatomical regions that are targets for stimulation therapy. Brain model 264 may be generated from imaging data from MRI, CT, or another medical imaging modality. While shading of brain model 264 is not shown in FIG. 15, brain model 264 may include shading or other techniques for illustrating different anatomical regions of brain 18.

While a lead icon representing lead 16 is not shown within 3D environment 262, processor 60 may incorporate imaging data into 3D environment 262 after lead 16 is implanted. That is, processor 60 may automatically recognize the orientation and location of lead 16 within patient 12 based on imaging data input into programmer 20, and may present a lead icon within GUI 260 based on the actual orientation and location of lead 16 within patient 12. Alternatively, the user may manually place a lead icon within 3D environment 262 based upon stereotactic data or implant coordinates for the actual lead 16 implanted within patient 12.

Processor 60 may control the presentation of GUI 260 and select the location of stimulation field 266 based upon the implant site of lead 16 within patient 12. A user may then interact with GUI 260 to adjust and manipulate stimulation field 266 as desired with virtual hand 268 or other input mechanisms provided by user interface 64 of programmer 20 (FIG. 3). The user may also use virtual hand 268 to rotate and spin brain model 264 in any direction. GUI 260 may support zooming in and out relative to brain model 264, as well as displaying different perspectives of brain model 264 within 3D environment 262 to see stimulation field 266 within brain model 264 from different perspectives.

GUI 260 may include a wand tool that allows the user to highlight various regions of brain model 264 to be included in stimulation field 266. The wand tool may automatically select voxels (i.e., pixels in all three dimensions). In other dimensions, the clinician may grab one of several predefined stimulation field shapes and place the shape within brain model 264 to become stimulation field 266. In any case, GUI 260 may set limits to stimulation field 266 based upon the characteristics of lead 16 and the capabilities of IMD 14. The safety of patient 12 may also govern the size and location of stimulation field 266.

Figure 16:
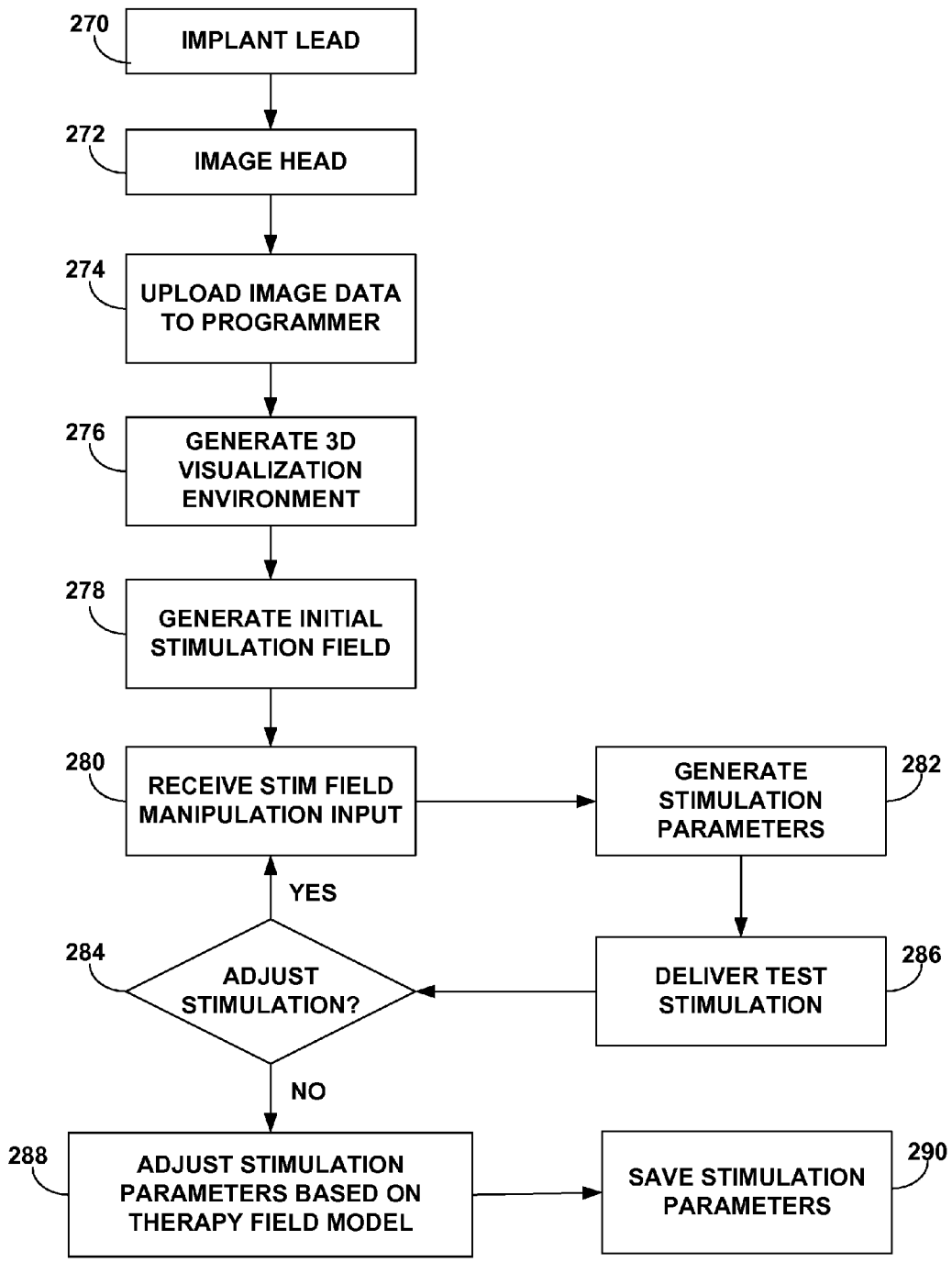
FIG. 16 is a flow diagram illustrating an example technique for defining a 3D stimulation field within a 3D brain model.

FIG. 16 is a flow diagram illustrating an example technique for defining a 3D stimulation field within a 3D brain model of patient 12. As shown in FIG. 16, a user, such as a clinician, may implant lead 16 within brain 18 using any suitable technique, such as a stereotactic technique (270). The clinician, with the aid of an imaging device, may generate an image the head of patient 12 to obtain data of brain 18 necessary for generating the brain model 264 (272). The clinician may upload the image data to a computing device, such as programmer 20 (274). The image data may be stored within memory 62 (FIG. 3). Processor 60 of programmer 20 may generate a 3D visualization environment (276) and generate brain model 264 and the initial stimulation field 266 within the 3D environment (278). The initial stimulation field may be generated with a set of stimulation parameter values that are believed to provide efficacious therapy to patient 12 for the particular patient condition. These initial stimulation parameter values may be specific to patient 12 or may be general to more than one patient. For example, in one example, the initial stimulation parameter values may be specified by a set of therapy guidelines stored within memory 62 of programmer 20.

With the aid of user interface 64, processor 60 may receive stimulation field input from a clinician, such as adjustments and manipulations to stimulation field 266 within the 3D environment (280). Processor 60 may generate stimulation parameter values based on the stimulation field 266 resulting form the adjustments and manipulations from the user (282) and control IMD 14 to deliver test stimulation with the parameters (286). If the clinician desires to adjust stimulation parameters (284) based on the feedback from patient 12 and/or sensors, processor 60 may continue receiving stimulation field input (280) and testing the stimulation according to the modification to stimulation field 266 (282, 286). If the stimulation therapy is effective, processor 60 may utilize stimulation field 266 as an algorithmic model of a therapy field and adjust the stimulation parameter values based on stimulation field 266 (236). For example, processor 60 may compare stimulation field 266 to a reference electrical field defined by therapy guidelines and/or analyze the efficiency of therapy system 10 using the set of stimulation parameter values that are used to generate stimulation field 266 (288). The clinician may save the adjusted stimulation parameter values as a therapy program in IMD 14 so that patient 12 can receive therapy with the set of adjusted stimulation parameter values (290).

In addition to or instead of using stimulation field 266 as an algorithmic model of a therapy field, such as an original therapy field or a modified therapy field, an electrical field model and/or activation model may be generated based on stimulation field 266 and stored as an algorithmic model of a therapy field. The electrical field model and activation field model may be generated by processor 60 using any suitable technique, such as the techniques shown in FIGS. 10 and 11, and displayed within 3D environment 262 using any suitable technique, such as those described in U.S. Pat. No. 7,822,483 to Stone et al. The clinician or other user may modify the stimulation parameters by directly modifying the size, shape or location of the electrical field model or activation field model within 3D environment 262, or the clinician may modify the electrical field model or activation field model may directly modifying the stimulation parameters.

While the description primarily refers to electrical stimulation therapy, in some cases, an algorithmic model of a therapy field resulting from the delivery of a therapeutic agent to a target tissue site within patient 12 may be used to guide the modification of therapy parameters. In the case of therapeutic agent delivery, the therapy parameters may include the dosage of the therapeutic agent (e.g., a bolus size or concentration), the rate of delivery of the therapeutic agent, the maximum acceptable dose in each bolus, a time interval at which a dose of the therapeutic agent may be delivered to a patient (lock-out interval), and so forth. Example therapeutic agents include, but are not limited to, pharmaceutical agents, insulin, pain relieving agents, anti-inflammatory agents, gene therapy agents, or the like.

Just as with the stimulation systems 10, 30 described above, for a therapy system that includes delivery of a therapeutic agent, an algorithmic model of a therapy field may be generated with the aid of modeling software, hardware or firmware executing on a computing device, such as programmer 20 or a separate dedicated or multifunction computing device. The algorithmic model of the therapy field may represent where therapy will propagate from the therapy system that delivers the one or more therapeutic agents according to a particular therapy parameter set, i.e., therapy program. In some examples, the therapy field model may be based on an anatomical data set, such as tissue density data, body fluid pressure, body fluid flow rates, body fluid diffusion rates, and effective duration of the therapeutic agent on the target tissue. Again, the anatomical data set may be specific to the patient or may be general to more than one patient. The anatomical data set may comprise at least one of an anatomical image of a patient, a reference anatomical image, or an anatomical atlas.

In some cases, the algorithmic model of a therapy field resulting from delivery of a therapeutic agent may indicate the anatomic structures or the tissue area that are affected by the therapeutic agent. For example, if the therapeutic agent delivers a genetic material to a target tissue site within a patient, where the genetic material causes transgene expression by tissue at the stimulation site, the therapy field may indicate the region of tissue that results in the transgene expression. The transgene expression may include an increased expression of proteins, such as connexins, gap junctions, and ion channels, to increase the conductivity of the tissue at the target tissue site, or the delivered genetic material may cause expression of a metalloproteinase, an anti-inflammatory agent, or an immunosuppressant agent.

As another example, if the therapeutic agent delivers a pain relieving agent to a target tissue site within a patient, the algorithmic model of the therapy field may indicate the region of tissue that absorbs the pain relieving agent and/or the region of paresthesia or other physiological effects that may result from delivery of the therapeutic agent to the target tissue site.

The algorithm for generating an algorithmic model of a therapy field resulting from delivery of one or more therapeutic agents may be generated with the aid of computer modeling techniques. The algorithmic model of the therapy field may indicate the diffusion of the therapeutic agent through the patient's body from a therapy delivery element. The algorithmic model may be an algorithmic model that is generated based on a patient anatomy, the patient's tissue characteristics, and therapeutic agent delivery parameter values. In one example, the algorithm includes equations that define drug propagation through the patient's tissue based on the physical tissue characteristics (e.g., density) and body fluid flow, pressure, and diffusion characteristics adjacent the therapy delivery element. The drug propagation equations may be specific to patient 12 or may be based on information not specific to patient 12. From this information, processor 60 of programmer 20 may be able to generate the estimated therapeutic agent propagation field that will be produced in therapy.

In relatively static body fluids, such as like the spinal cord fluid (SCF), the drug propagation equations may define a simple diffusion model coupled with a model of the therapeutic agent's effective duration within the patient's body. Physiological parameters such a pressure at the target tissue site may impact the diffusion rate. In relatively kinetic body fluids, such as the blood stream, the drug propagation equations may define a diffusion model that also considers the body fluid pressure as well as the body fluid flow rate. Generally, these body fluid characteristics, such as flow rate and pressure, may change relatively quickly for a patient, e.g., based on hydration, heart rate, and the like. Accordingly, sensors may be used to regularly determine the body fluid characteristics, and provide feedback to processor 60 (or a processor of the therapeutic agent delivery device or another device), which may then generate an algorithmic model of the diffusion of the therapeutic agent and determine whether one or more parameter values of the therapeutic agent delivery are desirable based on the modeled diffusion.

Just as with electrical stimulation therapy, therapy guidelines for a therapy system that includes therapeutic agent delivery may set forth a reference therapy field that indicates a therapy field that is known to provide efficacious therapy to manage the patient's condition, as well as identify target anatomical structures for the delivery of the therapeutic agent and expected therapeutic outcomes when therapy is delivered based on the reference therapy field and/or to the identified target anatomical structures.

The techniques described in this disclosure, including those attributed to IMD 14, programmer 20, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 40 of IMD 14 and/or processor 60 of programmer 20, any one or more parts of the techniques described herein may be implemented by a processor of one of IMD 14 or programmer 20, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

The invention claimed is:

1. A method comprising:
   determining, by a processor, a first therapy program that comprises a set of therapy parameters values;
   generating, by the processor, an algorithmic model of a therapy field based on the first therapy program, the algorithmic model representing where therapy will propagate from a therapy system delivering therapy according to the first therapy program; and
   automatically determining, by the processor, a second therapy program that increases an operating efficiency of the therapy system while substantially maintaining the therapy field.

2. The method of claim 1, further comprising controlling, by the processor, the therapy system to deliver therapy to a patient according to the second therapy program.

3. The method of claim 1, wherein the algorithmic model of the therapy field comprises a first algorithmic model of a first therapy field, the method further comprising generating, by the processor, a second algorithmic model of a second therapy field representing where therapy will propagate from the therapy system based on the second therapy program.

4. The method of claim 3, further comprising presenting the first algorithmic model of the first therapy field and the second algorithmic model of the second therapy field to a user.

5. The method of claim 1, wherein automatically determining the second therapy program comprises automatically determining the second therapy program based on at least one of an amplitude-duration curve, a dose-response curve, a strength-duration curve, or a three-dimensional (3D) depolarization field model.

6. The method of claim 5, wherein the at least one amplitude-duration curve, dose-response curve, strength-duration curve, or 3D depolarization field model is configured based on at least one of a patient condition, a desired therapeutic outcome, or a tissue characteristic of a target delivery site.

7. The method of claim 1, wherein the second therapy program increases the operating efficiency of the therapy system by at least one of decreasing power consumption or operating at an efficient amplitude determined based on a voltage multiplier level.

8. The method of claim 1, wherein the algorithmic model of the therapy field comprises a first algorithmic model of a first therapy field, the method further comprising generating a second algorithmic model of a second therapy field based on the second therapy program, wherein substantially maintaining the therapy field comprises maintaining a difference between the first therapy field and the second therapy field below a threshold value, wherein the threshold value defines a maximum allowable change in at least one field characteristic.

9. The method of claim 8, wherein the at least one field characteristic comprises at least one of a centroid, a volume, an amplitude, a width at a defined amplitude, or a charge density.

10. The method of claim 8, wherein the threshold value comprises a weighted threshold of a plurality of field characteristics.

11. The method of claim 1, wherein generating the algorithmic model of the therapy field comprises representing where therapy will propagate from the therapy system based upon the first therapy program and an anatomical data set.

12. The method of claim 11, wherein the anatomical data set comprises at least one of an anatomical image of a patient, a reference anatomical image, an anatomical atlas, or a tissue conductivity data set.

13. The method of claim 1, wherein the therapy parameters comprise at least one of an electrode combination, pulse width, frequency or amplitude.

14. The method of claim 1, wherein the algorithmic model of the therapy field comprises at least one of a two dimensional algorithmic model or a three dimensional algorithmic model.

15. A therapy system comprising:
    a medical device configured to deliver a therapy to a patient according to a first therapy program that comprises a first set of therapy parameters; and
    a processor configured to:
      generate an algorithmic model of a therapy field based on the first therapy program, wherein the algorithmic model represents where the therapy will propagate from the medical device delivering therapy according to the first therapy program, and
      automatically determine a second therapy program that increases an operating efficiency of the therapy system while substantially maintaining the therapy field.

16. The therapy system of claim 15, wherein the medical device is configured to deliver therapy from the therapy system to the patient according to the second therapy program.

17. The therapy system of claim 15, wherein the algorithmic model of the therapy field comprises a first algorithmic model of a first therapy field, and wherein the processor is configured to generate a second algorithmic model of a second therapy field that represents where the therapy will propagate from the therapy system based on the second therapy program.

18. The therapy system of claim 17, further comprising a user interface that presents the first algorithmic model of the first therapy field and the second algorithmic model of the second therapy field to a user.

19. The therapy system of claim 15, wherein the processor is configured to automatically determine the second therapy program based on at least one of at least one of an amplitude-duration curve, a dose-response curve, a strength-duration curve, or a three-dimensional (3D) depolarization field model.

20. The therapy system of claim 19, wherein the at least one amplitude-duration curve, dose-response curve, strength-duration curve, or 3D depolarization field model is based on at least one of a patient condition, a desired therapeutic outcome, or a tissue characteristic of a target delivery site.

21. The therapy system of claim 15, wherein the second therapy program increases the operating efficiency of the therapy system by at least one of decreasing power consumption or operating at an efficient amplitude determined based on voltage multiplier levels.

22. The therapy system of claim 15, wherein the algorithmic model of the therapy field comprises a first algorithmic model of a first therapy field, wherein the processor is configured to generate a second algorithmic model of a second therapy field based on the second therapy program, and wherein substantially maintaining the therapy field comprises maintaining a difference between the first therapy field and the second therapy field below a threshold value, wherein the threshold value comprises a maximum allowable change in at least one field characteristic.

23. The therapy system of claim 22, wherein the at least one field characteristic comprises at least one of a centroid, an area, an amplitude, a width at a defined amplitude, or a charge density.

24. The therapy system of claim 22, wherein the threshold value comprises a weighted threshold of a plurality of field characteristics.

25. The therapy system of claim 15, wherein the processor is configured to generate the algorithmic model of the therapy field based upon the set of therapy parameters and an anatomical data set.

26. The therapy system of claim 15, wherein the medical device comprises the processor.

27. The therapy system of claim 15, further comprising a medical device programmer that comprises the processor.

28. The therapy system of claim 15, wherein the medical device is configured to deliver at least one of electrical stimulation therapy or a therapeutic agent to the patient.

29. A system comprising:
  means for determining a first therapy program that comprises a set of therapy parameters values;
  means for generating an algorithmic model of a therapy field based on the first therapy program, the algorithmic model representing where therapy will propagate from a therapy system delivering therapy according to the first therapy program; and
  means for automatically determining a second therapy program that increases an operating efficiency of the therapy system while substantially maintaining the therapy field.

30. The system of claim 29, wherein the means for automatically determining the second therapy program determines the second therapy program based on at least one of at least one of an amplitude-duration curve, a dose-response curve, a strength-duration curve, or a three-dimensional (3D) depolarization field model.

* * * * *